(12) United States Patent
Iwata et al.

(10) Patent No.: US 8,598,367 B2
(45) Date of Patent: Dec. 3, 2013

(54) NITROGEN-CONTAINING HETEROCYCLIC COMPOUND AND PEST CONTROL AGENT

(71) Applicant: Nippon Soda Co., Ltd., Tokyo (JP)

(72) Inventors: Jyun Iwata, Naka-gun (JP); Masahiro Kawaguchi, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 13/749,911

(22) Filed: Jan. 25, 2013

(65) Prior Publication Data

US 2013/0137876 A1    May 30, 2013

Related U.S. Application Data

(62) Division of application No. 13/062,037, filed as application No. PCT/JP2009/004601 on Sep. 15, 2009, now Pat. No. 8,362,257.

(30) Foreign Application Priority Data

Sep. 18, 2008 (JP) ................................. 2008-239724

(51) Int. Cl.
*C07D 261/04* (2006.01)

(52) U.S. Cl.
USPC ........................................................ 548/240

(58) Field of Classification Search
None
See application file for complete search history.

(56) References Cited

U.S. PATENT DOCUMENTS

| | | | |
|---|---|---|---|
| 7,947,715 B2 | 5/2011 | Mita et al. | |
| 7,951,828 B1 * | 5/2011 | Mita et al. | 514/378 |
| 8,242,283 B2 * | 8/2012 | Mita et al. | 548/240 |
| 8,318,757 B2 * | 11/2012 | Mita et al. | 514/274 |
| 8,372,867 B2 * | 2/2013 | Mihara et al. | 514/340 |
| 2011/0144334 A1 * | 6/2011 | Mita et al. | 544/333 |

FOREIGN PATENT DOCUMENTS

| | | |
|---|---|---|
| JP | 2007-016017 A | 1/2007 |
| WO | WO 2005/051932 A1 | 6/2005 |
| WO | WO 2005/085216 A1 | 9/2005 |
| WO | WO 2006/016237 A2 | 2/2006 |
| WO | WO 2007/075459 A2 | 7/2007 |
| WO | WO 2007/105814 A1 | 9/2007 |

* cited by examiner

*Primary Examiner* — Jason M Nolan
*Assistant Examiner* — Po-Chih Chen
(74) *Attorney, Agent, or Firm* — Foley & Lardner LLP

(57) ABSTRACT

The present invention offers compounds or their salts expressed by formula (I)
(in the formula, X indicates an alkyl group, or the like; Y indicates an alkyl group; Z indicates a respectively independent nitro group, or the like; n indicates any integer from 0 to 3; A indicates carbon atom, or the like, and hydrogen atom is bonded thereto in the case where the carbon atom is not substituted with Z; D indicates oxygen atom, or the like; W indicates hydrogen atom, or the like; $R^1$ and $R^2$ indicate respectively independent hydrogen atoms, or the like; $R^1$ and $R^2$ may be bonded, and may form a heterocycle together with the nitrogen atom between $R^1$ and $R^2$).

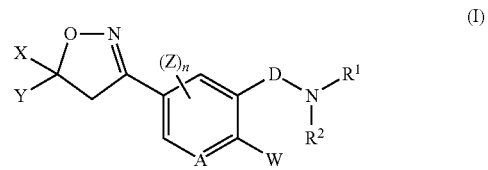

(I)

3 Claims, No Drawings

NITROGEN-CONTAINING HETEROCYCLIC COMPOUND AND PEST CONTROL AGENT

CROSS-REFERENCE TO RELATED APPLICATIONS

This application is a Division of U.S. application No. 13/062,037, which is the U.S. National Stage application of PCT/JP2009/004601, filed Sep. 15, 2009, which claims priority from Japanese patent application JP 2008-239724, filed Sep. 18, 2008. The entire contents of each of the aforementioned applications are incorporated herein by reference.

TECHNICAL FIELD

The present invention relates to novel nitrogen-containing heterocyclic compounds or their salts, and to pest control agents which contain at least one type of these compounds as an active ingredient.

Priority is claimed on Japanese Patent Application No. 2008-239724, filed Sep. 18, 2008, the content of which is incorporated herein by reference.

BACKGROUND ART

Heretofore, numerous pest control agents such as insecticides and acaricides have been used, but many cannot necessarily be considered as satisfactory control agents, because their efficacy has been insufficient, or because their use has been limited due to drug resistance problems, or because they have caused harmful effects or contamination in plants, or have been strongly toxic with respect to humans, animals, fish, and the like. Accordingly, there has been a need for development of chemical agents that can be safely used with few of the pertinent drawbacks.

As a compound with a skeleton that resembles the compounds of the present invention, the following compound is recorded in Patent Document 1.

[Chemical Formula 1]

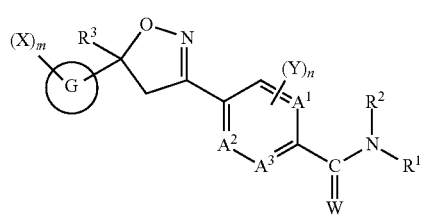

(1)

(In the formula, W indicates oxygen atom or sulfur atom; $A^1$, $A^2$, and $A^3$ are respectively independent, and indicate carbon atom or nitrogen atom; X indicates a halogen atom or the like; Y indicates a halogen atom or the like; n indicates any integer from 0 to 4; $R^1$ and $R^2$ are respectively independent, and indicate hydrogen atom, a C1-12 alkyl group, or the like; $R^3$ indicates a halogen atom or the like; and G indicates a phenyl group or the like.)

The following compound is recorded in Patent Document 2.

[Chemical Formula 2]

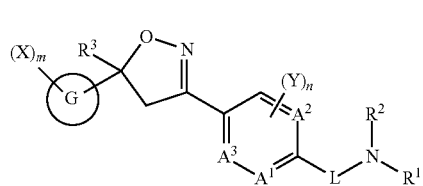

(2)

(In the formula, L indicates —C(Ra)(Rb)—, —N(Rc)—, or the like; $A^1$, $A^2$, and $A^3$ are respectively independent, and indicate carbon atom or nitrogen atom; X indicates a halogen atom or the like; Y indicates a halogen atom or the like; n indicates any integer from 0 to 4; $R^1$ indicates hydrogen atom, —CHO or the like; $R^2$ indicates hydrogen atom, a C1-12 alkyl group, or the like; $R^3$ indicates a halogen atom or the like; and G indicates a phenyl group or the like.)

However, the compounds of the present invention are not recorded in the foregoing literature.

PRIOR ART LITERATURE

Patent Literature

Patent Document 1: Pamphlet of International Publication WO 2005/085216
Patent Document 2: Pamphlet of International Publication WO 2007/105814

DISCLOSURE OF INVENTION

Problems that the Invention is to Solve

The object of the present invention is to offer novel nitrogen-containing heterocyclic compounds and their salts which can be industrially and expediently synthesized, and which are capable of constituting the active ingredient of pest control agents that can be safely used to reliable effect, as well as pest control agents which respectively contain at least one type of these compounds as an active ingredient.

Means for Solving the Problems

The present invention relates to compounds expressed by formula (I):

[Chemical Formula 3]

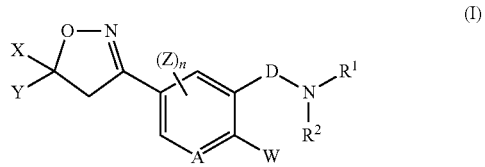

(I)

{In the formula, X indicates an alkyl group, alkenyl group, alkynyl group, aryl group, or heteroaryl group. Y indicates an alkyl group. Z indicates a respectively independent nitro group, hydroxyl group, mercapto group, halogen atom, group expressed by $N(R^a)_2$ (in the formula, each $R^a$ indicates a respectively independent hydrogen atom or a hydrocarbon group), alkyl group, or cyano group. n indicates any integer from 0 to 3. A indicates carbon atom or nitrogen atom, and hydrogen atom is bonded thereto in the case where the carbon atom is not substituted with Z. D indicates oxygen atom, C(O) group, group expressed by the following formula

[Chemical Formula 4]

(in the formula, $R^{b1}$ and $R^{b2}$ indicate hydrogen atoms or organic groups that are respectively independent; n1 indicates 1 or 2), or group expressed by N(R$^c$) (in the formula, R$^c$ indicates hydrogen atom or hydrocarbon group). W indicates hydrogen atom, halogen atom, cyano group, nitro group, alkyl group, alkoxy group, group expressed by N(R$^d$)$_2$ (in the formula, each R$^d$ indicates a respectively independent hydrogen atom or hydrocarbon group), alkylthio group, alkylsulfinyl group, alkylsulfonyl group, or heteroaryl group. R$^1$ and R$^2$ indicate respectively independent hydrogen atoms, acyl groups, or alkoxycarbonyl groups. R$^1$ and R$^2$ may be bonded, and may form a heterocycle together with the nitrogen atom between R$^1$ and R$^2$} or their salts.

In addition, the present invention relates to a pest control agent—particularly to an insecticide or acaricide—that contains the compound expressed by the aforementioned formula (I) or its salt as an active ingredient.

Effects of the Invention

According to the present invention, novel nitrogen-containing heterocyclic compounds or their salts are offered which can be industrially and expediently synthesized, and which are capable of constituting the active ingredient of pest control agents that can be safely used to reliable effect, as well as pest control agents that respectively contain at least one type of these compounds as an active ingredient.

BEST MODE FOR CARRYING OUT THE INVENTION

The present invention is described below in detail.
1. Compounds Expressed by Formula (I) or their Salts The compounds of the present invention are compounds expressed by the aforementioned formula (I) (hereinafter referred to as "compounds of the present invention") or their salts. Moreover, the present invention also includes solvates, crystal polymorphs and the like of the compounds of the present invention or their salts.

Each group in formula (I) is described below. In the present invention, each group may have substituents within a scope that is chemically permissible. When a carbon number is stipulated below, it does not include the carbon number of a substituent.

(X)

X indicates an alkyl group, alkenyl group, alkynyl group, aryl group, or heteroaryl group.

As the "alkyl group" of X, one may cite a methyl group, ethyl group, n-propyl group, i-propyl group, n-butyl group, s-butyl group, i-butyl group, t-butyl group, n-pentyl group, n-hexyl group, nonyl group, isononyl group, decyl group, lauryl group, tridecyl group, myristyl group, pentadecyl group, palmityl group, heptadecyl group, stearyl group, and the like. A C1-6 alkyl group is preferable. The alkyl group may have at least one substituent of at least a single type selected from among the substituent groups shown in the below Table 1.

As the "alkenyl group" of X, one may cite a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group, 5-hexenyl group, and the like. A C2-6 alkenyl group is preferable. The alkenyl group may have at least one substituent of at least a single type selected from among the substituent groups shown in the below Table 1.

As the "alkynyl group" of X, one may cite an ethynyl group, 1-propinyl group, 2-propinyl group, 1-butinyl group, 2-butinyl group, 3-butinyl group, 1-methyl-2-propinyl group, 2-methyl-2-propinyl group, 1-pentinyl group, 2-pentinyl group, 3-pentinyl group, 4-pentinyl group, 1-methyl-2-butinyl group, 2-methyl-2-butinyl group, 1-hexinyl group, 2-hexinyl group, 3-hexinyl group, 4-hexinyl group, 5-hexinyl group, 1-heptinyl group, 1-octinyl group, 1-decinyl group, and the like. A C2-6 alkynyl group is preferable. The alkynyl group may have at least one substituent of at least a single type selected from among the substituent groups shown in the below Table 1.

The "aryl group" of X signifies a monocyclic or polycyclic aryl group. Here, in the case of a polycyclic aryl group, both fully unsaturated and partially unsaturated groups are included. For example, one may cite a phenyl group, naphtyl group, azulenyl group, indenyl group, indanyl group, tetralinyl group, and the like. A C6-10 aryl group is preferable. The aryl group may have at least one substituent of at least a single type selected from among the substituent groups shown in the below Table 1.

With respect to the "heteroaryl group" of X, it includes 5- to 7-membered monocyclic or polycyclic aromatic heterocycles having 1-4 nitrogen atoms, oxygen atoms, or sulfur atoms as hetero atoms, as well as condensed cycles that condense benzene and 5- to 7-membered heterocycles having 1-4 nitrogen atoms, oxygen atoms, or sulfur atoms as hetero atoms. As heteroaryl groups, one may cite, for example, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, napthyridinyl, furopyridinyl, and the like. The heteroaryl group may have at least one substituent of at least a single type selected from among the substituent groups shown in the below Table 1.

TABLE 1

| Substituent Groups | |
|---|---|
| Substituent Type | Exemplifications |
| Hydroxyl groups | |
| Thiol groups | |
| Halogen atoms | Fluorine atoms, chlorine atoms, bromine atoms, iodine atoms, and the like |
| Cyano groups | |
| Isocyano groups | |
| Nitro groups | |
| Isocyanato groups | |
| Isothiocyanato groups | |

TABLE 1-continued

Substituent Groups

| Substituent Type | Exemplifications |
| --- | --- |
| Cyanato groups | |
| Thiocyanato groups | |
| Carboxyl groups | |
| Amino groups | |
| Alkyl groups | Methyl group, ethyl group, n-propyl group, i-propyl group, n-butyl group, s-butyl group, i-butyl group, t-butyl group, n-pentyl group, n-hexyl group, n-decyl group, n-dodecyl group, and the like; a C1-6 alkyl group is preferable |
| Cycloalkyl groups | Cyclopropyl group, cyclobutyl group, cyclopentyl, cyclohexyl group, cycloheptyl group, and the like; a C3-8 cycloalkyl group is preferable |
| Alkenyl groups | Vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group, 5-hexenyl group, 1-decenyl group, and the like; a C2-6 alkenyl group is preferable |
| Cycloalkenyl groups | Cyclopropenyl group, 2-cyclopentenyl group, 3-cyclohexenyl, 4-cyclooctenyl group, and the like; a C3-8 cycloalkenyl group is preferable |
| Alkynyl groups | Ethynyl group, 1-propinyl group, 2-propinyl group, 1-butinyl group, 2-butinyl group, 3-butinyl group, 1-methyl-2-propinyl group, 2-methyl-3-butinyl group, 1-pentinyl group, 2-pentinyl group, 3-pentinyl group, 4-pentinyl group, 1-methyl-2-butinyl group, 2-methyl-3-pentinyl group, 1-hexinyl group, 1,1-dimethyl-2-butinyl group, 1-decinyl group, and the like; a C2-6 alkynyl group is preferable |
| Haloalkyl groups | Chloromethyl group, fluoromethyl group, bromomethyl group, dichloromethyl group, difluoromethyl group, dibromomethyl group, trichloromethyl group, trifluoromethyl group, bromodifluoromethyl group, 1,1,1-trifluoroethyl group, 1-chloroethyl group, 2-chloroethyl group, 1-bromoethyl group, pentafluoroethyl group, and the like; a C1-6 haloalkyl group is preferable |
| Aryl groups | Phenyl group, 1-naphtyl group, 2-naphtyl group, 1-indanyl group, 2-indanyl group, 1-indenyl group, 2-indenyl group, and the like; a C6-10 aryl group is preferable |
| Unsaturated 5-membered heterocyclic groups | Furan-2-yl group, furan-3-yl group, thiophen-2-yl group, thiophen-3-yl group, pyrrol-2-yl group, pyrrol-3-yl group, oxazol-2-yl group, oxazol-4-yl group, oxazol-5-yl group, thiazol-2-yl group, thiazol-4-yl group, thiazol-5-yl group, isooxazol-3-yl group, isooxazol-4-yl group, isooxazol-5-yl group, isothiazol-3-yl group, isothiazol-4-yl group, isothiazol-5-yl group, imidazol-2-yl group, imidazol-4-yl group, imidazol-5-yl group, pyrazol-3-yl group, pyrazol-4-yl group, pyrazol-5-yl group, 1,3,4-oxadiazol-2-yl group, 1,3,4-thiadiazol-2-yl group, 1,2,3-triazol-4-yl group, 1,2,4-triazol-3-yl group, 1,2,4-triazol-5-yl group, and the like |
| Unsaturated 6-membered heterocyclic groups | Pyridin-2-yl group, pyridin-3-yl group, pyridin-4-yl group, pyridazin-3-yl group, pyridazin-4-yl group, pyrazin-2-yl group, pyrimidin-2-yl group, pyrimidin-4-yl group, pyrimidin-5-yl group, 1,3,5-triazin-2-yl group, 1,2,4-triazin-3-yl group, and the like |
| Saturated heterocyclic groups | Tetrahydrofuran-2-yl group, tetrahydrofuran-4-yl group, piperidin-3-yl group, pyrrolidin-2-yl group, morpholine group, piperidino group, N-methylpiperazinyl group, and the like |
| Monoalkyl amino groups | Methyl amino group, ethyl amino group, and the like |
| Monoaryl amino groups | Anilino group, 1-naphtyl amino group, and the like |
| Dialkyl amino groups | Dimethyl amino group, diethyl amino group, and the like |
| Diaryl amino groups | Diphenyl amino group, diindanyl amino group, and the like |
| Alkylsulfonyl amino groups | Methylsulfonyl amino group, ethylsulfonyl amino group, n-propylsulfonyl amino group, isopropylsulfonyl amino group, n-butylsulfonyl amino group, t-butylsulfonyl amino group, and the like |
| Arylsulfonyl amino groups | Phenylsulfonyl amino group, indanylsulfonyl amino group, and the like |
| Heteroarylsulfonyl amino groups | Pyridin-3-ylsulfonyl amino group, furan-2-ylsulfonyl amino group, and the like |
| Alkylcarbonyl amino groups | Methylcarbonyl amino group, ethylcarbonyl amino group, n-propylcarbonyl amino group, isopropylcarbonyl amino group, and the like |

TABLE 1-continued

Substituent Groups

| Substituent Type | Exemplifications |
| --- | --- |
| Alkoxycarbonyl amino groups | Methoxycarbonyl amino group, ethoxycarbonyl amino group, n-propoxycarbonyl amino group, isopropoxycarbonyl amino group, and the like |
| Bis (alkylsulfonyl) amino groups | Bis (methylsulfonyl) amino group, bis (ethylsulfonyl) amino group, (ethylsulfonyl) (methylsulfonyl) amino group, bis (n-propylsulfonyl) amino group, bis (isopropylsulfonyl) amino group, bis (n-butylsulfonyl) amino group, bis (t-butylsulfonyl) amino group, and the like |
| N-unsubstituted or N-substituted iminoalkyl groups | N-methyliminomethyl group, 1-N-phenyliminoethyl group, N-hydroxyiminomethyl group, N-methoxyiminomethyl group, and the like<br>A N-unsubstituted or N-substituted imino $C_{1-6}$ alkyl group is preferable. |
| Arylalkyl groups | Benzyl group, phenethyl group, and the like<br>A $C_{6-10}$ aryl $C_{1-6}$ alkyl group is preferable. |
| Unsaturated 6-membered heterocyclic alkyl groups | Pyridin-2-ylmethyl group, pyridin-3-ylmethyl group, 6-chloropyridin-3-ylmethyl group, pyrimidi-2-ylmethyl group, and the like;<br>an unsaturated 6-membered heterocyclic $C_{1-6}$ alkyl group is preferable. |
| Unsaturated 5-membered heterocyclic alkyl groups | Furan-2-yl-methyl group, thiophen-3-ylmethyl group, 1-methyl-pirazol-3-ylmethyl group, and the like;<br>an unsaturated 5-membered heterocyclic $C_{1-6}$ alkyl group is preferable |
| Saturated heterocyclic alkyl groups | Tetrahydrofaran-2-yl methyl group, piperazine-3-ylmethyl group, N-methyl-pyrrolidin-3-ylmethyl group, morpholinomethyl group, and the like |
| Alkoxy groups | Methoxy group, ethoxy group, n-propoxy group, isopropoxy group, n-butoxy group, s-butoxy group, isobutoxy group, t-butoxy group, and the like;<br>a $C_{1-6}$ alkoxy group is preferable |
| Alkenyloxy groups | Vinyloxy group, allyloxy group, and the like;<br>a $C_{2-6}$ alkenyloxy group is preferable |
| Alkynyloxy groups | Ethynyloxy group, propargyloxy group, and the like;<br>a $C_{2-6}$ alkynyloxy group is preferable |
| Aryloxy groups | Phenoxy group, 1-naphthoxy group, and the like;<br>a $C_{6-10}$ aryloxy group is preferable |
| Arylalkyloxy groups | Benzyloxy group, phenethyloxy group, and the like;<br>a $C_{6-10}$ aryl $C_{1-6}$ alkyloxy group is preferable |
| Heterocyclic oxy groups | Pyridin-2-yloxy group, 3-oxazolin-2-yloxy group, pyrrolidin-2-yloxy group, and the like |
| Alkylthiocarbonyl groups | Methylthiocarbonyl group, ethylthiocarbonyl group, n-propylthiocarbonyl group, isopropylthiocarbonyl group, n-butylthiocarbonyl group, isobutylthiocarbonyl group, s-butylthicarbonyl group, t-butylthiocarbonyl group, and the like;<br>a $C_{1-6}$ alkylthiocarbonyl group is preferable |
| Alkoxycarbonyl groups | Methoxycarbonyl group, ethoxycarbonyl group, n-propoxycarbonyl group, isopropoxycarbonylamino group, n-butoxycarbonyl group, t-butoxycarbonyl group, and the like;<br>a $C_{1-6}$ alkoxycarbonyl group is preferable |
| Unsubstituted or substituted aminocarbonyl groups | Aminocarbonyl group, dimethylaminocarbonyl group, phenylaminocarbonyl group, and the like |
| unsubstituted or substituted hydrazino groups | Hydrazino group, N'-phenyl hydrazino group, N'-methoxycarbonyl hydrazino group, N'-acetyl hydrazino group, N'-methyl hydrazino group, and the like |
| Unsubstituted or substituted hydrazinocarbonyl groups | Hydrazinocarbonyl group, N'-methyl hydrazinocarbonyl group, N'-phenyl hydrazinocarbonyl group, and the like |
| Alkylthio groups | Methylthio group, ethylthio group, t-butylthio group, and the like;<br>a $C_{1-6}$ alkylthio group is preferable |
| Alkenylthio groups | Vinylthio group, allylthio group, and the like;<br>a $C_{2-6}$ alkenylthio group is preferable |
| Alkynylthio groups | Ethynylthio group, propargylthio group, and the like;<br>a $C_{2-6}$ alkynylthio group is preferable |
| Arylthio groups | Phenylthio group, 4-chlorophenylthio group, and the like;<br>a $C_{6-10}$ arylthio group is preferable |
| Heteroarylthio groups | Pyridin-2-ylthio group, pyridazin-3-ylthio group, and the like |
| Aryl alkylthio groups | Benzylthio group, phenethylthio group, and the like;<br>a $C_{6-10}$ aryl $C_{1-6}$ alkylthio group is preferable |
| Alkyl sulfonyl groups | Methyl sulfonyl group, ethyl sulfonyl group, t-butyl sulfonyl group, and the like;<br>a $C_{1-6}$ alkyl sulfonyl group is preferable |

TABLE 1-continued

Substituent Groups

| Substituent Type | Exemplifications |
| --- | --- |
| Alkenyl sulfonyl groups | Vinyl sulfonyl group, allyl sulfonyl group, and the like; a C2-6 alkenyl sulfonyl group is preferable |
| Alkynyl sulfonyl groups | Ethynyl sulfonyl group, propargyl sulfonyl group, and the like; a C2-6 alkynyl sulfonyl group is preferable |
| Aryl sulfonyl groups | Phenyl sulfonyl group, naphtyl sulfonyl group, and the like; a C6-10 aryl sulfonyl group is preferable |
| Heteroaryl sulfonyl groups | Pyridin-2-ylsulfonyl group, pyridin-3-ylsulfonyl group, and the like |
| Arylalkyl sulfonyl groups | Benzyl sulfonyl group, phenethyl sulfonyl group, and the like; a C6-10 aryl C1-6 alkylsulfonyl group is preferable |
| Acyl groups | Formyl group, acetyl group, propionyl group, acryloyl group, cinnamoyl group, benzoyl group, pyridin-2-ylcarbonyl group, cyclohexylcarbonyl group, and the like; a C1-10 acyl group is preferable |
| Acyloxy groups | Formyloxy group, acetyloxy group, propionyloxy group, cinnamoyloxy group, benzoyloxy group, pyridin-2-ylcarbonyloxy group, cyclohexylcarbonyloxy group, and the like; a C1-10 acyloxy group is preferable |
| Alkylene dioxy groups | Ethylene dioxy group, trimethylene dioxy group, tetramethylene dioxy group, and the like |

(Y)

Y indicates an alkyl group.

With respect to the "alkyl group" of Y, one may cite the same examples as the "alkyl group" of X mentioned above.

(Z)

Z indicates a respectively independent nitro group, hydroxyl group, mercapto group, halogen atom, group expressed by $N(R^a)_2$ (in the formula, each $R^a$ indicates a respectively independent hydrogen atom or hydrocarbon group), alkyl group, or cyano group.

Z is bonded in 0-3 units onto the benzene ring, and may also be bonded to A in the case where A is carbon atom.

As the "halogen atom" of Z, one may cite a fluorine atom, chlorine atom, bromine atom, iodine atom, and the like.

The "$N(R^a)_2$" of Z signifies an amino group or an amino group that is substituted with a hydrocarbon group.

The "hydrocarbon group" in $R^a$ indicates an alkyl group, cycloalkyl group, alkenyl group, cycloalkenyl group, alkynyl group, aryl group, arylalkyl group, and the like.

Here, with respect to the "alkyl group," "alkenyl group," "alkynyl group," and "aryl group" of $R^a$, one may cite the same examples as the "alkyl group," "alkenyl group," "alkynyl group," and "aryl group" of X mentioned above.

The "cycloalkyl group" of $R^a$ signifies an alkyl group that has a cyclic portion that is monocyclic or polycyclic, and one may cite a cyclopropyl group, cyclobutyl group, cyclopentyl group, cyclohexyl group, and the like. A C3-C8 cycloalkyl group is preferable.

The "cycloalkenyl group" of $R^a$ signifies an alkenyl group having a cyclic portion, and one may cite a cyclopropenyl group, 2-cyclobutenyl group, 3-cyclopentenyl group, and the like. A C3-8 cycloalkenyl group is preferable.

As an "arylalkyl group" of $R^a$, one may cite a benzyl group, phenethyl group, 3-phenyl-n-propyl group, 1-phenyl-n-hexyl group, naphthalene-1-ylmethyl group, naphthalene-2-ylethyl group, 1-naphthalene-2-yl-n-propyl group, indene-1-ylmethyl group, and the like. A (C6-10) aryl (C1-6) alkyl group is preferable.

As specific examples of a $N(R^a)_2$ group, one may cite an amino group, dimethyl amino group, methylethyl amino group, vinyl amino group, allyl amino group, phenyl amino group, benzyl amino group, and the like. The $N(R^a)_2$ group may have at least one substituent of at least a single type selected from among the substituent groups shown in the aforementioned Table 1.

With respect to the "alkyl group" of Z, one may cite the same examples as the "alkyl group" of X mentioned above.

(A)

A indicates carbon atom or nitrogen atom, and hydrogen atom is bonded thereto in the case where the carbon atom is not substituted with Z.

(D)

D indicates oxygen atom, a C(O) group, a group expressed by the following formula

[Chemical Formula 5]

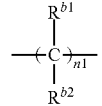

(in the formula, $R^{b1}$ and $R^{b2}$ indicate hydrogen atoms or organic groups that are respectively independent; n1 indicates 1 or 2), or a group expressed by $N(R^c)$ (in the formula, $R^c$ indicates hydrogen atom or hydrocarbon group).

$R^{b1}$ and $R^{b2}$ are hydrogen atoms or organic groups. Here, "organic groups" signify the totality of functional groups including carbon atoms.

As "organic groups" of $R^{b1}$ and $R^{b2}$, one may cite a cyano group, alkyl group, alkenyl group, alkynyl group, alkoxy group, cycloalkyl group, cycloalkenyl group, aryl group, aryloxy group, acyl group, alkoxy carbonyl group, alkylthio carbonyl group, alkylthio group, alkyl sulfinyl group, alkyl sulfonyl group, arylthio group, aryl sulfinyl group, aryl sulfonyl group, and the like. Any of the groups other than a "cyano group" may have substituents.

The definitions for each of the aforementioned organic groups are as follows.

With respect to the "alkyl group," "alkenyl group," "alkynyl group," "cycloalkyl group," "cycloalkenyl group," and "aryl group" of $R^{b1}$ and $R^{b2}$, one may cite the same specific examples of each group mentioned above.

As an "alkoxy group" of $R^{b1}$ and $R^{b2}$, one may cite a methoxy group, ethoxy group, n-propoxy group, i-propoxy group, n-butoxy group, i-butoxy group, s-butoxy group, t-butoxy group, n-pentyloxy group, n-hexyloxy group, and the like. A C1-6 alkoxy group is preferable. The alkoxy group may have at least one substituent of at least a single type selected from among the substituent groups shown in Table 1.

As an "aryloxy group" of $R^{b1}$ and $R^{b2}$, one may cite a phenoxy group, 1-naphtyloxy group, 2-naphtyloxy group, azulenyloxy group, indenyloxy group, indanyloxy group, tetralinyloxy group, and the like. A C6-14 aryloxy group is preferable. The aryloxy group may have at least one substituent of at least a single type selected from among the substituent groups shown in Table 1.

The "acyl group" of $R^{b1}$ and $R^{b2}$ signifies a group wherein hydrogen atom, or an alkyl group, alkenyl group, alkynyl group, aryl group, or heteroaryl group or the like is bonded with a carbonyl group. For example, one may cite:
a formyl group;
an alkyl carbonyl group such as an acetyl group, propionyl group, butyroyl group, pentanoyl group, hexanoyl group, heptanoyl group, octanoyl group, nonanoyl group, decanoyl group, 3-methylnonanoyl group, 8-methylnonanoyl group, 3-ethyloctanoyl group, 3,7-dimethyloctanoyl group, undecanoyl group, dodecanoyl group, tridecanoyl group, tetradecanoyl group, pentadecanoyl group, hexadecanoyl group, 1-methylpentadecanoyl group, 14-methylpentadecanoyl group, 13,13-dimethyltetradecanoyl group, heptadecanoyl group, 15-methylhexadecanoyl group, octadecanoyl group, 1-methylheptadecanoyl group, nonadecanoyl group, eicosanoyl group, heneicosanoyl group, and the like (a C2-6 alkyl carbonyl group is preferable);
an alkenyl carbonyl group such as an acryloyl group or allyl carbonyl group (a C3-6 alkenyl carbonyl group is preferable);
an alkynyl carbonyl group such as an ethynyl carbonyl group or 2-propionyl carbonyl group (a C3-6 alkynyl carbonyl group is preferable);
a cycloalkyl carbonyl group such as a cyclopropyl carbonyl group or cyclopentyl carbonyl group (a C4-7 cycloalkyl carbonyl group is preferable);
an aryl carbonyl group such as a benzoyl group, naphthyl carbonyl group, biphenyl carbonyl group, or anthranyl carbonyl group (a C7-15 aryl carbonyl group is preferable);
a heteroaryl carbonyl group such as a 2-pyridyl carbonyl group or 2-thienyl carbonyl group (a C7-15 heteroaryl carbonyl group is preferable). The acyl group may have at least one substituent of at least a single type selected from among the substituent groups shown in Table 1.

As an "alkoxy carbonyl group" of $R^{b1}$ and $R^{b2}$, one may cite a methoxy carbonyl group, ethoxy carbonyl group, n-propoxy carbonyl group, i-propoxy carbonyl group, n-butoxy carbonyl group, i-butoxy carbonyl group, s-butoxy carbonyl group, t-butoxy carbonyl group, n-pentyloxy carbonyl group, n-hexyloxy carbonyl group, and the like. A C2-6 alkoxy carbonyl group is preferable. The alkoxy carbonyl group may have at least one substituent of at least a single type selected from among the substituent groups shown in Table 1.

As an "alkylthio carbonyl group" of $R^{b1}$ and $R^{b2}$, one may cite a methylthio carbonyl group, ethylthio carbonyl group, n-propylthio carbonyl group, i-propylthio carbonyl group, n-butylthio carbonyl group, i-butylthio carbonyl group, s-butylthio carbonyl group, t-butylthio carbonyl group, n-pentylthio carbonyl group, n-hexylthio carbonyl group, and the like. A C2-6 alkylthio carbonyl group is preferable. The alkylthio carbonyl group may have at least one substituent of at least a single type selected from among the substituent groups shown in Table 1.

As an "alkylthio group" of $R^{b1}$ and $R^{b2}$, one may cite a methylthio group, ethylthio group, n-propylthio group, i-propylthio group, n-butylthio group, i-butylthio group, s-butylthio group, t-butylthio group, and the like. A C1-6 alkylthio group is preferable.

As an "alkyl sulfinyl group" of $R^{b1}$ and $R^{b2}$, one may cite a methyl sulfinyl group, ethyl sulfinyl group, n-propyl sulfinyl group, i-propyl sulfinyl group, n-butyl sulfinyl group, i-butyl sulfinyl group, s-butyl sulfinyl group, t-butyl sulfinyl group, and the like. A C1-6 alkyl sulfinyl group is preferable. The alkyl sulfinyl group may have at least one substituent of at least a single type selected from among the substituent groups shown in Table 1.

As an "alkyl sulfonyl group" of $R^{b1}$ and $R^{b2}$, one may cite a methyl sulfonyl group, ethyl sulfonyl group, n-propyl sulfonyl group, i-propyl sulfonyl group, n-butyl sulfonyl group, i-butyl sulfonyl group, s-butyl sulfonyl group, t-butyl sulfonyl group, and the like. A C1-6 alkyl sulfonyl group is preferable. The alkyl sulfonyl group may have at least one substituent of at least a single type selected from among the substituent groups shown in Table 1.

As an "arylthio group" of $R^{b1}$ and $R^{b2}$, one may cite a phenylthio group, 1-naphtylthio group, 2-naphtylthio group, and the like. A C6-14 arylthio group is preferable. The arylthio group may have at least one substituent of at least a single type selected from among the substituent groups shown in Table 1.

As an "aryl sulfinyl group" of $R^{b1}$ and $R^{b2}$, one may cite a phenyl sulfinyl group, 1-naphtyl sulfinyl group, 2-naphtyl sulfinyl group, and the like. A C6-14 aryl sulfinyl group is preferable. The aryl sulfinyl group may have at least one substituent of at least a single type selected from among the substituent groups shown in Table 1.

As an "aryl sulfonyl group" of $R^{b1}$ and $R^{b2}$, one may cite a phenyl sulfonyl group, 1-naphtyl sulfonyl group, 2-naphtyl sulfonyl group, and the like. A C6-14 aryl sulfonyl group is preferable. The aryl sulfonyl group may have at least one substituent of at least a single type selected from among the substituent groups shown in Table 1.

As a group expressed by the following formula,

[Chemical Formula 6]

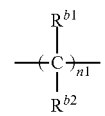

one may specifically cite —$CH_2$—, —$CH(CH_3)$—, —$CH(CF_3)$—, —$CH(C_2H_5)$—, —$CH(i-C_3H_7)$—, —$C(CH_3)_2$—, —$CH(c-C_3H_7)$—, —$CH(Phenyl)$-, —$CH(OCH_3)$—, —$CH(Acetyl)$-, —$CH(SCH_3)$—, —$(CH_2)_2$—, —$CH_2CH(CH_3)$—, —$CH_2C(CH_3)_2$—, and the like.

The $R^c$ in the $N(R^c)$ group of D is hydrogen atom or a hydrocarbon group, and with respect to the hydrocarbon group, one may cite the same examples of hydrocarbon groups as mentioned in Z above.

As the $N(R^c)$ group of D, one may specifically cite —NH—, —$N(CH_3)$—, —$N(CF_3)$—, —$N(C_2H_5)$—, —$N(i-C_3H_7)$—, —$N(c-C_3H_7)$—, and the like.

(W)

W indicates hydrogen atom, halogen atom, cyano group, nitro group, alkyl group, alkoxy group, $N(R^d)_2$ group (in the formula, each $R^d$ indicates a respectively independent hydrogen atom or hydrocarbon group), alkylthio group, alkylsulfinyl group, alkylsulfonyl group, or heteroaryl group.

With respect to the "alkyl group," "alkoxy group," "alkylthio group," "alkyl sulfinyl group," "alkyl sulfonyl group," and "heteroaryl group" of W, one may cite the same examples of each group mentioned above.

In the $N(R^d)_2$ of W, each $R^d$ indicates a respectively independent hydrogen atom or hydrocarbon group, and with respect to hydrocarbon groups, one may cite the same examples of hydrocarbon groups as mentioned in Z above.

As specific examples of the $N(R^d)_2$ group of W, one may cite an amino group, dimethyl amino group, methylethyl amino group, vinyl amino group, allyl amino group, phenyl amino group, benzyl amino group, and the like. The $N(R^d)_2$ group may have at least one substituent of at least a single type selected from among the substituent groups shown in Table 1.

(R¹ and R²)

R¹ and R² indicate a respectively independent hydrogen atom, acyl group, or alkoxy carbonyl group, As the "acyl group" and "alkoxy carbonyl group" of R¹ and R², one may cite the same examples of each group mentioned above.

Moreover, R¹ and R² may be bonded, and may form a heterocycle together with nitrogen atom between R¹ and R². As a heterocycle, one may cite a monocycle or a condensed cycle with a benzene ring, and, for example,

[Chemical formula 7]

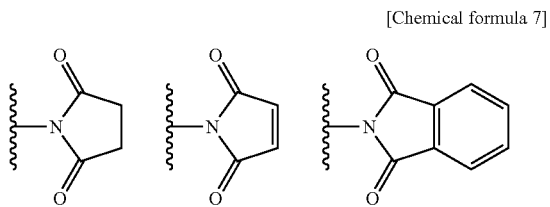

may be cited.

PREFERRED EXAMPLES

As compounds of the present invention, from the standpoint of superior biocontrol activity, a compound expressed by the following formula (XVI), wherein R¹ represents hydrogen atom and R² represents an optionally substituted acyl group or an optionally substituted alkoxy carbonyl group is preferable.

[Chemical formula 8]

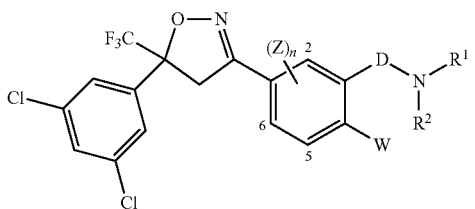

(XVI)

(in the formula, Z, D, W, and n have the same meanings described above).

As a salt of the compounds expressed in formula (I), there are no particular limitations provided that it is horticulturally permissible. For example, one may cite salts of inorganic acid such as hydrochloride salt, nitrate salt, sulfate salt, and phosphate salt, as well as salts of organic acid such as acetic acid, propionic acid, and lactic acid.

In addition, in the compounds (I) of the present invention, there may exist stereoisomers or tautomers based on asymmetric carbon, double bonds and the like. Such isomers and their mixtures are all included within the technical scope of the present invention.

The structure of the compounds of the present invention may be determined by NMR spectroscopy, IR spectroscopy, MS spectroscopy, and the like.

EXAMPLES OF COMPOUNDS OF THE PRESENT INVENTION

Representative examples of the compounds of the present invention are shown in the following table. However, the compounds of the present invention are not limited to these compounds.

The abbreviations in the table express the following meanings.

Me: methyl, Et: ethyl, Pr: propyl, Bt: butyl, Hex: hexyl, Ph: phenyl, n: normal, i: iso, t: tertiary, c: cyclo, $CH_3C(OCH_2CH_2O)CH_2C(O)$: 3,3-ethylenedioxy-butylyl Examples of Compounds (1)

[Chemical formula 9]

TABLE 2

Examples of compounds (1)

| No. | Y  | X          | (Z)n | W  | Rb1, Rb2 | R1 | R2 |
|-----|----|-----------|----|----|---------|----|----|
| 1   | Me | Me         | —  | H  | H, H    | H  | H  |
| 2   | Me | Et         | —  | H  | H, H    | H  | MeC(O) |
| 3   | Me | i-Pr       | —  | H  | H, H    | H  | EtC(O) |
| 4   | Me | t-Bt       | —  | H  | H, H    | H  | c-PrC(O) |
| 5   | Me | $CF_3$     | —  | H  | H, H    | H  | PhC(O) |
| 6   | Me | Ph         | —  | H  | H, H    | H  | $CH_3CH(OMe)CH_2C(O)$ |
| 7   | Me | 3,5-diCl—Ph| —  | H  | H, H    | H  | $N=CCH_2CH_2C(O)$ |
| 8   | Me | CH2=CH     | —  | H  | H, H    | H  | $CH_3C(OCH_2CH_2O)CH_2C(O)$ |
| 9   | Me | CH≡C       | —  | H  | H, H    | H  | MeOC(O) |
| 10  | Me | 2-furyl    | —  | H  | H, H    | H  | i-PrOC(O) |
| 11  | Me | 2-pyridyl  | —  | H  | H, H    | H  | t-BtOC(O) |
| 12  | Me | Me         | —  | Cl | H, H    | H  | H  |
| 13  | Me | Et         | —  | Cl | H, H    | H  | MeC(O) |
| 14  | Me | i-Pr       | —  | Cl | H, H    | H  | EtC(O) |
| 15  | Me | t-Bt       | —  | Cl | H, H    | H  | c-PrC(O) |
| 16  | Me | $CF_3$     | —  | Cl | H, H    | H  | PhC(O) |
| 17  | Me | Ph         | Me | Br | H, H    | H  | $CH_3CH(OMe)CH_2C(O)$ |
| 18  | Me | 3,5-diCl—Ph| —  | Br | H, H    | H  | $N=CCH_2CH_2C(O)$ |

TABLE 2-continued

Examples of compounds (1)

| No. | Y | X | (Z)n | W | Rb1, Rb2 | R1 | R2 |
|---|---|---|---|---|---|---|---|
| 19 | Me | CH2=CH | — | I | H, H | H | CH2C(OCH2CH2O)CH2C(O) |
| 20 | Et | CH≡C | — | I | H, H | H | CH2OC(O) |
| 21 | Et | 2-furyl | — | F | H, H | H | i-PrOC(O) |
| 22 | Et | 2-pyridyl | — | F | H, H | H | t-BtOC(O) |
| 23 | Et | Me | — | CN | H, H | H | H |
| 24 | Et | Et | — | CN | H, H | H | MeC(O) |
| 25 | Et | i-Pr | — | NO2 | H, H | H | EtC(O) |
| 26 | Et | t-Bt | — | NO2 | H, H | H | c-PrC(O) |
| 27 | Et | CF3 | — | CH3 | H, H | H | PhC(O) |
| 28 | Et | Ph | — | CH3 | H, H | H | CH3CH(OMe)CH2C(O) |
| 29 | Et | 3,5-diCl—Ph | — | CF3 | H, H | H | N≡CCH2CH2C(O) |
| 30 | Et | CH2=CH | — | CF3 | H, H | H | CH3COCH2CH2O)CH2O(O) |
| 31 | Et | CH≡C | — | MeO | H, H | H | MeOC(O) |
| 32 | Et | 2-furyl | — | MeO | H, H | H | i-PrOC(O) |
| 33 | Et | 2-pyridyl | — | NH2 | H, H | H | t-BtOC(O) |
| 34 | Et | Me | — | NH2 | H, H | H | H |
| 35 | Et | Et | — | N(Me)2 | H, H | H | MeC(O) |
| 36 | Et | i-Pr | — | N(Me)2 | H, H | H | EtC(O) |
| 37 | Et | t-Bt | — | MeS | H, H | H | c-PrC(O) |
| 38 | Et | CF3 | — | MeS | H, H | H | PhC(O) |
| 39 | i-Pr | Ph | — | MeS(O) | H, H | H | CH3CH(OMe)CH2C(O) |
| 40 | i-Pr | 3,5-diCl—Ph | — | MeS(O) | H, H | H | N≡CCH2CH2C(O) |
| 41 | i-Pr | CH2=CH | — | MeS(O)2 | H, H | H | CH3C(OCH2CH2O)CH2C(O) |
| 42 | i-Pr | CH≡C | — | MeS(O)2 | H, H | H | CH3OC(O) |
| 43 | i-Pr | 2-furyl | — | 2-furyl | H, H | H | i-PrOC(O) |
| 44 | i-Pr | 2-pyridyl | — | 2-pyridyl | H, H | H | t-BtOC(O) |
| 45 | i-Pr | Me | — | Cl | H, H | H | H |
| 46 | i-Pr | Et | — | Cl | H, H | MeC(O) | MeC(O) |
| 47 | i-Pr | i-Pr | — | Cl | H, H | EtC(O) | EtC(O) |
| 48 | i-Pr | t-Bt | — | Cl | H, H | c-PrC(O) | c-PrC(O) |
| 49 | i-Pr | CF3 | — | Cl | H, H | PhC(O) | PhC(O) |
| 50 | i-Pr | Ph | — | Cl | H, H | H | CH3CH(OMe)CH2C(O) |
| 51 | CF3 | 3,5-diCl—Ph | 2-Cl | H | H, H | H | N≡CCH2CH2C(O) |
| 52 | CF3 | 3,5-diCl—Ph | 5-Cl | H | H, Me | H | CH3C(OCH2CH2O)CH2C(O) |
| 53 | CF3 | 3,5-diCl—Ph | 6-Cl | H | H, Et | H | CH3OC(O) |
| 54 | CF3 | 3,5-diCl—Ph | 2-Br | H | Me, Me | H | i-PrOC(O) |
| 55 | CF3 | 3,5-diCl—Ph | 5-Br | H | H, H | H | t-BtOC(O) |
| 56 | CF3 | 3,5-diCl—Ph | 6-Br | H | H, Me | H | H |
| 57 | CF3 | 3,5-diCl—Ph | 2-I | H | H, Et | H | MeC(O) |
| 58 | CF3 | 3,5-diCl—Ph | 5-I | H | Me, Me | H | EtC(O) |
| 59 | CF3 | 3,5-diCl—Ph | 6-I | H | H, H | H | c-PrC(O) |
| 60 | CF3 | 3,5-diCl—Ph | 2-F | H | H, Me | H | PhC(O) |
| 61 | CF3 | 3,5-diCl—Ph | 5-F | H | H, Et | H | CH3CH(OMe)CH2C(O) |
| 62 | CF3 | 3,5-diCl—Ph | 6-F | H | Me, Me | H | N≡CCH2CH2C(O) |
| 63 | CF3 | 3,5-diCl—Ph | 2-OH | H | H, H | H | CH3C(OCH2CH2O)CH2C(O) |
| 64 | CF3 | 3,5-diCl—Ph | 5-OH | H | H, Me | H | CH3OC(O) |
| 65 | CF3 | 3,5-diCl—Ph | 6-OH | H | H, Et | H | i-PrOC(O) |
| 66 | CF3 | 3,5-diCl—Ph | 2-SH | H | Me, Me | H | t-BtOC(O) |
| 67 | CF3 | 3,5-diCl—Ph | 5-SH | H | H, H | H | H |
| 68 | CF3 | 3,5-diCl—Ph | 6-SH | H | H, Me | H | MeC(O) |
| 69 | CF3 | 3,5-diCl—Ph | 2-NH | H | H, Et | H | EtC(O) |
| 70 | CF3 | 3,5-diCl—Ph | 5-NH | H | Me, Me | H | c-PrC(O) |
| 71 | CF3 | 3,5-diCl—Ph | 6-NH | H | H, H | H | PhC(O) |
| 72 | CF3 | 3,5-diCl—Ph | 2-N(Me) | H | H, Me | H | CH3CH OMe)CH2C(O) |
| 73 | CF3 | 3,5-diCl—Ph | 5-N(Me) | Cl | H, H | H | N≡CCH2CH2C(O) |
| 74 | CF3 | 3,5-diCl—Ph | 6-N(Me) | Cl | H, CF3 | H | CH3C(OCH2CH2O)CH2C(O) |
| 75 | CF3 | 3,5-diCl—Ph | 2-NO2 | Cl | H, Et | H | CH3OC(O) |
| 76 | CF3 | 3,5-diCl—Ph | 5-NO2 | Cl | Me, Me | H | i-PrOC(O) |
| 77 | CF3 | 3,5-diCl—Ph | 6-NO2 | Br | H, H | H | t-BtOC(O) |
| 78 | CF3 | 3,5-diCl—Ph | 2-CN | Br | H, CF3 | H | H |
| 79 | CF3 | 3,5-diCl—Ph | 5-CN | I | H, Et | H | MeC(O) |
| 80 | CF3 | 3,5-diCl—Ph | 6-CN | I | Me, Me | H | EtC(O) |
| 81 | CF3 | 3,5-diCl—Ph | 2-Cl | F | H, H | H | c-PrC(O) |
| 82 | CF3 | 3,5-diCl—Ph | 5-Cl | F | H, Me | H | PhC(O) |
| 83 | CF3 | 3,5-diCl—Ph | 6-Cl | NO2 | H, Et | H | CH3CH(OMe)CH2C(O) |
| 84 | CF3 | 3,5-diCl—Ph | 2-Br | NO2 | Me, Me | H | N≡CCH2CH2C(O) |
| 85 | CF3 | 3,5-diCl—Ph | 5-Br | OH | H, H | H | CH3C(OCH2CH2O)CH2C(O) |
| 86 | CF3 | 3,5-diCl—Ph | 6-Br | OH | H, Me | H | CH3OC(O) |
| 87 | CF3 | 3,5-diCl—Ph | 2-I | SH | H, Et | H | i-PrOC(O) |
| 88 | CF3 | 3,5-diCl—Ph | 5-I | SH | Me, Me | H | t-BtOC(O) |
| 89 | CF3 | 3,5-diCl—Ph | 6-I | NH | H, H | H | H |
| 90 | CF3 | 3,5-diCl—Ph | 2-F | NH | H, Me | H | MeC(O) |
| 91 | CF3 | 3,5-diCl—Ph | 5-F | N(Me) | H, Et | H | EtC(O) |
| 92 | CF3 | 3,5-diCl—Ph | 6-F | N(Me) | Me, Me | H | c-PrC(O) |
| 93 | CF3 | 3,5-diCl—Ph | 2-OH | CN | H, H | H | PhC(O) |
| 94 | CF3 | 3,5-diCl—Ph | 5-OH | CN | H, Me | H | CH3CH(OMe)CH2C(O) |

TABLE 2-continued

Examples of compounds (1)

| No. | Y | X | (Z)n | W | Rb1, Rb2 | R1 | R2 |
|---|---|---|---|---|---|---|---|
| 95 | $CF_3$ | 3,5-diCl—Ph | 6-OH | H | H, Ph | H | N≡CCH$_2$CH$_2$C(O) |
| 96 | $CF_3$ | 3,5-diCl—Ph | 2-Cl | H | H, i-Pr | H | CH$_3$C(OCH$_2$CH$_2$O)CH$_2$C(O) |
| 97 | $CF_3$ | 3,5-diCl—Ph | 5-Cl | H | H, c-Pr | H | CH$_3$OC(O) |
| 98 | $CF_3$ | 3,5-diCl—Ph | 2-Br | H | H, $CF_3$ | H | i-PrOC(O) |
| 99 | $CF_3$ | 3,5-diCl—Ph | 5-Br | H | $CF_3$, $CF_3$ | H | t-BtOC(O) |
| 100 | $CF_3$ | 3,5-diCl—Ph | 2-Cl | H | Et, Et | H | H |

Examples of Compounds (2)

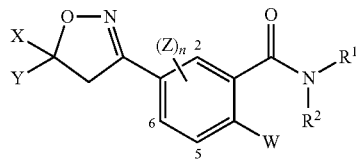

[Chemical formula 10]

TABLE 3

Examples of compounds (2)

| No. | Y | X | (Z)n | W | R1 | R2 |
|---|---|---|---|---|---|---|
| 1 | Me | Me | — | H | H | H |
| 2 | Me | Et | — | H | H | MeC(O) |
| 3 | Me | i-Pr | — | H | H | EtC(O) |
| 4 | Me | t-Bt | — | H | H | c-PrC(O) |
| 5 | Me | $CF_3$ | — | H | H | PhC(O) |
| 6 | Me | Ph | — | H | H | CH$_3$CH(OMe)CH$_2$C(O) |
| 7 | Me | 3,5-diCl—Ph | — | H | H | N≡CCH$_2$CH$_2$C(O) |
| 8 | Me | CH2=CH | — | H | H | CH$_3$C(OCH$_2$CH$_2$O)CH$_2$C(O) |
| 9 | Me | CH≡C | — | H | H | MeOC(O) |
| 10 | Me | 2-furyl | — | H | H | i-PrOC(O) |
| 11 | Me | 2-pyridyl | — | H | H | t-BtOC(O) |
| 12 | Me | Me | — | Cl | H | H |
| 13 | Me | Et | — | Cl | H | MeC(O) |
| 14 | Me | i-Pr | — | Cl | H | EtC(O) |
| 15 | Me | t-Bt | — | Cl | H | c-PrC(O) |
| 16 | Me | $CF_3$ | — | Cl | H | PhC(O) |
| 17 | Me | Ph | — | Br | H | CH$_3$CH(OMe)CH$_2$C(O) |
| 18 | Me | 3,5-diCl—Ph | — | Br | H | N≡CCH$_2$CH$_2$C(O) |
| 19 | Me | CH2=CH | — | I | H | CH$_3$C(OCH$_2$CH$_2$O)CH$_2$C(O) |
| 20 | Et | CH≡C | — | I | H | CH$_3$OC(O) |
| 21 | Et | 2-furyl | — | F | H | i-PrOC(O) |
| 22 | Et | 2-pyridyl | — | F | H | t-BtOC(O) |
| 23 | Et | Me | — | CN | H | H |
| 24 | Et | Et | — | CN | H | MeC(O) |
| 25 | Et | i-Pr | — | $NO_2$ | H | EtC(O) |
| 26 | Et | t-Bt | — | $NO_2$ | H | c-PrC(O) |
| 27 | Et | $CF_3$ | — | $CH_3$ | H | PhC(O) |
| 28 | Et | Ph | — | $CH_3$ | H | CH$_3$CH(OMe)CH$_2$C(O) |
| 29 | Et | 3,5-diCl—Ph | — | $CF_3$ | H | N≡CCH$_2$CH$_2$C(O) |
| 30 | Et | CH2=CH | — | $CF_3$ | H | CH$_3$C(OCH$_2$CH$_2$O)CH$_2$C(O) |
| 31 | Et | CH≡C | — | MeO | H | MeOC(O) |
| 32 | Et | 2-furyl | — | MeO | H | i-PrOC(O) |
| 33 | Et | 2-pyridyl | — | $NH_2$ | H | t-BtOC(O) |
| 34 | Et | Me | — | $NH_2$ | H | H |
| 35 | Et | Et | — | $N(Me)_2$ | H | MeC(O) |
| 36 | Et | i-Pr | — | $N(Me)_2$ | H | EtC(O) |
| 37 | Et | t-Bt | — | MeS | H | c-PrC(O) |
| 38 | Et | $CF_3$ | — | MeS | H | PhC(O) |
| 39 | i-Pr | Ph | — | MeS(O) | H | CH$_3$CH(OMe)CH$_2$C(O) |
| 40 | i-Pr | 3,5-diCl—Ph | — | MeS(O) | H | N≡CCH$_2$CH$_2$C(O) |
| 41 | i-Pr | CH2=CH | — | MeS(O)$_2$ | H | CH$_3$C(OCH$_2$CH$_2$O)CH$_2$C(O) |
| 41 | i-Pr | CH≡C | — | MeS(O)$_2$ | H | CH$_3$OC(O) |
| 43 | i-Pr | 2-furyl | — | 2-furyl | H | i-PrOC(O) |
| 44 | i-Pr | 2-pyridyl | — | 2-pyridyl | H | t-BtOC(O) |

TABLE 3-continued

Examples of compounds (2)

| No. | Y | X | (Z)n | W | R1 | R2 |
|---|---|---|---|---|---|---|
| 45 | i-Pr | Me | — | Cl | H | H |
| 46 | i-Pr | Et | — | Cl | MeC(O) | MeC(O) |
| 47 | i-Pr | i-Pr | — | Cl | EtC(O) | EtC(O) |
| 48 | i-Pr | t-Bt | — | Cl | c-PrC(O) | c-PrC(O) |
| 49 | i-Pr | $CF_3$ | — | Cl | PhC(O) | PhC(O) |
| 50 | i-Pr | Ph | — | Cl | H | $CH_3CH(OMe)CH_2C(O)$ |
| 51 | $CF_3$ | 3,5-diCl—Ph | 2-Cl | H | H | $N{\equiv}CCH_2CH_2C(O)$ |
| 52 | $CF_3$ | 3,5-diCl—Ph | 5-Cl | H | H | $CH_3C(OCH_2CH_2O)CH_2C(O)$ |
| 53 | $CF_3$ | 3,5-diCl—Ph | 6-Cl | H | H | $CH_3OC(O)$ |
| 54 | $CF_3$ | 3,5-diCl—Ph | 2-Br | H | H | i-PrOC(O) |
| 55 | $CF_3$ | 3,5-diCl—Ph | 5-Br | H | H | t-BtOC(O) |
| 56 | $CF_3$ | 3,5-diCl—Ph | 6-Br | H | H | H |
| 57 | $CF_3$ | 3,5-diCl—Ph | 2-I | H | H | MeC(O) |
| 58 | $CF_3$ | 3,5-diCl—Ph | 5-I | H | H | EtC(O) |
| 59 | $CF_3$ | 3,5-diCl—Ph | 6-I | H | H | c-PrC(O) |
| 60 | $CF_3$ | 3,5-diCl—Ph | 2-F | H | H | PhC(O) |
| 61 | $CF_3$ | 3,5-diCl—Ph | 5-F | H | H | $CH_3CH(OMe)CH_2C(O)$ |
| 62 | $CF_3$ | 3,5-diCl—Ph | 6-F | H | H | $N{\equiv}CCH_2CH_2C(O)$ |
| 63 | $CF_3$ | 3,5-diCl—Ph | 2-$NO_2$ | H | H | $CH_3C(OCH_2CH_2O)CH_2C(O)$ |
| 64 | $CF_3$ | 3,5-diCl—Ph | 5-$NO_2$ | H | H | $CH_3OC(O)$ |
| 65 | $CF_3$ | 3,5-diCl—Ph | 6-$NO_2$ | H | H | i-PrOC(O) |
| 66 | $CF_3$ | 3,5-diCl—Ph | 2-OH | H | H | t-BtOC(O) |
| 67 | $CF_3$ | 3,5-diCl—Ph | 5-OH | H | H | H |
| 68 | $CF_3$ | 3,5-diCl—Ph | 6-OH | H | H | MeC(O) |
| 69 | $CF_3$ | 3,5-diCl—Ph | 2-SH | H | H | EtC(O) |
| 70 | $CF_3$ | 3,5-diCl—Ph | 5-SH | H | H | c-PrC(O) |
| 71 | $CF_3$ | 3,5-diCl—Ph | 6-SH | H | H | PhC(O) |
| 72 | $CF_3$ | 3,5-diCl—Ph | 2-NH | H | H | $CH_3CH(OMe)CH_2C(O)$ |
| 73 | $CF_3$ | 3,5-diCl—Ph | 5-NH | Cl | H | $N{\equiv}CCH_2CH_2C(O)$ |
| 74 | $CF_3$ | 3,5-diCl—Ph | 6-NH | Cl | H | $CH_3C(OCH_2CH_2O)CH_2C(O)$ |
| 75 | $CF_3$ | 3,5-diCl—Ph | 2-N(Me) | Cl | H | $CH_3OC(O)$ |
| 76 | $CF_3$ | 3,5-diCl—Ph | 5-N(Me) | Cl | H | i-PrOC(O) |
| 77 | $CF_3$ | 3,5-diCl—Ph | 6-N(Me) | Br | H | t-BtOC(O) |
| 78 | $CF_3$ | 3,5-diCl—Ph | 2-CN | Br | H | H |
| 79 | $CF_3$ | 3,5-diCl—Ph | 5-CN | I | H | MeC(O) |
| 80 | $CF_3$ | 3,5-diCl—Ph | 6-CN | I | H | EtC(O) |
| 81 | $CF_3$ | 3,5-diCl—Ph | 2-Cl | F | H | c-PrC(O) |
| 82 | $CF_3$ | 3,5-diCl—Ph | 5-Cl | F | H | PhC(O) |
| 83 | $CF_3$ | 3,5-diCl—Ph | 6-Cl | $NO_2$ | H | $CH_3CH(OMe)CH_2C(O)$ |
| 84 | $CF_3$ | 3,5-diCl—Ph | 2-Br | $NO_2$ | H | $N{\equiv}CCH_2CH_2C(O)$ |
| 85 | $CF_3$ | 3,5-diCl—Ph | 5-Br | OH | H | $CH_3C(OCH_2CH_2O)CH_2C(O)$ |
| 86 | $CF_3$ | 3,5-diCl—Ph | 6-Br | OH | H | $CH_3OC(O)$ |
| 87 | $CF_3$ | 3,5-diCl—Ph | 2-I | SH | H | i-PrOC(O) |
| 88 | $CF_3$ | 3,5-diCl—Ph | 5-I | SH | H | t-BtOC(O) |
| 89 | $CF_3$ | 3,5-diCl—Ph | 6-I | NH | H | H |
| 90 | $CF_3$ | 3,5-diCl—Ph | 2-F | NH | H | MeC(O) |
| 91 | $CF_3$ | 3,5-diCl—Ph | 5-F | N(Me) | H | EtC(O) |
| 92 | $CF_3$ | 3,5-diCl—Ph | 6-F | N(Me) | H | c-PrC(O) |
| 93 | $CF_3$ | 3,5-diCl—Ph | 2-OH | CN | H | PhC(O) |
| 94 | $CF_3$ | 3,5-diCl—Ph | 5-OH | CN | H | $CH_3CH(OMe)CH_2C(O)$ |
| 95 | $CF_3$ | 3,5-diCl—Ph | 6-OH | H | H | $N{\equiv}CCH_2CH_2C(O)$ |
| 96 | $CF_3$ | 3,5-diCl—Ph | 2-Cl | H | H | $CH_3C(OCH_2CH_2O)CH_2C(O)$ |
| 97 | $CF_3$ | 3,5-diCl—Ph | 5-Cl | H | H | $CH_3OC(O)$ |
| 98 | $CF_3$ | 3,5-diCl—Ph | 2-Br | H | H | i-PrOC(O) |
| 99 | $CF_3$ | 3,5-diCl—Ph | 5-Br | H | H | t-BtOC(O) |
| 100 | $CF_3$ | 3,5-diCl—Ph | 2-Cl | H | H | H |

Examples of Compounds (3)

[Chemical formula 11]

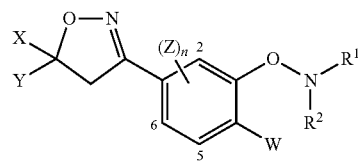

TABLE 4

Examples of compounds (3)

| No. | Y | X | (Z)n | W | R1 | R2 |
|---|---|---|---|---|---|---|
| 1 | Me | Me | — | H | H | H |
| 2 | Me | Et | — | H | H | MeC(O) |
| 3 | Me | i-Pr | — | H | H | EtC(O) |
| 4 | Me | t-Bt | — | H | H | c-PrC(O) |
| 5 | Me | CF$_3$ | — | H | H | PhC(O) |
| 6 | Me | Ph | — | H | H | CH$_3$CH(OMe)CH$_2$C(O) |
| 7 | Me | 3,5-diCl—Ph | — | H | H | N≡CCH$_2$CH$_2$C(O) |
| 8 | Me | CH2=CH | — | H | H | CH$_3$C(OCH$_2$CH$_2$O)CH$_2$C(O) |
| 9 | Me | CH≡C | — | H | H | MeOC(O) |
| 10 | Me | 2-furyl | — | H | H | i-PrOC(O) |
| 11 | Me | 2-pyridyl | — | H | H | t-BtOC(O) |
| 12 | Me | Me | — | Cl | H | H |
| 13 | Me | Et | — | Cl | H | MeC(O) |
| 14 | Me | i-Pr | — | Cl | H | EtC(O) |
| 15 | Me | t-Bt | — | Cl | H | c-PrC(O) |
| 16 | Me | CF$_3$ | — | Cl | H | PhC(O) |
| 17 | Me | Ph | — | Br | H | CH$_3$CH(OMe)CH$_2$C(O) |
| 18 | Me | 3,5-diCl—Ph | — | Br | H | N≡CCH$_2$CH$_2$C(O) |
| 19 | Me | CH2=CH | — | I | H | CH$_3$C(OCH$_2$CH$_2$O)CH$_2$C(O) |
| 20 | Et | CH≡C | — | I | H | CH$_3$OC(O) |
| 21 | Et | 2-furyl | — | F | H | i-PrOC(O) |
| 22 | Et | 2-pyridyl | — | F | H | t-BtOC(O) |
| 23 | Et | Me | — | CN | H | H |
| 24 | Et | Et | — | CN | H | MeC(O) |
| 25 | Et | i-Pr | — | NO$_2$ | H | EtC(O) |
| 26 | Et | t-Bt | — | NO$_2$ | H | c-PrC(O) |
| 27 | Et | CF$_3$ | — | CH$_3$ | H | PhC(O) |
| 28 | Et | Ph | — | CH$_3$ | H | CH$_3$CH(OMe)CH$_2$C(O) |
| 29 | Et | 3,5-diCl—Ph | — | CF$_3$ | H | N≡CCH$_2$CH$_2$C(O) |
| 30 | Et | CH2=CH | — | CF$_3$ | H | CH$_3$C(OCH$_2$CH$_2$O)CH$_2$C(O) |
| 31 | Et | CH≡C | — | MeO | H | MeOC(O) |
| 32 | Et | 2-furyl | — | MeO | H | i-PrOC(O) |
| 33 | Et | 2-pyridyl | — | NH$_2$ | H | t-BtOC(O) |
| 34 | Et | Me | — | NH$_2$ | H | H |
| 35 | Et | Et | — | N(Me)$_2$ | H | MeC(O) |
| 36 | Et | i-Pr | — | N(Me)$_2$ | H | EtC(O) |
| 37 | Et | t-Bt | — | MeS | H | c-PrC(O) |
| 38 | Et | CF$_3$ | — | MeS | H | PhC(O) |
| 39 | i-Pr | Ph | — | MeS(O) | H | CH$_3$CH(OMe)CH$_2$C(O) |
| 40 | i-Pr | 3,5-diCl—Ph | — | MeS(O) | H | N≡CCH$_2$CH$_2$C(O) |
| 41 | i-Pr | CH2=CH | — | MeS(O)$_2$ | H | CH$_3$C(OCH$_2$CH$_2$O)CH$_2$C(O) |
| 42 | i-Pr | CH≡C | — | MeS(O)$_2$ | H | CH$_3$OC(O) |
| 43 | i-Pr | 2-furyl | — | 2-furyl | H | i-PrOC(O) |
| 44 | i-Pr | 2-pyridyl | — | 2-pyridyl | H | t-BtOC(O) |
| 45 | i-Pr | Me | — | Cl | H | H |
| 46 | i-Pr | Et | — | Cl | MeC(O) | MeC(O) |
| 47 | i-Pr | i-Pr | — | Cl | EtC(O) | EtC(O) |
| 48 | i-Pr | t-Bt | — | Cl | c-PrC(O) | c-PrC(O) |
| 49 | i-Pr | CF$_3$ | — | Cl | PhC(O) | PhC(O) |
| 50 | i-Pr | Ph | — | Cl | H | CH$_3$CH(OMe)CH$_2$C(O) |
| 51 | CF$_3$ | 3,5-diCl—Ph | 2-Cl | H | H | N≡CCH$_2$CH$_2$C(O) |
| 52 | CF$_3$ | 3,5-diCl—Ph | 5-Cl | H | H | CH$_3$C(OCH$_2$CH$_2$O)CH$_2$C(O) |
| 53 | CF$_3$ | 3,5-diCl—Ph | 6-Cl | H | H | CH$_3$OC(O) |
| 54 | CF$_3$ | 3,5-diCl—Ph | 2-Br | H | H | i-PrOC(O) |
| 55 | CF$_3$ | 3,5-diCl—Ph | 5-Br | H | H | t-BtOC(O) |
| 56 | CF$_3$ | 3,5-diCl—Ph | 6-Br | H | H | H |
| 57 | CF$_3$ | 3,5-diCl—Ph | 2-I | H | H | MeC(O) |
| 58 | CF$_3$ | 3,5-diCl—Ph | 5-I | H | H | EtC(O) |
| 59 | CF$_3$ | 3,5-diCl—Ph | 6-I | H | H | c-PrC(O) |
| 60 | CF$_3$ | 3,5-diCl—Ph | 2-F | H | H | PhC(O) |
| 61 | CF$_3$ | 3,5-diCl—Ph | 5-F | H | H | CH$_3$CH(OMe)CH$_2$C(O) |
| 62 | CF$_3$ | 3,5-diCl—Ph | 6-F | H | H | N≡CCH$_2$CH$_2$C(O) |
| 63 | CF$_3$ | 3,5-diCl—Ph | 2-NO$_2$ | H | H | CH$_3$C(OCH$_2$CH$_2$O)CH$_2$C(O) |
| 64 | CF$_3$ | 3,5-diCl—Ph | 5-NO$_2$ | H | H | CH$_3$OC(O) |
| 65 | CF$_3$ | 3,5-diCl—Ph | 6-NO$_2$ | H | H | i-PrOC(O) |
| 66 | CF$_3$ | 3,5-diCl—Ph | 2-OH | H | H | t-BtOC(O) |
| 67 | CF$_3$ | 3,5-diCl—Ph | 5-OH | H | H | H |
| 68 | CF$_3$ | 3,5-diCl—Ph | 6-OH | H | H | MeC(O) |
| 69 | CF$_3$ | 3,5-diCl—Ph | 2-SH | H | H | EtC(O) |
| 70 | CF$_3$ | 3,5-diCl—Ph | 5-SH | H | H | c-PrC(O) |
| 71 | CF$_3$ | 3,5-diCl—Ph | 6-SH | H | H | PhC(O) |
| 72 | CF$_3$ | 3,5-diCl—Ph | 2-NH | H | H | CH$_3$CH(OMe)CH$_2$C(O) |
| 73 | CF$_3$ | 3,5-diCl—Ph | 5-NH | Cl | H | N≡CCH$_2$CH$_2$C(O) |
| 74 | CF$_3$ | 3,5-diCl—Ph | 6-NH | Cl | H | CH$_3$C(OCH$_2$CH$_2$O)CH$_2$C(O) |
| 75 | CF$_3$ | 3,5-diCl—Ph | 2-N(Me) | Cl | H | CH$_3$OC(O) |
| 76 | CF$_3$ | 3,5-diCl—Ph | 5-N(Me) | Cl | H | i-PrOC(O) |

TABLE 4-continued

Examples of compounds (3)

| No. | Y | X | (Z)n | W | R1 | R2 |
|---|---|---|---|---|---|---|
| 77 | $CF_3$ | 3,5-diCl—Ph | 6-N(Me) | Br | H | t-BtOC(O) |
| 78 | $CF_3$ | 3,5-diCl—Ph | 2-CN | Br | H | H |
| 79 | $CF_3$ | 3,5-diCl—Ph | 5-CN | I | H | MeC(O) |
| 80 | $CF_3$ | 3,5-diCl—Ph | 6-CN | I | H | EtC(O) |
| 81 | $CF_3$ | 3,5-diCl—Ph | 2-Cl | F | H | c-PrC(O) |
| 82 | $CF_3$ | 3,5-diCl—Ph | 5-Cl | F | H | PhC(O) |
| 83 | $CF_3$ | 3,5-diCl—Ph | 6-Cl | $NO_2$ | H | $CH_3CH(OMe)CH_2C(O)$ |
| 84 | $CF_3$ | 3,5-diCl—Ph | 2-Br | $NO_2$ | H | N≡CCH$_2$CH$_2$C(O) |
| 85 | $CF_3$ | 3,5-diCl—Ph | 5-Br | OH | H | $CH_3C(OCH_2CH_2O)CH_2C(O)$ |
| 86 | $CF_3$ | 3,5-diCl—Ph | 6-Br | OH | H | $CH_3OC(O)$ |
| 87 | $CF_3$ | 3,5-diCl—Ph | 2-I | SH | H | i-PrOC(O) |
| 88 | $CF_3$ | 3,5-diCl—Ph | 5-I | SH | H | t-BtOC(O) |
| 89 | $CF_3$ | 3,5-diCl—Ph | 6-I | NH | H | H |
| 90 | $CF_3$ | 3,5-diCl—Ph | 2-F | NH | H | MeC(O) |
| 91 | $CF_3$ | 3,5-diCl—Ph | 5-F | N(Me) | H | EtC(O) |
| 92 | $CF_3$ | 3,5-diCl—Ph | 6-F | N(Me) | H | c-PrC(O) |
| 93 | $CF_3$ | 3,5-diCl—Ph | 2-OH | CN | H | PhC(O) |
| 94 | $CF_3$ | 3,5-diCl—Ph | 5-OH | CN | H | $CH_3CH(OMe)CH_2C(O)$ |
| 95 | $CF_3$ | 3,5-diCl—Ph | 6-OH | H | H | N≡CCH$_2$CH$_2$C(O) |
| 96 | $CF_3$ | 3,5-diCl—Ph | 2-Cl | H | H | $CH_3C(OCH_2CH_2O)CH_2C(O)$ |
| 97 | $CF_3$ | 3,5-diCl—Ph | 5-Cl | H | H | $CH_3OC(O)$ |
| 98 | $CF_3$ | 3,5-diCl—Ph | 2-Br | H | H | i-PrOC(O) |
| 99 | $CF_3$ | 3,5-diCl—Ph | 5-Br | H | H | t-BtOC(O) |
| 100 | $CF_3$ | 3,5-diCl—Ph | 2-Cl | H | H | H |

Examples of Compounds (4)

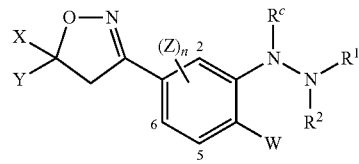

[Chemical formula 12]

TABLE 5

Examples of compounds (4)

| No. | Y | X | (Z)n | W | $R^c$ | $R^t$ | $R^2$ |
|---|---|---|---|---|---|---|---|
| 1 | Me | Me | — | H | H | H | H |
| 2 | Me | Et | — | H | H | H | MeC(O) |
| 3 | Me | i-Pr | — | H | H | H | EtC(O) |
| 4 | Me | t-Bt | — | H | H | H | c-PrC(O) |
| 5 | Me | $CF_3$ | — | H | H | H | PhC(O) |
| 6 | Me | Ph | — | H | H | H | $CH_3CH(OMe)CH_2C(O)$ |
| 7 | Me | 3,5-diCl—Ph | — | H | H | H | N≡CCH$_2$CH$_2$C(O) |
| 8 | Me | CH2=CH | — | H | H | H | $CH_3C(OCH_2CH_2O)CH_2C(O)$ |
| 9 | Me | CH≡C | — | H | H | H | MeOC(O) |
| 10 | Me | 2-furyl | — | H | H | H | i-PrOC(O) |
| 11 | Me | 2-pyridyl | — | H | H | H | t-BtOC(O) |
| 12 | Me | Me | — | Cl | H | H | H |
| 13 | Me | Et | — | Cl | H | H | MeC(O) |
| 14 | Me | i-Pr | — | Cl | H | H | EtC(O) |
| 15 | Me | t-Bt | — | Cl | H | H | c-PrC(O) |
| 16 | Me | $CF_3$ | — | Cl | H | H | PhC(O) |
| 17 | Me | Ph | — | Br | H | H | $CH_3CH(OMe)CH_2C(O)$ |
| 18 | Me | 3,5-diCl—Ph | — | Br | H | H | N≡CCH$_2$CH$_2$C(O) |
| 19 | Me | CH2=CH | — | I | H | H | $CH_3C(OCH_2CH_2O)CH_2C(O)$ |
| 20 | Et | CH≡C | — | I | H | H | $CH_3OC(O)$ |
| 21 | Et | 2-furyl | — | F | H | H | i-PrOC(O) |
| 22 | Et | 2-pyridyl | — | F | H | H | t-BtOC(O) |
| 23 | Et | Me | — | CN | H | H | H |
| 24 | Et | Et | — | CN | H | H | MeC(O) |
| 25 | Et | i-Pr | — | $NO_2$ | H | H | EtC(O) |
| 26 | Et | t-Bt | — | $NO_2$ | H | H | c-PrC(O) |

TABLE 5-continued

Examples of compounds (4)

| No. | Y | X | (Z)n | W | $R^c$ | $R^t$ | $R^2$ |
|---|---|---|---|---|---|---|---|
| 27 | Et | $CF_3$ | — | $CH_3$ | H | H | PhC(O) |
| 28 | Et | Ph | — | $CH_3$ | H | H | $CH_3CH(OMe)CH_2C(O)$ |
| 29 | Et | 3,5-diCl—Ph | — | $CF_3$ | H | H | $N\equiv CCH_2CH_2C(O)$ |
| 30 | Et | CH2=CH | — | $CF_3$ | H | H | $CH_3C(OCH_2CH_2O)CH_2C(O)$ |
| 31 | Et | CH≡C | — | MeO | H | H | MeOC(O) |
| 32 | Et | 2 furyl | — | MeO | H | H | i-PrOC(O) |
| 33 | Et | 2-pyridyl | — | $NH_2$ | H | H | t-BtOC(O) |
| 34 | Et | Me | — | $NH_2$ | H | H | H |
| 35 | Et | Et | — | $N(Me)_2$ | H | H | MeC(O) |
| 36 | Et | i-Pr | — | $N(Me)_2$ | H | H | EtC(O) |
| 37 | Et | t-Bt | — | MeS | H | H | c-PrC(O) |
| 38 | Et | $CF_3$ | — | MeS | H | H | PhC(O) |
| 39 | i-Pr | Ph | — | MeS(O) | H | H | $CH_3CH(OMe)CH_2C(O)$ |
| 40 | i-Pr | 3,5-diCl—Ph | — | MeS(O) | H | H | $N\equiv CCH_2CH_2C(O)$ |
| 41 | i-Pr | CH2=CH | — | $MeS(O)_2$ | H | H | $CH_3C(OCH_2CH_2O)CH_2C(O)$ |
| 41 | i-Pr | CH≡C | — | $MeS(O)_2$ | H | H | $CH_3OC(O)$ |
| 43 | i-Pr | 2-furyl | — | 2-furyl | H | H | i-PrOC(O) |
| 44 | i-Pr | 2-pyridyl | — | 2-pyridyl | H | H | t-BtOC(O) |
| 45 | i-Pr | Me | — | Cl | H | H | H |
| 46 | i-Pr | Et | — | Cl | H | MeC(O) | MeC(O) |
| 47 | i-Pr | i-Pr | — | Cl | H | EtC(O) | EtC(O) |
| 48 | i-Pr | t-Bt | — | Cl | H | c-PrC(O) | c-PrC(O) |
| 49 | i-Pr | $CF_3$ | — | Cl | H | PhC(O) | PhC(O) |
| 50 | i-Pr | Ph | — | Cl | H | H | $CH_3CH(OMe)CH_2C(O)$ |
| 51 | $CF_3$ | 3,5-diCl—Ph | 2-Cl | H | H | H | $N\equiv CCH_2CH_2C(O)$ |
| 52 | $CF_3$ | 3,5-diCl—Ph | 5-Cl | H | Me | H | $CH_3C(OCH_2CH_2O)CH_2C(O)$ |
| 53 | $CF_3$ | 3,5-diCl—Ph | 6-Cl | H | Et | H | $CH_3OC(O)$ |
| 54 | $CF_3$ | 3,5-diCl—Ph | 2-Br | H | $CF_3$ | H | i-PrOC(O) |
| 55 | $CF_3$ | 3,5-diCl—Ph | 5-Br | H | Ph | H | t-BtOC(O) |
| 56 | $CF_3$ | 3,5-diCl—Ph | 6-Br | H | c-Pr | H | H |
| 57 | $CF_3$ | 3,5-diCl—Ph | 2-I | H | c-Hex | H | MeC(O) |
| 58 | $CF_3$ | 3,5-diCl—Ph | 5-I | H | $PhCH_2$ | H | EtC(O) |
| 59 | $CF_3$ | 3,5-diCl—Ph | 6-I | H | CH2=CH | H | c-PrC(O) |
| 60 | $CF_3$ | 3,5-diCl—Ph | 2-F | H | CH≡C | H | PhC(O) |
| 61 | $CF_3$ | 3,5-diCl—Ph | 5-F | H | H | H | $CH_3CH(OMe)CH_2C(O)$ |
| 62 | $CF_3$ | 3,5-diCl—Ph | 6-F | H | Me | H | $N\equiv CCH_2CH_2C(O)$ |
| 63 | $CF_3$ | 3,5-diCl—Ph | $2-NO_2$ | H | Et | H | $CH_3C(OCH_2CH_2O)CH_2C(O)$ |
| 64 | $CF_3$ | 3,5-diCl—Ph | $5-NO_2$ | H | $CF_3$ | H | $CH_3OC(O)$ |
| 65 | $CF_3$ | 3,5 diCl—Ph | $6-NO_2$ | H | Ph | H | i-PrOC(O) |
| 66 | $CF_3$ | 3,5-diCl—Ph | 2-OH | H | c-Pr | H | t-BtOC(O) |
| 67 | $CF_3$ | 3,5-diCl—Ph | 5-OH | H | c-Hex | H | H |
| 68 | $CF_3$ | 3,5-diCl—Ph | 6-OH | H | $PhCH_2$ | H | MeC(O) |
| 69 | $CF_3$ | 3,5-diCl—Ph | 2-SH | H | CH2=CH | H | EtC(O) |
| 70 | $CF_3$ | 3,5-diCl—Ph | 5-SH | H | CH≡C | H | c-PrC(O) |
| 71 | $CF_3$ | 3,5-diCl—Ph | 6-SH | H | H | H | PhC(O) |
| 72 | $CF_3$ | 3,5-diCl—Ph | 2-NH | H | Me | H | $CH_3CH(OMe)CH_2C(O)$ |
| 73 | $CF_3$ | 3,5-diCl—Ph | 5-NH | Cl | Et | H | $N\equiv CCH_2CH_2C(O)$ |
| 74 | $CF_3$ | 3,5-diCl—Ph | 6-NH | Cl | $CF_3$ | H | $CH_3C(OCH_2CH_2O)CH_2C(O)$ |
| 75 | $CF_3$ | 3,5-diCl—Ph | 2-N(Me) | Cl | Ph | H | $CH_3OC(O)$ |
| 76 | $CF_3$ | 3,5-diCl—Ph | 5-N(Me) | Cl | c-Pr | H | i-PrOC(O) |
| 77 | $CF_3$ | 3,5-diCl—Ph | 6-N(Me) | Br | c-Hex | H | t-BtOC(O) |
| 78 | $CF_3$ | 3,5-diCl—Ph | 2-CN | Br | $PhCH_2$ | H | H |
| 79 | $CF_3$ | 3,5-diCl—Ph | 5-CN | I | CH2=CH | H | MeC(O) |
| 80 | $CF_3$ | 3,5-diCl—Ph | 6-CN | I | CH≡C | H | EtC(O) |
| 81 | $CF_3$ | 3,5-diCl—Ph | 2-Cl | F | H | H | c-PrC(O) |
| 82 | $CF_3$ | 3,5-diCl—Ph | 5-Cl | F | Me | H | PhC(O) |
| 83 | $CF_3$ | 3,5-diCl—Ph | 6-Cl | $NO_2$ | Et | H | $CH_3CH(OMe)CH_2C(O)$ |
| 84 | $CF_3$ | 3,5-diCl—Ph | 2-Br | $NO_2$ | $CF_3$ | H | $N\equiv CCH_2CH_2C(O)$ |
| 85 | $CF_3$ | 3,5-diCl—Ph | 5-Br | OH | Ph | H | $CH_3C(OCH_2CH_2O)CH_2C(O)$ |
| 86 | $CF_3$ | 3,5-diCl—Ph | 6-Br | OH | c-Pr | H | $CH_3OC(O)$ |
| 87 | $CF_3$ | 3,5-diCl—Ph | 2-I | SH | c-Hex | H | i-PrOC(O) |
| 88 | $CF_3$ | 3,5-diCl—Ph | 5-I | SH | $PhCH_2$ | H | t-BtOC(O) |
| 89 | $CF_3$ | 3,5-diCl—Ph | 6-I | NH | CH2=CH | H | H |
| 90 | $CF_3$ | 3,5-diCl—Ph | 2-F | NH | CH≡C | H | MeC(O) |
| 91 | $CF_3$ | 3,5-diCl—Ph | 5-F | N(Me) | H | H | EtC(O) |
| 92 | $CF_3$ | 3,5-diCl—Ph | 6-F | N(Me) | Me | H | c-PrC(O) |
| 93 | $CF_3$ | 3,5-diCl—Ph | 2-OH | CN | Et | H | PhC(O) |
| 94 | $CF_3$ | 3,5-diCl—Ph | 5-OH | CN | $CF_3$ | H | $CH_3CH(OMe)CH_2C(O)$ |
| 95 | $CF_3$ | 3,5-diCl—Ph | 6-OH | H | Ph | H | $N\equiv CCH_2CH_2C(O)$ |
| 96 | $CF_3$ | 3,5-diCl—Ph | 2-Cl | H | c-Pr | H | $CH_3C(OCH_2CH_2O)CH_2C(O)$ |
| 97 | $CF_3$ | 3,5-diCl—Ph | 5-Cl | H | c-Hex | H | $CH_3OC(O)$ |
| 98 | $CF_3$ | 3,5-diCl—Ph | 2-Br | H | $PhCH_2$ | H | i-PrOC(O) |
| 99 | $CF_3$ | 3,5-diCl—Ph | 5-Br | H | CH2=CH | H | t-BtOC(O) |
| 100 | $CF_3$ | 3,5-diCl—Ph | 2-Cl | H | CH≡C | H | H |

Examples of Compounds (5)

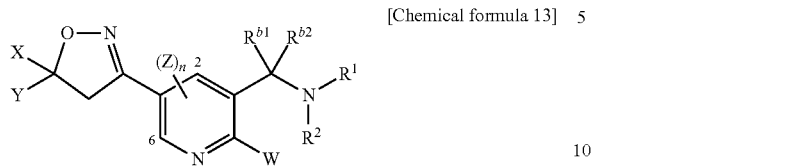

[Chemical formula 13]

TABLE 6

Examples of compounds (5)

| No. | Y | X | (Z)n | W | Rb1, Rb2 | R1 | R2 |
|---|---|---|---|---|---|---|---|
| 1 | Me | Me | — | H | H, H | H | H |
| 2 | Me | Et | — | H | H, H | H | MeC(O) |
| 3 | Me | i-Pr | — | H | H, H | H | EtC(O) |
| 4 | Me | t-Bt | — | H | H, H | H | c-PrC(O) |
| 5 | Me | $CF_3$ | — | H | H, H | H | PhC(O) |
| 6 | Me | Ph | — | H | H, H | H | $CH_3CH(OMe)CH_2C(O)$ |
| 7 | Me | 3,5-diCl—Ph | — | H | H, H | H | N≡$CCH_2CH_2C(O)$ |
| 8 | Me | CH2=CH | — | H | H, H | H | $CH_3C(OCH_2CH_2O)CH_2C(O)$ |
| 9 | Me | CH≡C | — | H | H, H | H | MeOC(O) |
| 10 | Me | 2-furyl | — | H | H, H | H | i-PrOC(O) |
| 11 | Me | 2-pyridyl | — | H | H, H | H | t-BtOC(O) |
| 12 | Me | Me | — | Cl | H, H | H | H |
| 13 | Me | Et | — | Cl | H, H | H | MeC(O) |
| 14 | Me | i-Pr | — | Cl | H, H | H | EtC(O) |
| 15 | Me | t-Bt | — | Cl | H, H | H | c-PrC(O) |
| 16 | Me | $CF_3$ | — | Cl | H, H | H | PhC(O) |
| 17 | Me | Ph | — | Br | H, H | H | $CH_3CH(OMe)CH_2C(O)$ |
| 18 | Me | 3,5-diCl—Ph | — | Br | H, H | H | N≡$CCH_2CH_2C(O)$ |
| 19 | Me | CH2=CH | — | I | H, H | H | $CH_3C(OCH_2CH_2O)CH_2C(O)$ |
| 20 | Et | CH≡C | — | I | H, H | H | $CH_3OC(O)$ |
| 21 | Et | 2-furyl | — | F | H, H | H | i-PrOC(O) |
| 22 | Et | 2-pyridyl | — | F | H, H | H | t-BtOC(O) |
| 23 | Et | Me | — | CN | H, H | H | H |
| 24 | Et | Et | — | CN | H, H | H | MeC(O) |
| 25 | Et | i-Pr | — | $NO_2$ | H, H | H | EtC(O) |
| 26 | Et | t-Bt | — | $NO_2$ | H, H | H | c-PrC(O) |
| 27 | Et | $CF_3$ | — | $CH_3$ | H, H | H | PhC(O) |
| 28 | Et | Ph | — | $CH_3$ | H, H | H | $CH_3CH(OMe)CH_2C(O)$ |
| 29 | Et | 3,5-diCl—Ph | — | $CF_3$ | H, H | H | N≡$CCH_2CH_2C(O)$ |
| 30 | Et | CH2=CH | — | $CF_3$ | H, H | H | $CH_3C(OCH_2CH_2O)CH_2C(O)$ |
| 31 | Et | CH≡C | — | MeO | H, H | H | MeOC(O) |
| 32 | Et | 2-furyl | — | MeO | H, H | H | i-PrOC(O) |
| 33 | Et | 2-pyridyl | — | $NH_2$ | H, H | H | t-BtOC(O) |
| 34 | Et | Me | — | $NH_2$ | H, H | H | H |
| 35 | Et | Et | — | $N(Me)_2$ | H, H | H | MeC(O) |
| 36 | Et | i-Pr | — | $N(Me)_2$ | H, H | H | EtC(O) |
| 37 | Et | t-Bt | — | MeS | H, H | H | c-PrC(O) |
| 38 | Et | $CF_3$ | — | MeS | H, H | H | PhC(O) |
| 39 | i-Pr | Ph | — | MeS(O) | H, H | H | $CH_3CH(OMe)CH_2C(O)$ |
| 40 | i-Pr | 3,5-diCl—Ph | — | MeS(O) | H, H | H | N≡$CCH_2CH_2C(O)$ |
| 41 | i-Pr | CH2=CH | — | $MeS(O)_2$ | H, H | H | $CH_3C(OCH_2CH_2O)CH_2C(O)$ |
| 41 | i-Pr | CH≡C | — | $MeS(O)_2$ | H, H | H | $CH_3OC(O)$ |
| 43 | i-Pr | 2-furyl | — | 2-furyl | H, H | H | i-PrOC(O) |
| 44 | i-Pr | 2-pyridyl | — | 2-pyridyl | H, H | H | t-BtOC(O) |
| 45 | i-Pr | Me | — | Cl | H, H | H | H |
| 46 | i-Pr | Et | — | Cl | H, H | MeC(O) | MeC(O) |
| 47 | i-Pr | i-Pr | — | Cl | H, H | EtC(O) | EtC(O) |
| 48 | i-Pr | t-Bt | — | Cl | H, H | c-PrC(O) | c-PrC(O) |
| 49 | i-Pr | $CF_3$ | — | Cl | H, H | PhC(O) | PhC(O) |
| 50 | i-Pr | Ph | — | Cl | H, H | H | $CH_3CH(OMe)CH_2C(O)$ |
| 51 | $CF_3$ | 3,5-diCl—Ph | 2-Cl | H | H, H | H | N≡$CCH_2CH_2C(O)$ |
| 52 | $CF_3$ | 3,5-diCl—Ph | 6-Cl | H | H, Me | H | $CH_3C(OCH_2CH_2O)CH_2C(O)$ |
| 53 | $CF_3$ | 3,5-diCl—Ph | 2-Cl | H | H, Et | H | $CH_3OC(O)$ |
| 54 | $CF_3$ | 3,5-diCl—Ph | 6-Cl | H | Me, Me | H | i-PrOC(O) |
| 55 | $CF_3$ | 3,5-diCl—Ph | 2-Br | H | H, H | H | t-BtOC(O) |
| 56 | $CF_3$ | 3,5-diCl—Ph | 6-Br | H | H, Me | H | H |
| 57 | $CF_3$ | 3,5-diCl—Ph | 2-I | H | H, Et | H | MeC(O) |
| 58 | $CF_3$ | 3,5-diCl—Ph | 6-I | H | Me, Me | H | EtC(O) |
| 59 | $CF_3$ | 3,5-diCl—Ph | 2-F | H | H, H | H | c-PrC(O) |
| 60 | $CF_3$ | 3,5-diCl—Ph | 6-F | H | H, Me | H | PhC(O) |

TABLE 6-continued

Examples of compounds (5)

| No. | Y | X | (Z)n | W | Rb1, Rb2 | R1 | R2 |
|---|---|---|---|---|---|---|---|
| 61 | $CF_3$ | 3,5-diCl—Ph | 2-$NO_2$ | H | H, Et | H | $CH_3CH(OMe)CH_2C(O)$ |
| 62 | $CF_3$ | 3,5-diCl—Ph | 6-$NO_2$ | H | Me, Me | H | $N{=}CCH_2CH_2C(O)$ |
| 63 | $CF_3$ | 3,5-diCl—Ph | 2-OH | H | H, H | H | $CH_3C(OCH_2CH_2O)CH_2C(O)$ |
| 64 | $CF_3$ | 3,5-diCl—Ph | 6-OH | H | H, Me | H | $CH_3OC(O)$ |
| 65 | $CF_3$ | 3,5-diCl—Ph | 2-SH | H | H, Et | H | i-PrC(O) |
| 66 | $CF_3$ | 3,5-diCl—Ph | 6-SH | H | Me, Me | H | t-BtOC(O) |
| 67 | $CF_3$ | 3,5-diCl—Ph | 2-NH | H | H, H | H | H |
| 68 | $CF_3$ | 3,5-diCl—Ph | 6-NH | H | H, Me | H | MeC(O) |
| 69 | $CF_3$ | 3,5-diCl—Ph | 2-N(Me) | H | H, Et | H | EtC(O) |
| 70 | $CF_3$ | 3,5-diCl—Ph | 6-N(Me) | H | Me, Me | H | c-PrC(O) |
| 71 | $CF_3$ | 3,5-diCl—Ph | 2-CN | H | H, H | H | PhC(O) |
| 72 | $CF_3$ | 3,5-diCl—Ph | 6-CN | H | H, Me | H | $CH_3CH(OMe)CH_2C(O)$ |
| 73 | $CF_3$ | 3,5-diCl—Ph | 2-Cl | Cl | H, H | H | $N{=}CCH_2CH_2C(O)$ |
| 74 | $CF_3$ | 3,5-diCl—Ph | 6-Cl | Cl | H, $CF_3$ | H | $CH_3C(OCH_2CH_2O)CH_2C(O)$ |
| 75 | $CF_3$ | 3,5-diCl—Ph | 2-Cl | Cl | H, Et | H | $CH_3OC(O)$ |
| 76 | $CF_3$ | 3,5-diCl—Ph | 6-Cl | Cl | Me, Me | H | i-PrC(O) |
| 77 | $CF_3$ | 3,5-diCl—Ph | 2-Br | Br | H, H | H | t-BtOC(O) |
| 78 | $CF_3$ | 3,5-diCl—Ph | 6-Br | Br | H, $CF_3$ | H | H |
| 79 | $CF_3$ | 3,5-diCl—Ph | 2-I | I | H, Et | H | MeC(O) |
| 80 | $CF_3$ | 3,5-diCl—Ph | 6-I | I | Me, Me | H | EtC(O) |
| 81 | $CF_3$ | 3,5-diCl—Ph | 2-F | F | H, H | H | c-PrC(O) |
| 82 | $CF_3$ | 3,5-diCl—Ph | 6-F | F | H, Me | H | PhC(O) |
| 83 | $CF_3$ | 3,5-diCl—Ph | 2-$NO_2$ | $NO_2$ | H, Et | H | $CH_3CH(OMe)CH_2C(O)$ |
| 84 | $CF_3$ | 3,5-diCl—Ph | 6-$NO_2$ | $NO_2$ | Me, Me | H | $N{=}CCH_2CH_2C(O)$ |
| 85 | $CF_3$ | 3,5-diCl—Ph | 2-OH | OH | H, H | H | $CH_3C(OCH_2CH_2O)CH_2C(O)$ |
| 86 | $CF_3$ | 3,5-diCl—Ph | 6-OH | OH | H, Me | H | $CH_3OC(O)$ |
| 87 | $CF_3$ | 3,5-diCl—Ph | 2-SH | SH | H, Et | H | i-PrC(O) |
| 88 | $CF_3$ | 3,5-diCl—Ph | 6-SH | SH | Me, Me | H | t-BtOC(O) |
| 89 | $CF_3$ | 3,5-diCl—Ph | 2-NH | NH | H, H | H | H |
| 90 | $CF_3$ | 3,5-diCl—Ph | 6-NH | NH | H, Me | H | MeC(O) |
| 91 | $CF_3$ | 3,5-diCl—Ph | 2-N(Me) | N(Me) | H, Et | H | EtC(O) |
| 92 | $CF_3$ | 3,5-diCl—Ph | 6-N(Me) | N(Me) | Me, Me | H | c-PrC(O) |
| 93 | $CF_3$ | 3,5-diCl—Ph | 2-CN | CN | H, H | H | PhC(O) |
| 94 | $CF_3$ | 3,5-diCl—Ph | 6-CN | CN | H, Me | H | $CH_3CH(OMe)CH_2C(O)$ |
| 95 | $CF_3$ | 3,5-diCl—Ph | 2-Cl | H | H, Ph | H | $N{=}CCH_2CH_2C(O)$ |
| 96 | $CF_3$ | 3,5-diCl—Ph | 6-Cl | H | H, i-Pr | H | $CH_3C(OCH_2CH_2O)CH_2C(O)$ |
| 97 | $CF_3$ | 3,5-diCl—Ph | 2-Cl | H | H, c-Pr | H | $CH_3OC(O)$ |
| 98 | $CF_3$ | 3,5-diCl—Ph | 6-Cl | H | H, $CF_3$ | H | i-PrC(O) |
| 99 | $CF_3$ | 3,5-diCl—Ph | 2-Br | H | $CF_3$, $CF_3$ | H | t-BtOC(O) |
| 100 | $CF_3$ | 3,5-diCl—Ph | 6-Br | H | Et, Et | H | H |

Examples of Compounds (6)

[Chemical formula 14]

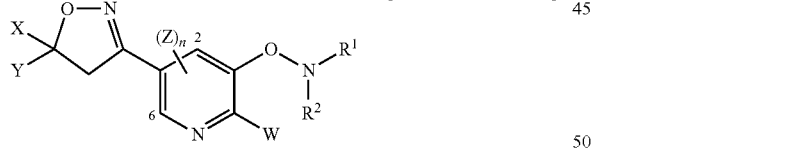

TABLE 7

Examples of compounds (6)

| No. | Y | X | (Z)n | W | R1 | R2 |
|---|---|---|---|---|---|---|
| 1 | Me | Me | — | H | H | H |
| 2 | Me | Et | — | H | H | MeC(O) |
| 3 | Me | i-Pr | — | H | H | EtC(O) |
| 4 | Me | t-Bt | — | H | H | c-PrC(O) |
| 5 | Me | $CF_3$ | — | H | H | PhC(O) |
| 6 | Me | Ph | — | H | H | $CH_3CH(OMe)CH_2C(O)$ |
| 7 | Me | 3,5-diCl—Ph | — | H | H | $N{=}CCH_2CH_2C(O)$ |
| 8 | Me | CH2=CH | — | H | H | $CH_3C(OCH_2CH_2O)CH_2C(O)$ |
| 9 | Me | CH≡C | — | H | H | MeOC(O) |
| 10 | Me | 2-furyl | — | H | H | i-PrC(O) |
| 11 | Me | 2-pyridyl | — | H | H | t-BtOC(O) |

TABLE 7-continued

Examples of compounds (6)

| No. | Y | X | (Z)n | W | R1 | R2 |
|---|---|---|---|---|---|---|
| 12 | Me | Me | — | Cl | H | H |
| 13 | Me | Et | — | Cl | H | MeC(O) |
| 14 | Me | i-Pr | — | Cl | H | EtC(O) |
| 15 | Me | t-Bt | — | Cl | H | c-PrC(O) |
| 16 | Me | $CF_3$ | — | Cl | H | PhC(O) |
| 17 | Me | Ph | — | Br | H | $CH_3CH(OMe)CH_2C(O)$ |
| 18 | Me | 3,5-diCl—Ph | — | Br | H | $N=CCH_2CH_2C(O)$ |
| 19 | Me | CH2=CH | — | I | H | $CH_3C(OCH_2CH_2O)CH_2C(O)$ |
| 20 | Et | CH≡C | — | I | H | $CH_3OC(O)$ |
| 21 | Et | 2-furyl | — | F | H | i-PrOC(O) |
| 22 | Et | 2-pyridyl | — | F | H | t-BtOC(O) |
| 23 | Et | Me | — | CN | H | H |
| 24 | Et | Et | — | CN | H | MeC(O) |
| 25 | Et | i-Pr | — | $NO_2$ | H | EtC(O) |
| 26 | Et | t-Bt | — | $NO_2$ | H | c-PrC(O) |
| 27 | Et | $CF_3$ | — | $CH_3$ | H | PhC(O) |
| 28 | Et | Ph | — | $CH_3$ | H | $CH_3CH(OMe)CH_2C(O)$ |
| 29 | Et | 3,5-diCl—Ph | — | $CF_3$ | H | $N=CCH_2CH_2C(O)$ |
| 30 | Et | CH2=CH | — | $CF_3$ | H | $CH_3C(OCH_2CH_2O)CH_2C(O)$ |
| 31 | Et | CH≡C | — | MeO | H | MeOC(O) |
| 32 | Et | 2-furyl | — | MeO | H | i-PrOC(O) |
| 33 | Et | 2-pyridyl | — | $NH_2$ | H | t-BtOC(O) |
| 34 | Et | Me | — | $NH_2$ | H | H |
| 35 | Et | Et | — | $N(Me)_2$ | H | MeC(O) |
| 36 | Et | i-Pr | — | $N(Me)_2$ | H | EtC(O) |
| 37 | Et | t-Bt | — | MeS | H | c-PrC(O) |
| 38 | Et | $CF_3$ | — | MeS | H | PhC(O) |
| 39 | i-Pr | Ph | — | MeS(O) | H | $CH_3CH(OMe)CH_2C(O)$ |
| 40 | i-Pr | 3,5-diCl—Ph | — | MeS(O) | H | $N=CCH_2CH_2C(O)$ |
| 41 | i-Pr | CH2=CH | — | $MeS(O)_2$ | H | $CH_3C(OCH_2CH_2O)CH_2C(O)$ |
| 41 | i-Pr | CH≡C | — | $MeS(O)_2$ | H | $CH_3OC(O)$ |
| 43 | i-Pr | 2-furyl | — | 2-furyl | H | i-PrOC(O) |
| 44 | i-Pr | 2-pyridyl | — | 2-pyridyl | H | t-BtOC(O) |
| 45 | i-Pr | Me | — | Cl | H | H |
| 46 | i-Pr | Et | — | Cl | MeC(O) | MeC(O) |
| 47 | i-Pr | i-Pr | — | Cl | EtC(O) | EtC(O) |
| 48 | i-Pr | t-Bt | — | Cl | c-PrC(O) | c-PrC(O) |
| 49 | i-Pr | $CF_3$ | — | Cl | PhC(O) | PhC(O) |
| 50 | i-Pr | Ph | — | Cl | H | $CH_3CH(OMe)CH_2C(O)$ |
| 51 | $CF_3$ | 3,5-diCl—Ph | 2-Cl | H | H | $N=CCH_2CH_2C(O)$ |
| 52 | $CF_3$ | 3,5-diCl—Ph | 6-Cl | H | H | $CH_3C(OCH_2CH_2O)CH_2C(O)$ |
| 53 | $CF_3$ | 3,5-diCl—Ph | 2-Br | H | H | $CH_3OC(O)$ |
| 54 | $CF_3$ | 3,5-diCl—Ph | 6-Br | H | H | i-PrOC(O) |
| 55 | $CF_3$ | 3,5-diCl—Ph | 2-I | H | H | t-BtOC(O) |
| 56 | $CF_3$ | 3,5-diCl—Ph | 6-I | H | H | H |
| 57 | $CF_3$ | 3,5-diCl—Ph | 2-F | H | H | MeC(O) |
| 58 | $CF_3$ | 3,5-diCl—Ph | 6-F | H | H | EtC(O) |
| 59 | $CF_3$ | 3,5-diCl—Ph | 2-OH | H | H | c-PrC(O) |
| 60 | $CF_3$ | 3,5-diCl—Ph | 6-OH | H | H | PhC(O) |
| 61 | $CF_3$ | 3,5-diCl—Ph | 2-SH | H | H | $CH_3CH(OMe)CH_2C(O)$ |
| 62 | $CF_3$ | 3,5-diCl—Ph | 6-SH | H | H | $N=CCH_2CH_2C(O)$ |
| 63 | $CF_3$ | 3,5-diCl—Ph | 2-NH | H | H | $CH_3C(OCH_2CH_2O)CH_2C(O)$ |
| 64 | $CF_3$ | 3,5-diCl—Ph | 6-NH | H | H | $CH_3OC(O)$ |
| 65 | $CF_3$ | 3,5-diCl—Ph | 2-N(Me) | H | H | i-PrOC(O) |
| 66 | $CF_3$ | 3,5-diCl—Ph | 6-N(Me) | H | H | t-BtOC(O) |
| 67 | $CF_3$ | 3,5-diCl—Ph | $2-NO_2$ | H | H | H |
| 68 | $CF_3$ | 3,5-diCl—Ph | $6-NO_2$ | H | H | MeC(O) |
| 69 | $CF_3$ | 3,5-diCl—Ph | 2-CN | H | H | EtC(O) |
| 70 | $CF_3$ | 3,5-diCl—Ph | 6-CN | H | H | c-PrC(O) |
| 71 | $CF_3$ | 3,5-diCl—Ph | 2-Cl | H | H | PhC(O) |
| 72 | $CF_3$ | 3,5-diCl—Ph | 6-Cl | H | H | $CH_3CH(OMe)CH_2C(O)$ |
| 73 | $CF_3$ | 3,5-diCl—Ph | 2-Br | Cl | H | $N=CCH_2CH_2C(O)$ |
| 74 | $CF_3$ | 3,5-diCl—Ph | 6-Br | Cl | H | $CH_3C(OCH_2CH_2O)CH_2C(O)$ |
| 75 | $CF_3$ | 3,5-diCl—Ph | 2-I | Cl | H | $CH_3OC(O)$ |
| 76 | $CF_3$ | 3,5-diCl—Ph | 6-I | Cl | H | i-PrOC(O) |
| 77 | $CF_3$ | 3,5-diCl—Ph | 2-F | Br | H | t-BtOC(O) |
| 78 | $CF_3$ | 3,5-diCl—Ph | 6-F | Br | H | H |
| 79 | $CF_3$ | 3,5-diCl—Ph | 2-OH | I | H | MeC(O) |
| 80 | $CF_3$ | 3,5-diCl—Ph | 6-OH | I | H | EtC(O) |
| 81 | $CF_3$ | 3,5-diCl—Ph | 2-SH | F | H | c-PrC(O) |
| 82 | $CF_3$ | 3,5-diCl—Ph | 6-SH | F | H | PhC(O) |
| 83 | $CF_3$ | 3,5-diCl—Ph | 2-NH | $NO_2$ | H | $CH_3CH(OMe)CH_2C(O)$ |
| 84 | $CF_3$ | 3,5-diCl—Ph | 6-NH | $NO_2$ | H | $N=CCH_2CH_2C(O)$ |
| 85 | $CF_3$ | 3,5-diCl—Ph | 2-N(Me) | OH | H | $CH_3C(OCH_2CH_2O)CH_2C(O)$ |
| 86 | $CF_3$ | 3,5-diCl—Ph | 6-N(Me) | OH | H | $CH_3OC(O)$ |
| 87 | $CF_3$ | 3,5-diCl—Ph | $2-NO_2$ | SH | H | i-PrOC(O) |

TABLE 7-continued

Examples of compounds (6)

| No. | Y | X | (Z)n | W | R1 | R2 |
|---|---|---|---|---|---|---|
| 88 | $CF_3$ | 3,5-diCl—Ph | 6-$NO_2$ | SH | H | t-BtOC(O) |
| 89 | $CF_3$ | 3,5-diCl—Ph | 2-CN | $NH_2$ | H | H |
| 90 | $CF_3$ | 3,5-diCl—Ph | 6-CN | $NH_2$ | H | MeC(O) |
| 91 | $CF_3$ | 3,5-diCl—Ph | 2-Cl | $N(Me)_2$ | H | EtC(O) |
| 92 | $CF_3$ | 3,5-diCl—Ph | 6-Cl | $N(Me)_2$ | H | c-PrC(O) |
| 93 | $CF_3$ | 3,5-diCl—Ph | 2-Br | CN | H | PhC(O) |
| 94 | $CF_3$ | 3,5-diCl—Ph | 6-Br | CN | H | $CH_3CH(OMe)CH_2C(O)$ |
| 95 | $CF_3$ | 3,5-diCl—Ph | 2-I | H | H | N≡$CCH_2CH_2C(O)$ |
| 96 | $CF_3$ | 3,5-diCl—Ph | 6-I | H | H | $CH_3C(OCH_2CH_2O)CH_2C(O)$ |
| 97 | $CF_3$ | 3,5-diCl—Ph | 2-F | H | H | $CH_3OC(O)$ |
| 98 | $CF_3$ | 3,5-diCl—Ph | 6-F | H | H | i-PrOC(O) |
| 99 | $CF_3$ | 3,5-diCl—Ph | 2-OH | H | H | t-BtOC(O) |
| 100 | $CF_3$ | 3,5-diCl—Ph | 6-OH | H | H | H |

Examples of Compounds (7)

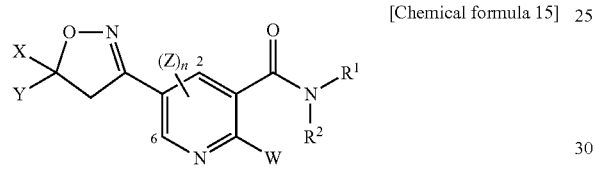

[Chemical formula 15]

TABLE 8

Examples of compounds (7)

| No. | Y | X | (Z)n | W | R1 | R2 |
|---|---|---|---|---|---|---|
| 1 | Me | Me | — | H | H | H |
| 2 | Me | Et | — | H | H | MeC(O) |
| 3 | Me | i-Pr | — | H | H | EtC(O) |
| 4 | Me | t-Bt | — | H | H | c-PrC(O) |
| 5 | Me | $CF_3$ | — | H | H | PhC(O) |
| 6 | Me | Ph | — | H | H | $CH_3CH(OMe)CH_2C(O)$ |
| 7 | Me | 3,5-diCl—Ph | — | H | H | N≡$CCH_2CH_2C(O)$ |
| 8 | Me | CH2=CH | — | H | H | $CH_3C(OCH_2CH_2O)CH_2C(O)$ |
| 9 | Me | CH≡C | — | H | H | MeOC(O) |
| 10 | Me | 2-furyl | — | H | H | i-PrOC(O) |
| 11 | Me | 2-pyridyl | — | H | H | t-BtOC(O) |
| 12 | Me | Me | — | Cl | H | H |
| 13 | Me | Et | — | Cl | H | MeC(O) |
| 14 | Me | i-Pr | — | Cl | H | EtC(O) |
| 15 | Me | t-Bt | — | Cl | H | c-PrC(O) |
| 16 | Me | $CF_3$ | — | Cl | H | PhC(O) |
| 17 | Me | Ph | — | Br | H | $CH_3CH(OMe)CH_2C(O)$ |
| 18 | Me | 3,5-diCl—Ph | — | Br | H | N≡$CCH_2CH_2C(O)$ |
| 19 | Me | CH2=CH | — | I | H | $CH_3C(OCH_2CH_2O)CH_2C(O)$ |
| 20 | Et | CH≡C | — | I | H | $CH_3OC(O)$ |
| 21 | Et | 2-furyl | — | F | H | i-PrOC(O) |
| 22 | Et | 2-pyridyl | — | F | H | t-BtOC(O) |
| 23 | Et | Me | — | CN | H | H |
| 24 | Et | Et | — | CN | H | MeC(O) |
| 25 | Et | i-Pr | — | $NO_2$ | H | EtC(O) |
| 26 | Et | t-Bt | — | $NO_2$ | H | c-PrC(O) |
| 27 | Et | $CF_3$ | — | $CH_3$ | H | PhC(O) |
| 28 | Et | Ph | — | $CH_3$ | H | $CH_3CH(OMe)CH_2C(O)$ |
| 29 | Et | 3,5-diCl—Ph | — | $CF_3$ | H | N≡$CCH_2CH_2C(O)$ |
| 30 | Et | CH2=CH | — | $CF_3$ | H | $CH_3C(OCH_2CH_2O)CH_2C(O)$ |
| 31 | Et | CH≡C | — | MeO | H | MeOC(O) |
| 32 | Et | 2-furyl | — | MeO | H | i-PrOC(O) |

TABLE 8-continued

Examples of compounds (7)

| No. | Y | X | (Z)n | W | R1 | R2 |
|---|---|---|---|---|---|---|
| 33 | Et | 2-pyridyl | — | $NH_2$ | H | t-BtOC(O) |
| 34 | Et | Me | — | $NH_2$ | H | H |
| 35 | Et | Et | — | $N(Me)_2$ | H | MeC(O) |
| 36 | Et | i-Pr | — | $N(Me)_2$ | H | EtC(O) |
| 37 | Et | t-Bt | — | MeS | H | c-PrC(O) |
| 38 | Et | $CF_3$ | — | MeS | H | PhC(O) |
| 39 | i-Pr | Ph | — | MeS(O) | H | $CH_3CH(OMe)CH_2C(O)$ |
| 40 | i-Pr | 3,5-diCl—Ph | — | MeS(O) | H | $N\equiv CCH_2CH_2C(O)$ |
| 41 | i-Pr | CH2=CH | — | $MeS(O)_2$ | H | $CH_3C(OCH_2CH_2O)CH_2C(O)$ |
| 41 | i-Pr | CH≡C | — | $MeS(O)_2$ | H | $CH_3OC(O)$ |
| 43 | i-Pr | 2-furyl | — | 2-furyl | H | i-PrOC(O) |
| 44 | i-Pr | 2-pyridyl | — | 2-pyridyl | H | t-BtOC(O) |
| 45 | i-Pr | Me | — | Cl | H | H |
| 46 | i-Pr | Et | — | Cl | MeC(O) | MeC(O) |
| 47 | i-Pr | i-Pr | — | Cl | EtC(O) | EtC(O) |
| 48 | i-Pr | t-Bt | — | Cl | c-PrC(O) | c-PrC(O) |
| 49 | i-Pr | $CF_3$ | — | Cl | PhC(O) | PhC(O) |
| 50 | i-Pr | Ph | — | Cl | H | $CH_3CH(OMe)CH_2C(O)$ |
| 51 | $CF_3$ | 3,5-diCl—Ph | 2-Cl | H | H | $N\equiv CCH_2CH_2C(O)$ |
| 52 | $CF_3$ | 3,5-diCl—Ph | 6-Cl | H | H | $CH_3C(OCH_2CH_2O)CH_2C(O)$ |
| 53 | $CF_3$ | 3,5-diCl—Ph | 2-Br | H | H | $CH_3OC(O)$ |
| 54 | $CF_3$ | 3,5-diCl—Ph | 6-Br | H | H | i-PrOC(O) |
| 55 | $CF_3$ | 3,5-diCl—Ph | 2-I | H | H | t-BtOC(O) |
| 56 | $CF_3$ | 3,5-diCl—Ph | 6-I | H | H | H |
| 57 | $CF_3$ | 3,5-diCl—Ph | 2-F | H | H | MeC(O) |
| 58 | $CF_3$ | 3,5-diCl—Ph | 6-F | H | H | EtC(O) |
| 59 | $CF_3$ | 3,5-diCl—Ph | 2-OH | H | H | c-PrC(O) |
| 60 | $CF_3$ | 3,5-diCl—Ph | 6-OH | H | H | PhC(O) |
| 61 | $CF_3$ | 3,5-diCl—Ph | 2-SH | H | H | $CH_3CH(OMe)CH_2C(O)$ |
| 62 | $CF_3$ | 3,5-diCl—Ph | 6-SH | H | H | $N\equiv CCH_2CH_2C(O)$ |
| 63 | $CF_3$ | 3,5-diCl—Ph | 2-NH | H | H | $CH_3C(OCH_2CH_2O)CH_2C(O)$ |
| 64 | $CF_3$ | 3,5-diCl—Ph | 6-NH | H | H | $CH_3OC(O)$ |
| 65 | $CF_3$ | 3,5-diCl—Ph | 2-N(Me) | H | H | i-PrOC(O) |
| 66 | $CF_3$ | 3,5-diCl—Ph | 6-N(Me) | H | H | t-BtOC(O) |
| 67 | $CF_3$ | 3,5-diCl—Ph | 2-$NO_2$ | H | H | H |
| 68 | $CF_3$ | 3,5-diCl—Ph | 6-$NO_2$ | H | H | MeC(O) |
| 69 | $CF_3$ | 3,5-diCl—Ph | 2-CN | H | H | EtC(O) |
| 70 | $CF_3$ | 3,5-diCl—Ph | 6-CN | H | H | c-PrC(O) |
| 71 | $CF_3$ | 3,5-diCl—Ph | 2-Cl | H | H | PhC(O) |
| 72 | $CF_3$ | 3,5-diCl—Ph | 6-Cl | H | H | $CH_3CH(OMe)CH_2C(O)$ |
| 73 | $CF_3$ | 3,5-diCl—Ph | 2-Br | Cl | H | $N\equiv CCH_2CH_2C(O)$ |
| 74 | $CF_3$ | 3,5-diCl—Ph | 6-Br | Cl | H | $CH_3C(OCH_2CH_2O)CH_2C(O)$ |
| 75 | $CF_3$ | 3,5-diCl—Ph | 2-I | Cl | H | $CH_3OC(O)$ |
| 76 | $CF_3$ | 3,5-diCl—Ph | 6-I | Cl | H | i-PrOC(O) |
| 77 | $CF_3$ | 3,5-diCl—Ph | 2-F | Br | H | t-BtOC(O) |
| 78 | $CF_3$ | 3,5-diCl—Ph | 6-F | Br | H | H |
| 79 | $CF_3$ | 3,5-diCl—Ph | 2-OH | I | H | MeC(O) |
| 80 | $CF_3$ | 3,5-diCl—Ph | 6-OH | I | H | EtC(O) |
| 81 | $CF_3$ | 3,5-diCl—Ph | 2-SH | F | H | c-PrC(O) |
| 82 | $CF_3$ | 3,5-diCl—Ph | 6-SH | F | H | PhC(O) |
| 83 | $CF_3$ | 3,5-diCl—Ph | 2-NH | $NO_2$ | H | $CH_3CH(OMe)CH_2C(O)$ |
| 84 | $CF_3$ | 3,5-diCl—Ph | 6-NH | $NO_2$ | H | $N\equiv CCH_2CH_2C(O)$ |
| 85 | $CF_3$ | 3,5-diCl—Ph | 2-$N(Me)_2$ | OH | H | $CH_3C(OCH_2CH_2O)CH_2C(O)$ |
| 86 | $CF_3$ | 3,5-diCl—Ph | 6-$N(Me)_2$ | OH | H | $CH_3OC(O)$ |
| 87 | $CF_3$ | 3,5-diCl—Ph | 2-$NO_2$ | SH | H | i-PrOC(O) |
| 88 | $CF_3$ | 3,5-diCl—Ph | 6-$NO_2$ | SH | H | t-BtOC(O) |
| 89 | $CF_3$ | 3,5-diCl—Ph | 2-CN | NH | H | H |
| 90 | $CF_3$ | 3,5-diCl—Ph | 6-CN | NH | H | MeC(O) |
| 91 | $CF_3$ | 3,5-diCl—Ph | 2-Cl | $N(Me)_2$ | H | EtC(O) |
| 92 | $CF_3$ | 3,5-diCl—Ph | 6-Cl | $N(Me)_2$ | H | c-PrC(O) |
| 93 | $CF_3$ | 3,5-diCl—Ph | 2-Br | CN | H | PhC(O) |
| 94 | $CF_3$ | 3,5-diCl—Ph | 6-Br | CN | H | $CH_3CH(OMe)CH_2C(O)$ |
| 95 | $CF_3$ | 3,5-diCl—Ph | 2-I | H | H | $N\equiv CCH_2CH_2C(O)$ |
| 96 | $CF_3$ | 3,5-diCl—Ph | 6-I | H | H | $CH_3C(OCH_2CH_2O)CH_2C(O)$ |
| 97 | $CF_3$ | 3,5-diCl—Ph | 2-F | H | H | $CH_3OC(O)$ |
| 98 | $CF_3$ | 3,5-diCl—Ph | 6-F | H | H | i-PrOC(O) |
| 99 | $CF_3$ | 3,5-diCl—Ph | 2-OH | H | H | t-BtOC(O) |
| 100 | $CF_3$ | 3,5-diCl—Ph | 6-OH | H | H | H |

Examples of Compounds (8)

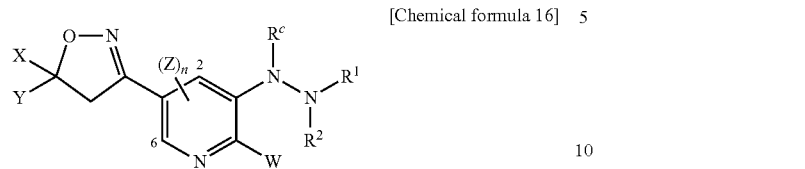

[Chemical formula 16]

TABLE 9

Examples of compounds (8)

| No. | Y | X | (Z)n | W | R$^c$ | R$^1$ | R$^2$ |
|---|---|---|---|---|---|---|---|
| 1 | Me | Me | — | H | H | H | H |
| 2 | Me | Et | — | H | H | H | MeC(O) |
| 3 | Me | i-Pr | — | H | H | H | EtC(O) |
| 4 | Me | t-Bt | — | H | H | H | c-PrC(O) |
| 5 | Me | CF$_3$ | — | H | H | H | PhC(O) |
| 6 | Me | Ph | — | H | H | H | CH$_3$CH(OMe)CH$_2$C(O) |
| 7 | Me | 3,5-diCl—Ph | — | H | H | H | N≡CCH$_2$CH$_2$C(O) |
| 8 | Me | CH2=CH | — | H | H | H | CH$_3$C(OCH$_2$CH$_2$O)CH$_2$C(O) |
| 9 | Me | CH≡C | — | H | H | H | MeOC(O) |
| 10 | Me | 2-furyl | — | H | H | H | i-PrOC(O) |
| 11 | Me | 2-pyridyl | — | H | H | H | t-BtOC(O) |
| 12 | Me | Me | — | Cl | H | H | H |
| 13 | Me | Et | — | Cl | H | H | MeC(O) |
| 14 | Me | i-Pr | — | Cl | H | H | EtC(O) |
| 15 | Me | t-Bt | — | Cl | H | H | c-PrC(O) |
| 16 | Me | CF$_3$ | — | Cl | H | H | PhC(O) |
| 17 | Me | Ph | — | Br | H | H | CH$_3$CH(OMe)CH$_2$C(O) |
| 18 | Me | 3,5-diCl—Ph | — | Br | H | H | N≡CCH$_2$CH$_2$C(O) |
| 19 | Me | CH2=CH | — | I | H | H | CH$_3$C(OCH$_2$CH$_2$O)CH$_2$C(O) |
| 20 | Et | CH≡C | — | I | H | H | CH$_3$OC(O) |
| 21 | Et | 2-furyl | — | F | H | H | i-PrOC(O) |
| 22 | Et | 2-pyridyl | — | F | H | H | t-BtOC(O) |
| 23 | Et | Me | — | CN | H | H | H |
| 24 | Et | Et | — | CN | H | H | MeC(O) |
| 25 | Et | i-Pr | — | NO$_2$ | H | H | EtC(O) |
| 26 | Et | t-Bt | — | NO$_2$ | H | H | c-PrC(O) |
| 27 | Et | CF$_3$ | — | CH$_3$ | H | H | PhC(O) |
| 28 | Et | Ph | — | CH$_3$ | H | H | CH$_3$CH(OMe)CH$_2$C(O) |
| 29 | Et | 3,5-diCl—Ph | — | CF$_3$ | H | H | N≡CCH$_2$CH$_2$C(O) |
| 30 | Et | CH2=CH | — | CF$_3$ | H | H | CH$_3$C(OCH$_2$CH$_2$O)CH$_2$C(O) |
| 31 | Et | CH≡C | — | MeO | H | H | MeOC(O) |
| 32 | Et | 2-furyl | — | MeO | H | H | i-PrOC(O) |
| 33 | Et | 2-pyridyl | — | NH$_2$ | H | H | t-BtOC(O) |
| 34 | Et | Me | — | NH$_2$ | H | H | H |
| 35 | Et | Et | — | N(Me)$_2$ | H | H | MeC(O) |
| 36 | Et | i-Pr | — | N(Me)$_2$ | H | H | EtC(O) |
| 37 | Et | t-Bt | — | MeS | H | H | c-PrC(O) |
| 38 | Et | CF$_3$ | — | MeS | H | H | PhC(O) |
| 39 | i-Pr | Ph | — | MeS(O) | H | H | CH$_3$CH(OMe)CH$_2$C(O) |
| 40 | i-Pr | 3,5-diCl—Ph | — | MeS(O) | H | H | N≡CCH$_2$CH$_2$C(O) |
| 41 | i-Pr | CH2=CH | — | MeS(O)$_2$ | H | H | CH$_3$C(OCH$_2$CH$_2$O)CH$_2$C(O) |
| 41 | i-Pr | CH≡C | — | MeS(O)$_2$ | H | H | CH$_3$OC(O) |
| 43 | i-Pr | 2-furyl | — | 2-furyl | H | H | i-PrOC(O) |
| 44 | i-Pr | 2-pyridyl | — | 2-pyridyl | H | H | t-BtOC(O) |
| 45 | i-Pr | Me | — | Cl | H | H | H |
| 46 | i-Pr | Et | — | Cl | H | MeC(O) | MeC(O) |
| 47 | i-Pr | i-Pr | — | Cl | H | EtC(O) | EtC(O) |
| 48 | i-Pr | t-Bt | — | Cl | H | c-PrC(O) | c-PrC(O) |
| 49 | i-Pr | CF$_3$ | — | Cl | H | PhC(O) | PhC(O) |
| 50 | i-Pr | Ph | — | Cl | H | H | CH$_3$CH(OMe)CH$_2$C(O) |
| 51 | CF$_3$ | 3,5-diCl—Ph | 2-Cl | H | H | H | N≡CCH$_2$CH$_2$C(O) |
| 52 | CF$_3$ | 3,5-diCl—Ph | 6-Cl | H | Me | H | CH$_3$C(OCH$_2$CH$_2$O)CH$_2$C(O) |
| 53 | CF$_3$ | 3,5-diCl—Ph | 2-Br | H | Et | H | CH$_3$OC(O) |
| 54 | CF$_3$ | 3,5-diCl—Ph | 6-Br | H | CF$_3$ | H | i-PrOC(O) |
| 55 | CF$_3$ | 3,5-diCl—Ph | 2-I | H | Ph | H | t-BtOC(O) |
| 56 | CF$_3$ | 3,5-diCl—Ph | 6-I | H | c-Pr | H | H |
| 57 | CF$_3$ | 3,5-diCl—Ph | 2-F | H | c-Hex | H | MeC(O) |
| 58 | CF$_3$ | 3,5-diCl—Ph | 6-F | H | PhCH$_2$ | H | EtC(O) |
| 59 | CF$_3$ | 3,5-diCl—Ph | 2-NO$_2$ | H | CH$_2$=CH | H | c-PrC(O) |
| 60 | CF$_3$ | 3,5-diCl—Ph | 6-NO$_2$ | H | CH≡C | H | PhC(O) |

TABLE 9-continued

Examples of compounds (8)

| No. | Y | X | (Z)n | W | R$^c$ | R$^1$ | R$^2$ |
|---|---|---|---|---|---|---|---|
| 61 | CF$_3$ | 3,5-diCl—Ph | 2-OH | H | H | H | CH$_3$CH(OMe)CH$_2$C(O) |
| 62 | CF$_3$ | 3,5-diCl—Ph | 6-OH | H | Me | H | N≡CCH$_2$CH$_2$C(O) |
| 63 | CF$_3$ | 3,5-diCl—Ph | 2-SH | H | Et | H | CH$_3$C(OCH$_2$CH$_2$O)CH$_2$C(O) |
| 64 | CF$_3$ | 3,5-diCl—Ph | 6-SH | H | CF$_3$ | H | CH$_3$OC(O) |
| 65 | CF$_3$ | 3,5-diCl—Ph | 2-NH | H | Ph | H | i-PrOC(O) |
| 66 | CF$_3$ | 3,5-diCl—Ph | 6-NH | H | c-Pr | H | t-BtOC(O) |
| 67 | CF$_3$ | 3,5-diCl—Ph | 2-N(Me) | H | c-Hex | H | H |
| 68 | CF$_3$ | 3,5-diCl—Ph | 6-N(Me) | H | PhCH$_2$ | H | MeC(O) |
| 69 | CF$_3$ | 3,5-diCl—Ph | 2-CN | H | CH2=CH | H | EtC(O) |
| 70 | CF$_3$ | 3,5-diCl—Ph | 6-CN | H | CH≡C | H | c-PrC(O) |
| 71 | CF$_3$ | 3,5-diCl—Ph | 2-Cl | H | H | H | PhC(O) |
| 72 | CF$_3$ | 3,5-diCl—Ph | 6-Cl | H | Me | H | CH$_3$CH(OMe)CH$_2$C(O) |
| 73 | CF$_3$ | 3,5-diCl—Ph | 2-Br | Cl | Et | H | N≡CCH$_2$CH$_2$C(O) |
| 74 | CF$_3$ | 3,5-diCl—Ph | 6-Br | Cl | CF$_3$ | H | CH$_3$C(OCH$_2$CH$_2$O)CH$_2$C(O) |
| 75 | CF$_3$ | 3,5-diCl—Ph | 2-I | Cl | Ph | H | CH$_3$OC(O) |
| 76 | CF$_3$ | 3,5-diCl—Ph | 6-I | Cl | c-Pr | H | i-PrOC(O) |
| 77 | CF$_3$ | 3,5-diCl—Ph | 2-F | Br | c-Hex | H | t-BtOC(O) |
| 78 | CF$_3$ | 3,5 diCl—Ph | 6-F | Br | PhCH$_2$ | H | H |
| 79 | CF$_3$ | 3,5-diCl—Ph | 2-NO$_2$ | I | CH2=CH | H | MeC(O) |
| 80 | CF$_3$ | 3,5-diCl—Ph | 6-NO$_2$ | I | CH≡C | H | EtC(O) |
| 81 | CF$_3$ | 3,5-diCl—Ph | 2-OH | F | H | H | c-PrC(O) |
| 82 | CF$_3$ | 3,5-diCl—Ph | 6-OH | F | Me | H | PhC(O) |
| 83 | CF$_3$ | 3,5-diCl—Ph | 2-SH | NO$_2$ | Et | H | CH$_3$CH(OMe)CH$_2$C(O) |
| 84 | CF$_3$ | 3,5-diCl—Ph | 6-SH | NO$_2$ | CF$_3$ | H | N≡CCH$_2$CH$_2$C(O) |
| 85 | CF$_3$ | 3,5-diCl—Ph | 2-NH$_2$ | OH | Ph | H | CH$_3$C(OCH$_2$CH$_2$O)CH$_2$C(O) |
| 86 | CF$_3$ | 3,5-diCl—Ph | 6-NH$_2$ | OH | c-Pr | H | CH$_3$OC(O) |
| 87 | CF$_3$ | 3,5-diCl—Ph | 2-N(Me)$_2$ | SH | c-Hex | H | i-PrOC(O) |
| 88 | CF$_3$ | 3,5-diCl—Ph | 6-N(Me)$_2$ | SH | PhCH$_2$ | H | t-BtOC(O) |
| 89 | CF$_3$ | 3,5-diCl—Ph | 2-CN | NH$_2$ | CH2=CH | H | H |
| 90 | CF$_3$ | 3,5-diCl—Ph | 6-CN | NH$_2$ | CH≡C | H | MeC(O) |
| 91 | CF$_3$ | 3,5-diCl—Ph | 2-Cl | N(Me)$_2$ | H | H | EtC(O) |
| 92 | CF$_3$ | 3,5-diCl—Ph | 6-Cl | N(Me)$_2$ | Me | H | c-PrC(O) |
| 93 | CF$_3$ | 3,5-diCl—Ph | 2-Br | CN | Et | H | PhC(O) |
| 94 | CF$_3$ | 3,5-diCl—Ph | 6-Br | CN | CF$_3$ | H | CH$_3$CH(OMe)CH$_2$C(O) |
| 95 | CF$_3$ | 3,5-diCl—Ph | 2-I | H | Ph | H | N≡CCH$_2$CH$_2$C(O) |
| 96 | CF$_3$ | 3,5-diCl—Ph | 6-I | H | c-Pr | H | CH$_3$C(OCH$_2$CH$_2$O)CH$_2$C(O) |
| 97 | CF$_3$ | 3,5-diCl—Ph | 2-F | H | c-Hex | H | CH$_3$OC(O) |
| 98 | CF$_3$ | 3,5-diCl—Ph | 6-F | H | PhCH$_2$ | H | i-PrOC(O) |
| 99 | CF$_3$ | 3,5-diCl—Ph | 2-OH | H | CH2=CH | H | t-BtOC(O) |
| 100 | CF$_3$ | 3,5-diCl—Ph | 6-OH | H | CH≡C | H | H |

2. Manufacturing Method

The compounds expressed by formula (I) of the present invention may be synthesized based on known reactions. For example, they may be manufactured by the methods shown below.

(Manufacturing Method 1)

Among the compounds expressed by the aforementioned formula (I), compounds expressed by formula (I-1) wherein D is a methylene group may be manufactured as follows.

[Chemical formula 17]

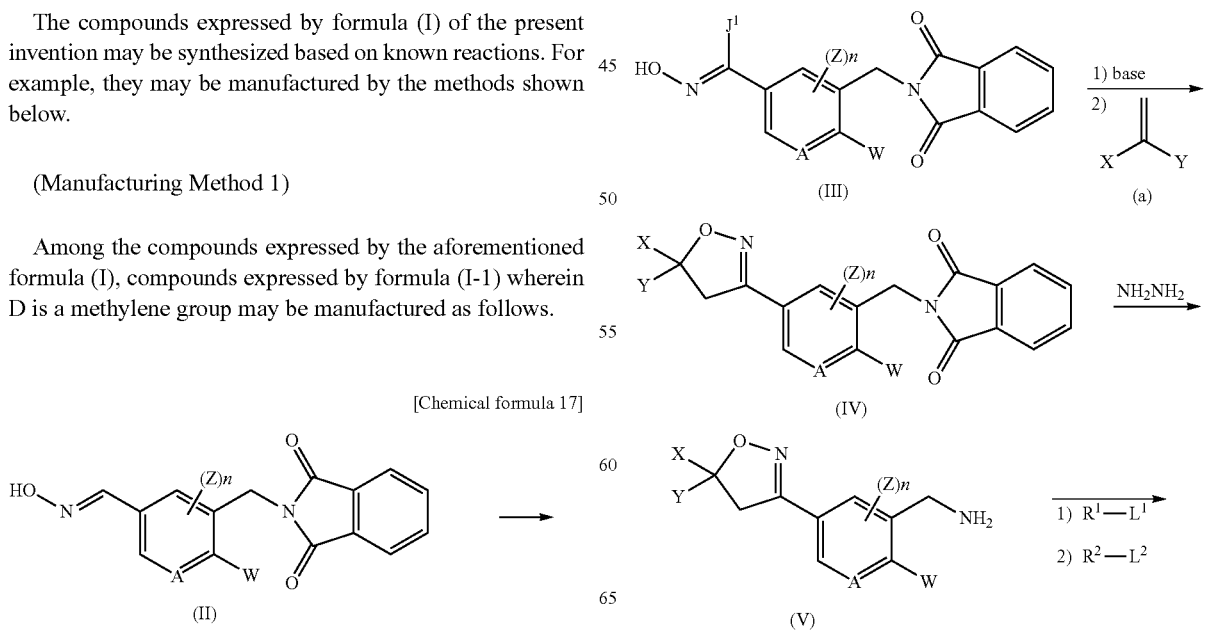

-continued

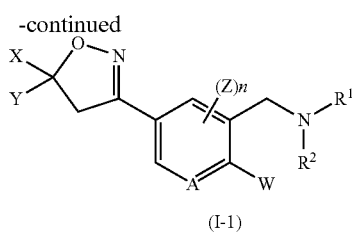

(I-1)

(In the formula, A, X, Y, Z, W, $R^1$, $R^2$, and n express the same meanings described above, $J^1$ expresses a halogen atom, and $L^1$ and $L^2$ express elimination groups such as halogen atoms and the like. However, $R^1$ and $R^2$ exclude hydrogen atoms in here.)

That is, first, a halogenation agent is made to act upon a compound expressed by formula (II) to obtain a compound expressed by formula (III).

As the halogenation agent that is employed, one may cite N-halogenosuccinimide such as N-chlorosuccinimide and N-bromosuccinimide; alkali metal salt of hypohalous acid such as sodium hypochlorite; esters of hypohalous acid such as hydrochlorite-t-butylester; halogen carrier such as chlorine gas; and the like.

It is preferable that this reaction occur in a solvent. There are no particular limitations on the employed solvent provided that it is inert in the reaction. For example, one may cite aromatic hydrocarbons such as benzene, toluene, and xylene; aliphatic hydrocarbons such as hexane and heptane; alicyclic hydrocarbons such as cyclohexane; aromatic halogenated hydrocarbons such as chlorobenzene and dichlorobenzene; aliphatic halogenated hydrocarbons such as dichloromethane, chloroform, carbon tetrachloride, 1,2-dichloroethane, 1,1,1-trichloroethane, trichloroethylene, and tetrachloroethylene; ethers such as diethyl ether, 1,2-dimethoxyethane, tetrahydrofuran, and 1,4-dioxane; esters such as ethyl acetate and ethyl propionate; amides such as N,N-dimethyl formamide, N,N-dimethylacetamide, and N-methyl-2-pyrrolidone; alcohols such as methanol, ethanol, and ethylene glycol; carboxylic acids such as acetic acid and propionic acid; acetonitrile; water; and the like.

These solvents may be used alone, or in mixtures of two or more.

The obtained compounds expressed by formula (III) may normally be provided to the following reactions without being isolated.

Next, after subjecting the compound expressed by formula (III) to the action of a base, a compound expressed by formula (IV) may be obtained by the action of a compound expressed by formula (a).

As the base to be employed, one may cite, for example, alkali metal hydroxides such as sodium hydroxide and potassium hydroxide; alkali metal carbonates such as sodium carbonate and potassium carbonate; alkali metal bicarbonates such as sodium bicarbonate and potassium bicarbonate; organic base such as triethylamine, imidazole, and 1,8-diazabicyclo[5.4.0]-7-undecene; and the like.

It is preferable that this reaction be conducted in a solvent. There are no particular limitations on the employed solvent provided that it is inert in the reaction, and one may cite, for example, the same solvents used in the reaction to obtain the aforementioned compound expressed by formula (III).

With respect to the usage amount of the compound expressed by formula (a), it is normally a 1-5 equivalent relative to the compound expressed by formula (III).

Subsequently, a compound expressed by formula (V) may be obtained by reacting the aforementioned compound expressed by formula (IV) with hydrazine according to conventional methods.

Furthermore, a compound expressed by formula (I-1) may be obtained by reacting compounds expressed by the formula $R^1$-$L^1$ and the formula $R^2$-$L^2$ with the compound expressed by formula (V) in a stepwise manner.

The aforementioned compound expressed by formula (II) may be obtained, for example, as follows.

[Chemical formula 18]

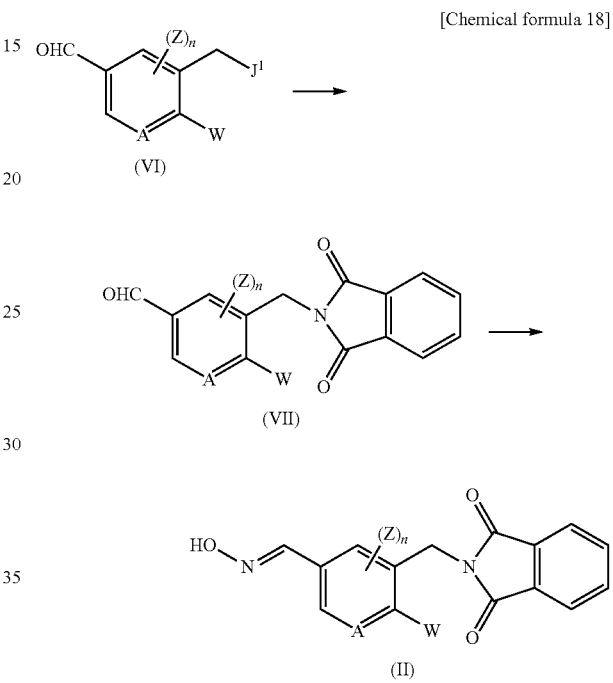

(In the formula, A, Z, W, and n have the same meanings described above. $J^1$ expresses a halogen atom.) That is, first, a compound expressed by formula (VII) is obtained by reacting a metal salt of phthalimide (potassium phthalimide or the like) with an aldehyde compound expressed by formula (VI) according to conventional methods.

Subsequently, a compound expressed by formula (II) is obtained by reacting hydroxylamine with the obtained compound expressed by formula (VII).

There are no particular limitations on the solvent to be used in this reaction provided that it is inert in the reaction, and one may cite alcohols such as ethanol and i-propyl alcohol and the like; water; mixed solvents of these; and so on.

Otherwise, with respect to this reaction, it is also acceptable to generate free hydroxylamine in the reaction system by conducting addition to the reaction solution in the form of hydroxylamine salt (hydroxylamine hydrochloride or the like) that is easy to handle, adding thereto base such as sodium acetate, sodium hydroxide, triethylamine or the like.

(Manufacturing Method 2)

Of the aforementioned compounds expressed by formula (I), it is also possible to manufacture a compound expressed by formula (I-1) wherein D is a methylene group by another method.

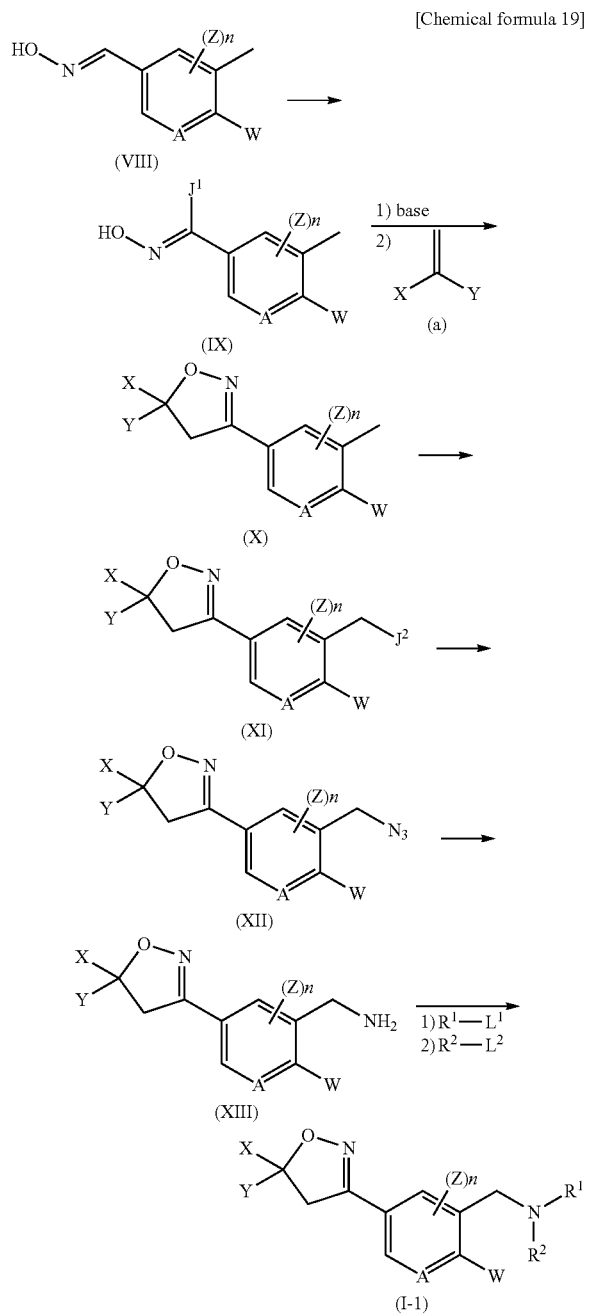

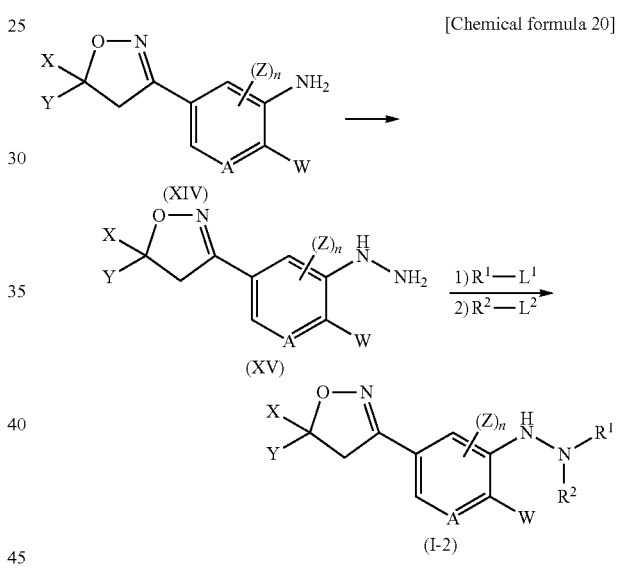

(In the formula, A, X, Y, Z, W, $R^1$, $R^2$, and n have the same meanings described above; $J^1$ and $J^2$ express halogen atoms; and $L^1$ and $L^2$ express elimination groups such as halogen atoms or the like. However, $R^1$ and $R^2$ herein exclude hydrogen atoms.)

The halogenation of compound (VIII), the reaction of compound (IX) with a base and with a compound expressed by (a), and the halogenation of compound (X) are identical to the aforementioned manufacturing method 1. Subsequently, a compound expressed by formula (XII) is obtained by azidation compound (XI) in a solvent.

As the azidation agent, one may cite, for example, metal azides such as lithium azide and sodium azide; silicon azide compounds such as trimethylsilyl azide; and phosphoryl azide compounds such as diphenylphosphoryl azide.

As the solvent employed in the azidation reaction, an aprotic polar solvent is preferable, and one may cite, for example, acetone, acetonitrile, N,N-dimethyl formaldehyde, dimethyl sulfoxide, and the like.

The azide compound expressed by formula (XII) is made into an amine compound expressed by formula (XIII) by the method that uses hydrogen gas and metal catalyst, the method that uses tin (II) chloride dihydrate, the method that uses a reducing agent such as $LiAlH_4$, or the like. As the employed solvent, one may cite methanol, ethanol, isopropyl alcohol, and the like.

Furthermore, as in the aforementioned manufacturing method 1, a compound expressed by formula (I-1) may be obtained by reacting compounds expressed by the formula $R^1$-$L^1$ and the formula $R^2$-$L^2$ with the compound expressed by formula (XIII) in a stepwise manner.

(Manufacturing Method 3)

With respect to a compound expressed by formula (I), a compound expressed by formula (I-2) wherein D is a group expressed by the formula —NH— may be manufactured as follows.

(In the formula, X, Y, Z, W, $R^1$, $R^2$, A, and n have the same meanings described above.)

That is, first, sodium nitrite is reacted with a compound expressed by formula (XIV), after which a hydrazine compound (XV) is obtained by the action of a reducing agent such as tin chloride. Subsequently, a compound expressed by the target formula (I-2) may be obtained by reacting a compound expressed by the formula $R^1$-$L^1$ and a compound expressed by the formula $R^2$-$L^2$ with this compound in a stepwise manner.

The hydrazine compound (XV) may be isolated in the form of hydrochloride salt or sulfate salt.

A compound expressed by formula (XIV) may be manufactured in the same way as the method recorded in Japanese Unexamined Patent Application, First Publication No. 2007-016017.

There are no limitations on the salts of compounds expressed by formula (I) provided that they are horticulturally permissible. For example, one may cite inorganic acid salts of compounds expressed by formula (I) such as hydrochloride salts, nitrate salts, sulfate salts, and phosphate salts; and organic acid salts of acetic acid, propionic acid, lactic acid, and the like.

Salts of compounds expressed by formula (I) may be manufactured, for example, by causing an inorganic acid or organic acid to act upon a compound expressed by formula (I).

With respect to whichever reaction, if purification of the product is required after termination of the reaction and following the normal after-treatment operations, the target substance may be isolated by conducting purification by a purification means known to those skilled in the art such as distillation, recrystallization, or column chromatography.

3) Pest Control Agents

The compounds and their salts of the present invention obtained in the foregoing manner may be utilized for the control of agricultural pests, hygiene pests, stored grain pests, clothing pests, household pests, and the like, and may have adulticidal, pupicidal, larvicidal, or ovicidal activity.

Accordingly, as described below, the compounds of the present invention are useful as effective ingredients of pest control agents.

Among the compounds of the present invention, some exhibit germicidal, herbicidal, and plant growth regulatory activity. In addition, among intermediate compounds of the compounds of the present invention, some exhibit pesticidal and acaricidal activity.

Moreover, the compounds of the present invention may also be used as antifoulants that serve to prevent adhesion of aquatic organisms to marine implements such as ship bottoms and fishing nets.

A pest control agent of the present invention may contain a single type or two or more types of the compounds of the present invention as its active ingredient. It is preferable that the pest control agent of the present invention be an insecticidal agent or an acaricidal agent.

One may cite the following as representative examples of agricultural pests, hygiene pests, stored grain pests, clothing pests, household pests, or the like.

Lepidopteran pests such as, for example, *Spodoptera litura, Mamestra brassicae, agrotis ipsilon*, green caterpillars, *Autographa nigrisigna, Plutella xylostella, Adoxophyes honmai, Homona magnanima, Carposina sasakii, Grapholita molesta, Phyllocnistis citrella, Caloptilia theivora, Phyllonorycter ringoniella, Lymantria dispar, Euproctis pseudoconspersa, Chilo suppressalis, Cnaphalocrocis medinalis, Ostrinia nubilalis, Hyphantria cunea, Cadra cautella*, genus *Heliothis*, genus *Helicoverpa*, genus *Agrothis, Tinea translucens, Cydia pomonella*, and *Pectinophora gossypiella;* hemipteran pests such as, for example, *Myzus persicae, Aphis gossypii, Lipaphis erysimi, Rhopalosiphum padi, Riptortus clavatus, Nezara antennata, Unaspis yanonensis, Pseudococcus comstocki, Trialeurodes vaporariorum, Bemisia tabaci, Bemisia argentifolii, Psylla pyrisuga, Stephanitis nashi, Nilaparuata lugens, Laodelphax stratella, Sogatella furcifera*, and *Nephotettix cincticeps;* coleopteran pests such as, for example, *Phyllotreta striolata, Aulacophora femoralis, Leptinotarsa decemlineata, Lissorhoptrus oryzophilus, Sitophilis zeamais, Callosobruchus chinensis, Popillia japonica, Anomala rufocuprea*, genus *Diabrotica, Lasioderma serricorne, Lyctus brunneus, Monochamus alternatus, Anoplophora malasiaca*, genus *Agriotis, Epilachna vigintioctopunctata, Tenebroides mauritanicus*, and *Anthonomus grandis;* dipteran pests such as, for example, *Musca domestica, Calliphora lata, Boettcherisca peregrine, Zeugodacus cucurbitae, Bactrocera dorsalis, Delia platura, Agromyza oryzae, Drosophila melanogaster, Stomoxys calcitrans, Culex tritaeniorhynchus, Aedes aegypti*, and *Anopheles sinensis;* thysanopteran pests such as, for example, *Thrips palmi*, and *Scirtothrips dorsalis;* hymenopteran pests such as, for example, *Monomorium pharaonis, Vespa simillima xanthoptera*, and *Athalia rosae ruficornis;* orthopteran pests such as, for example, *Locusta migratoria, Blattella germanica, Periplaneta americana*, and *Periplaneta fuliginosa;* isopteran pests such as, for example, *Coptotermes formosanus* and *Reticulitermes speratus;* siphonapteran pests such as, for example, *Pulex irritans* and *Ctenocephalides felis;* phthirapteran pests such as, for example, *Pediculus humanus;*

Acarina such as *Tetranychus urticae, Tetranychus cinnabarinus, Tetranychus kanzawai, Panonychus citri, Panonychus ulmi, Aculops pelekassi, Aculus schlechtendali, Polyphagotarsonemus latus*, genus *Brevipalpus*, genus *Eotetranichus, Rhizoglyphus robini, Tyrophagus putrescentiae, Dermatophagoides farinae, Boophilus microplus*, and *Haemaphysalis longicornis;* and plant parasitic nematodes such as *Meloidogyne incognita, Pratylenchus* spp., *Heterodera glycines, Aphelenchoides besseyi*, and *Bursaphelenchus xylophilus.*

Of these, pests to which application is particularly preferable are lepidopteran pests, hemipteran pests, acarina, thysanopteran pests, and coleopteran pests.

In recent years, the resistance of many pests such as diamondback moths, planthoppers, leafhoppers and aphids to organophosphorous agents, carbamate agents and acaricides has grown, the impotency of such chemical agents has become problematic, and there has been increasing demand for chemical agents that are effective relative to resistant strains of pests and mites. The compounds of the present invention are chemical agents that have excellent pesticidal and miticidal effects not only relative to susceptible strains, but also relative to strains of pests that are resistant to organophosphorous agents, carbamate agents, and pyrethroid agents, as well as strains of mites that are resistant to miticidal agents. Moreover, the pest control agents of the present invention are chemical agents that have few harmful effects, low toxicity relative to fish and mammals, and high stability.

When the pest control agents of the present invention are practically applied, one may use a single type or two or more types of the compounds of the present invention as is without addition of other components, but they are normally further mixed with a solid carrier, liquid carrier, or gaseous carrier, or impregnated into a base material such as porous ceramic sheet or nonwoven cloth, with addition of surfactants and other adjuvants as necessary, and formulated for use in a form that can be assumed by common agrochemicals for the purpose of use as an agrochemical, that is, a form such as a wettable powder, granular agent, dust agent, emulsion agent, water-soluble agent, suspension agent, granular wettable powder, flowable, aerosol, smoke and misting agent, heat steam agent, fumigant, poison bait, or microcapsule.

Additives and carriers which may be employed in the case where a solid formulation is desired include vegetable powders such as soybean or wheat flour and the like; mineral micropowders such as diatom clay, apatite, plaster, talc, bentonite, pyrophyllite, clay, and the like; organic and inorganic compounds such as benzoate soda, urea, Glauber's salt, and the like. Solvents which may be employed in the case where a liquid agent is desired include petroleum distallates such as kerosene, xylene, solvent naphtha and the like; cyclohexane, cyclohexanone, dimethylformamide, dimethylsulfoxide, alcohol, acetone, methylisobutylketone, mineral oil, vegetable oil, water, and the like. As a gas carrier which may be employed in the spray agent, one may use butane gas, LG, dimethyl ether, and carbon dioxide gas.

As a base material for poison bait, one may use, for example, bait ingredients such as grain flour, vegetable oil, sugar, and crystalline cellulose; antioxidants such as dibutylhydroxytoluene and nordihydroguacetic acid; preservatives such as dehydroacetic acid; agents which prevent children and pets from eating by mistake such as powdered capsicum; and vermin attracting perfumes such as cheese perfume and onion perfume.

Surfactants may be added as necessary in order to achieve a uniform and stable morphology in these formulations. There are no particular limitations on surfactants, and one may cite, for example, nonionic surfactants such as alkyl ether to which polyoxyethylene is added, higher fatty acid ester to which polyoxyethylene is added, sorbitan higher fatty acid ester to which polyoxyethylene is added, and tristyrylphenyl ether to which polyoxyethylene is added, sulfate ester salt of alkylphenyl ether to which polyoxyethylene is added, alkylnaphthalene sulfonate, polycarboxylate, lignin sulfonate, formaldehyde condensate of alkyl naphthalene sulfonate, copolymer of isobutylene-maleic anhydride, and the like.

There are no particular limitations on the amount of active ingredient in the pest control agent of the present invention, but 0.01-90 weight % is preferable, and 0.05-85 weight % is particularly preferable.

In the case where the pest control agent of the present invention is to be used for agricultural purposes, the formulation may be prepared as a wettable powder, emulsion agent, suspension agent, flowable agent, water-soluble agent, granular wettable powder, or the like. These formulations may be used by diluting to a prescribed concentration to obtain a solution, suspension or emulsion and spraying them on plants or soil, or in the case of a dust formulation or granular formulation, it may be used by directly spraying them on plants or soil.

In the case where the compound of the present invention is used as a pest control agent for the prevention of epidemics, the formulation may be prepared as an emulsion agent, wettable powder, flowable agent, or the like, and these formulations may be applied after dilution with water to a prescribed concentration. In the case where the formulation is prepared as an oil agent, aerosol, smoke and misting agent, poison bait, mite control sheet, or the like, it may be directly applied.

In the case where compounds of the present invention are used as pest control agents for the control of external parasites of animals such as livestock including cows and pigs, or pets including dogs and cats, the normal formulations of compounds of the present invention are used by methods known to those skilled in the veterinary art.

With respect to these methods, in the case where, for example, systemic control is desired, one may cite methods of administration by tablet, capsule, immersion fluid, feed intermixture, suppository, injection (intramuscular, subcutaneous, intravenous, intraperitoneal, and so on), and the like; in the case where non-systemic control is desired, one may cite methods of administration of oleaginous or aqueous solutions by spray, pour-on, spot-on, and the like; as well as methods of application of resin formulations molded into an appropriate shape such as a collar or ear tag. In these cases, compounds of the present invention may be used in a proportion of 0.01-1000 mg relative to 1 kg of an ordinary host animal.

It goes without saying that a compound of the present invention is sufficiently effective when used alone, and it may also be used in a mixture or combination with one or more other types of pest control agent, bactericide, insecticide/acaricide, nematicide, soil pest control agent, herbicide, plant growth regulation agent, synergist, fertilizer, soil improver, animal feed, and so on.

Representative examples of active ingredients of bactericides, insecticides, acaricides, nematicides, soil pest control agents, synergists, plant growth regulation agents, and the like which can be mixed or combined with a compound of the present invention are shown below.

Fungicides (common names; including some still in the application stage): anilinopyrimidine compounds such as mepanipyrim, pyrimethanil, and cyprodinil; pyridinamine compounds such as fluazinam;

azole compounds such as triadimefon, bitertanol, triflumizole, etaconazole, propiconazole, penconazole, flusilazole, myclobutanil, cyproconazole, tebuconazole, hexaconazole, furconazole-cis, prochloraz, metconazole, epoxiconazole, tetraconazole, oxpoconazole fumarate, sipconazole, prothioconazole, triadimenol, flutriafol, difenoconazole, fluquinconazole, fenbuconazole, bromuconazole, diniconazole, tricyclazole, probenazole, simeconazole, pefurazoate, ipconazole, imibenconazole, and imazalil;

quinoxaline compounds such as quinomethionate; dithiocabamate compounds such as maneb, zineb, mancozeb, polycarbamate, metiram, propineb, ferbam, nabam, metam, thiram, and ziram;

organic chlorine compounds such as fthalide, chlorothalonil, and quintozene; imidazole compounds such as benomyl, thiophanate-methyl, carbendazim, thiabendazole, fuberiazole, and cyazofamid;

cyano acetamide compounds such as cymoxanil;

phenylamide compounds such as metalaxyl, metalaxyl-M, mefenoxam, oxadixyl, ofurace, benalaxyl, benalaxyl-M, furalaxyl, and cyprofuram;

sulfenic acid compounds such as dichlofluanid;

nitrophenyl compounds such as dinocap;

copper compounds such as cuprichydroxide or oxine copper;

isoxazole compounds such as hymexazol;

organic phosphorus compounds such as fosetyl-A1, tolcofos-methyl, S-benzyl O,O-diisopropylphosphorothioate, O-ethyl S,S-diphenylphosphorodithioate, and aluminum ethylhydrogen phosphonate;

N-halogenothioalkyl compounds such as captan, captafol, and folpet;

dicarboxylmide compounds such as procymidone, iprodione, and vinclozolin;

benzanilide compounds such as flutolanil, mepronil, zoxamid, and tiadinil;

anilide compounds such as carboxin, oxycarboxin, thifluzamide, penthiopyrad, boscalid, fluopicolide, fluopyram, and bixafen;

piperazine compounds such as triforine;

pyridine compounds such as pyrifenox;

carbinol compounds such as fenarimol and flutriafol;

piperidine compounds such as fenpropidine;

morpholine compounds such as fenpropimorph and tridemorph;

organotin compounds such as fentin hydroxide and fentin acetate;

urea compounds such as pencycuron;

cinnamic acid compounds such as dimethomorph, flumorph, and flumetover;

phenylcarbamate compounds such as diethofencarb;

cyanopyrrole compounds such as fludioxonil and fenpiclonil;
strobilurin compounds such as azoxystrobin, kresoxim-methyl, metominofen, metominostrobin, trifloxystrobin, picoxystrobin, oryzastrobin, dimoxystrobin, pyraclostrobin, and fluoxastrobin;
oxazolidinone compounds such as famoxadone;
thiazolecarboxamide compounds such as ethaboxam;
silylamide compounds such as silthiopham;
amino acid amidecarbamate compounds such as iprovalicarb and benthiavalicarbisopropyl;
imidazolidine compounds such as fenamidone;
hydroxanilide compounds such as fenhexamid;
benzenesulfonamide compounds such as flusulfamide;
oxime ether compounds such as cyflufenamid;
phenoxyamide compounds such as fenoxanil;
antibiotics such as validamycin, kasugamycin, and polyoxin;
guanidine compounds such as iminoctadine;
and other compounds such as tolyfluanid, isoprothiolane, pyroquilon, diclomezine, quinoxyfen, propamocarb hydrochloride, spiroxamine, chloropicrin, dazomet, metam-sodium, nicobifen, metrafenone, UBF-307, diclocymet, proquinazid, amisulbrom, pyribencarb mandipropamid, 5-chlor-7-(4-methyl-piperidin-1-yl)-6-(2,4,6-trifluor-phenyl)-[1,2,4]triazolo[1,5-a]pyrimidin, and OK-5203.

Pesticides, acaricides, nematicides, or soil pest control agents (common names; including some still in the application stage): organic phosphate ester compounds such as profenofos, dichlorvos, fenamiphos, fenitrothion, EPN, diazinon, chlorpyrifos-methyl, acephate, prothiofos, fosthiazate, phosphocarb, cadusafos, disulfoton, chlorpyrifos, demeton-S-methyl, dimethoate, methamidophos, isoxathion, isofenphos, ethion, etrimfos, quinalphos, dimethylvinphos, sulprofos, thiometon, vamidothion, pyraclofos, pyridaphenthion, pirimiphos-methyl, propaphos, phosalone, formothion, malathion, tetrachlovinphos, chlorfenvinphos, cyanophos, trichlorfon, methidathion, phenthoate, ESP, azinphos-methyl, fenthion, heptenophos, methoxychlor, paration, monocrotophos, imicyafos, parathion-methyl, terbufos, phospamidon, phosmet, and phorate;
carbamate compounds such as carbaryl, propoxur, aldicarb, carbofuran, thiodicarb, methomyl, oxamyl, ethiofencarb, pirimicarb, fenobucarb, carbosulfan, benfuracarb, bendiocarb, furathiocarb, isoprocarb, metolcarb, xylylcarb, XMC, and fenothiocarb;
nereistoxin derivatives such as cartap, thiocyclam, bensultap and thiosultap-sodium; organic chlorine compounds such as dicofol, tetradifon, endosulfan, dienochlor and dieldrin;
organic metal compounds such as fenbutatin oxide and cyhexatin;
pyrethroid compounds such as fenvalerate, permethrin, cypermethrin, deltamethrin, cyhalothrin, tefluthrin, ethofenprox, cyfluthrin, fenpropathrin, bifenthrin, flucythrinate, fluvalinate, cycloprothrin, lambda-cyhalothrin, pyrethrins, esfenvalerate, tetramethrin, resmethrin, protrifenbute, zeta-cypermethrin, acrinathrin, alpha-cypermethrin, allethrin, gamma-cyhalothrin, theta-cypermethrin, tau-fluvalinate, tralomethrin, profluthrin, beta-cypermethrin, beta-cyfluthrin, metofluthrin, and phenothrin;
benzoylurea compounds such as diflubenzuron, chlorfluazuron, teflubenzuron, flufenoxuron, lufenuron, novaluron, triflumuron, hexaflumuron, noviflumuron, bistrifluoron and fluazuron;
juvenile hormone-like compounds such as methoprene, pyriproxyfen, fenoxycarb and diofenolan;
pyridazinone compounds such as pyridaben;
pyrazole compounds such as fenpyroximate, fipronil, tebufenpyrad, ethiprole, tolfenpyrad, acetoprole, pyrafluprole, and pyriprole;
neonicotinoids such as imidacloprid, nitenpyram, acetamiprid, thiacloprid, thiamethoxam, clothianidin, dinotefuran, and nithiazine;
hydrazine compounds such as tebufenozide, methoxyfenozide, chromafenozide, and halofenozide;
and other compounds such as flonicamid, buprofezin, hexythiazox, amitraz, chlordimeform, silafluofen, triazamate, pymetrozine, pyrimidifen, chlorfenapyr, indoxacarb, acequinocyl, etoxazole, cyromazine, 1,3-dichloropropene, diafenthiuron, benclothiaz, flufenerim, pyridalyl, spirodiclofen, bifenazate, spiromesifen, spirotetramat, propargite, clofentezine, fluacrypyrim, metaflumizone, flubendiamide, cyflumetofen, chlorantraniliprole, cyenopyrafen, pyrifluquinazon, fenazaquin, amidoflumet, chlorobenzoate, sulfluramid, hydramethylnon, metaldehyde, and ryanodine.

Further, one may cite: microbial agricultural chemicals such as *Bacillus thuringienses aizawaiii, Bacillus thuringienses kurstaki, Bacillus thuringienses israelensis, Bacillus thuringienses japonensis, Bacillus thuringienses tenebrionis*, insecticidal crystal protein produced by *Bacillus thuringienses*, insect viruses, etomopathogenic fungi, and nematophagousiii fungi; antibiotics or semisynthetic antibiotics such as avermectin, emamectin-benzoate, milbemectin, spinosad, ivermectin, and lepimectin;

natural products such as azadirachtin and rotenone;

synergists such as piperonyl butoxide;

and repellents such as deet; and so on.

Plant growth regulators such as gibberellins (e.g., gibberellins A3, gibberellins A4, and gibberellin A7), IAA, NAA, and the like.

WORKING EXAMPLES

Next, the present invention is described in further detail with reference to working examples, but the present invention is in no way limited by the following working examples.

SYNTHETIC EXAMPLES

Working Example 1

Manufacture of N-{2-fluoro-5-[5-(3,5-dichlorophenyl)-5-trifluoromethyl-4,5-dihydroisoxazole-3-yl]-benzyl}-propionic acid amide (Manufacturing step 1)

Manufacture of 5-(3,5-dichlorophenyl)-3-(4-fluoro-3-methylphenyl)-5-trifluoromethyl-4,5-dihydroisoxazole

[Chemical formula 21]

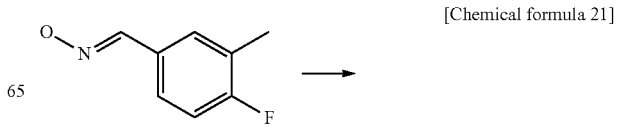

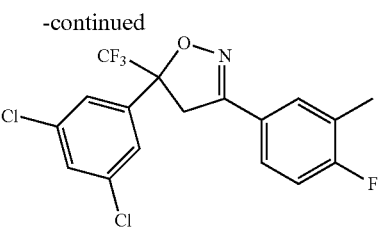

6.2 g of 4-fluoro-3-methylbenzaldehyde oxime were dissolved in 50 ml of 1,2-dimethoxy ethane, 6.5 g of N-chlorosuccinimide were added, and stirring was conducted for two hours at 70° C. Subsequently, the reaction solution was cooled to 0° C., 9.8 g of 3,5-dichloro-1-(1-trifluoromethyl ethenyl)benzene, 10.2 g of potassium bicarbonate, and 10 ml of water were added, and stirring was conducted overnight at room temperature. The reaction solution was poured into ice water, extracted with ethyl acetate, and washed with water and brine, and dried with anhydrous magnesium sulfate. The solvent was removed to vacuum distillation, and the obtained residue was purified by silica gel column chromatography (eluent: ethyl acetate/n-hexane=1/9) to obtain 11.1 g of the target compound. Yield was 69%; $^1$H-NMR (CDCl$_3$, δppm); 2.31 (s, 3H), 3.67 (d, 1H), 4.05 (d, 1H), 7.05 (t, 1H), 7.42-7.54 (m, 5H).

(Manufacturing step 2)

Manufacture of 2-fluoro-5-[5-(3,5-dichlorophenyl)-5-trifluoromethyl-4,5-dihydroisoxazole-3-yl]-benzyl amine

[Chemical formula 22]

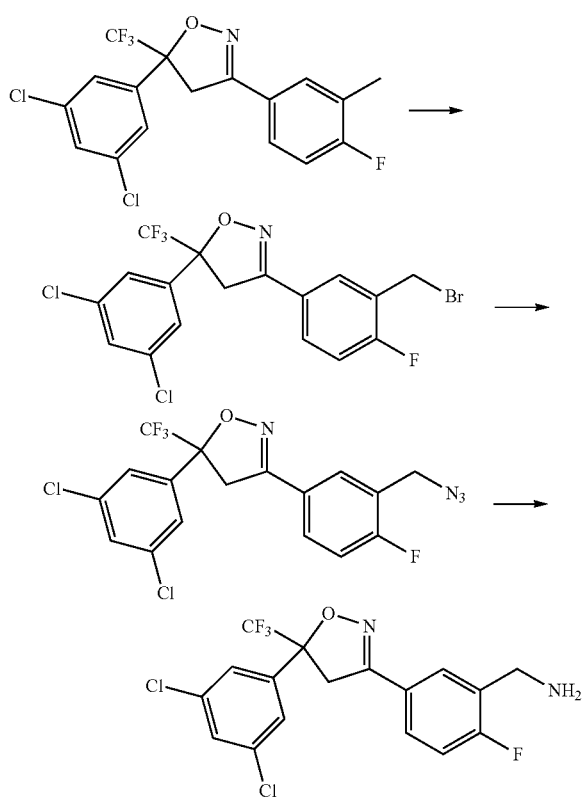

11.1 g of 5-(3,5-dichlorophenyl)-3-(4-fluoro-3-methylphenyl)-5-trifluoromethyl-4,5-dihydroisoxazole were dissolved in 100 ml of carbon tetrachloride, 6.0 g of N-bromosuccinimide and 0.2 g of benzoyl peroxide were added, and heat reflux was conducted overnight. The reaction solution was cooled to room temperature, and filtered, and the filtrate was removed to vacuum concentration to obtain unpurified 3-(3-bromomethyl-4-fluorophenyl)-5-(3,5-dichlorophenyl)-5-trifluoromethyl-4,5-dihydroisoxazole. The obtained unpurified 3-(3-bromomethyl-4-fluorophenyl)-5-(3,5-dichlorophenyl)-5-trifluoromethyl-4,5-dihydroisoxazole was dissolved in 120 ml of N,N-dimethylformamide, 7.3 g of sodium azide were added, and stirring was conducted overnight at room temperature. The reaction solution was poured into ice water, extracted with ethyl acetate, and washed with water and brine, and dried with anhydrous magnesium sulfate. The solvent was removed to vacuum distillation, and unpurified 3-(3-azidemethyl-4-fluorophenyl)-5-(3,5-dichlorophenyl)-5-trifluoromethyl-4,5-dihydroisoxazole was obtained. The obtained unpurified 3-(3-azidemethyl-4-fluorophenyl)-5-(3,5-dichlorophenyl)-5-trifluoromethyl-4,5-dihydroisoxazole was dissolved in 200 ml of methanol, 12.7 g of tin (II) chloride dehydrate was added under icing, and stirring was conducted overnight at room temperature. After subjecting the reaction solution to vacuum concentration, a 10% sodium hydroxide aqueous solution was added to alkalize, chloroform was added, and celite filtration was conducted. The filtrate was extracted with chloroform, and washed with water and brine, and dried with anhydrous magnesium sulfate. The solvent was removed to vacuum distillation, and the obtained residue was purified by silica gel column chromatography (eluent: triethyl amine/methanol/ethyl acetate=1/1/8) to obtain 5.0 g of the target compound. Yield; 43%; $^1$H-NMR (CDCl$_3$, δppm); 3.70 (d, 1H), 3.94 (s, 1H), 4.09 (d, 1H), 7.09 (t, 1H), 7.42-7.71 (m, 5H).

(Manufacturing step 3)

Manufacture of N-{2-fluoro-5-[5-(3,5-dichlorophenyl)-5-trifluoromethyl-4,5-dihydroisoxazole-3-yl]-benzyl}propionicamide

[Chemical formula 23]

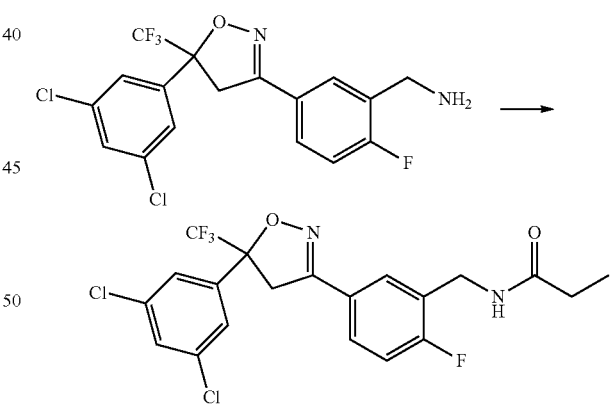

1.3 g of 2-fluoro-5-[5-(3,5-dichlorophenyl)-5-trifluoromethyl-4,5-dihydroisoxazole-3-yl]-benzyl amine was dissolved in 20 ml of dichloromethane, 0.56 g of pyridine was added, and 0.5 g of anhydrous propionic acid was added under icing. After the reaction solution was returned to room temperature, and stirred overnight, the reaction solution was poured into ice water, extracted with chloroform, and washed with water and brine, and dried with anhydrous magnesium sulfate. The solvent was removed to vacuum distillation, and the obtained residue was purified by silica gel column chromatography (eluent: ethyl acetate/n-hexane=1/1) to obtain 1.1 g of the target compound. Yield; 74%; $^1$H-NMR (CDCl$_3$, δppm); 1.17 (t, 3H), 2.25 (q, 2H), 3.68 (d, 1H), 4.07 (d, 1H), 4.49 (d, 2H), 5.84 (brs, 1H), 7.11 (t, 1H), 7.42-7.67 (m, 5H).

Working Examples 2-61

The compounds of working examples 2-61 were synthesized in the same manner as working example 1 by known methods. The structure and physical properties of the manufactured compounds of the present invention, including the compound obtained in working example 1, are shown below.

In the below tables, the abbreviations have the following meanings. Ph: phenyl, Me: methyl, Et: ethyl, i-Pr: isopropyl, c-Pr: cyclopropyl, t-Bt: tertiary butyl.

[Chemical formula 24]

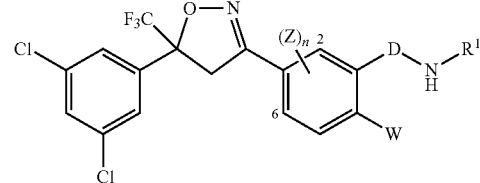

TABLE 10

| Working example number | D | (Z)n | W | R¹ | Physical properties |
|---|---|---|---|---|---|
| 1 | CH₂ | — | F | *C(O)CH₂CH₃ | amorphous |
| 2 | CH₂ | — | H | *C(O)CH₃ | amorphous |
| 3 | CH₂ | — | H | *C(O)OCH₃ | amorphous |
| 4 | CH₂ | — | H | *C(O)OCH(CH₃)₂ | amorphous |
| 5 | CH₂ | 2-F | H | *C(O)CH₂CH₃ | amorphous |
| 6 | CH₂ | 2-Cl | H | *C(O)CH₂CH₃ | amorphous |
| 7 | CH₂ | 2-Cl | H | *C(O)CH₂CH(CH₃)OCH₃ | amorphous |
| 8 | CH₂ | — | H | *C(O)Ph | amorphous |
| 9 | CH₂ | — | F | *C(O)CH₂CH₂CH₃ | amorphous |
| 10 | CH₂ | — | F | *C(O)CH(CH₃)₂ | amorphous |
| 11 | CH₂ | — | F | *C(O)-c-Pr | amorphous |

TABLE 10-continued
| Working example number | D | (Z)n | W | R¹ | Physical properties |
|---|---|---|---|---|---|
| 12 | CH₂ | — | F | 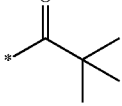 | amorphous |
| 13 | CH₂ | — | F | 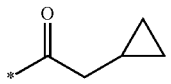 | amorphous |
| 14 | CH₂ | — | F | 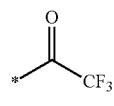 | amorphous |
| 15 | CH₂ | — | F | 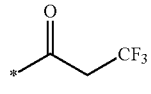 | amorphous |
| 16 | CH₂ | — | F | 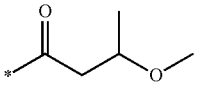 | amorphous |
| 17 | CH₂ | — | F | 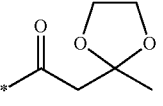 | amorphous |
| 18 | CH₂ | — | F | 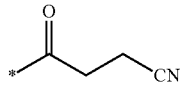 | amorphous |
| 19 | CH₂ | — | Cl | 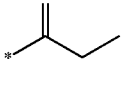 | amorphous |
| 20 | CH₂ | — | Cl | 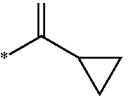 | amorphous |
| 21 | CH₂ | — | Cl | 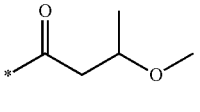 | amorphous |
| 22 | CH₂ | — | Cl | 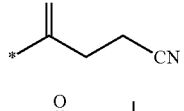 | amorphous |
| 23 | CH₂ | — | Cl | 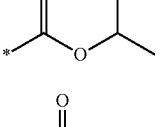 | amorphous |
| 24 | CH₂ | — | Br | 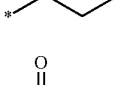 | amorphous |
| 25 | CH₂ | — | Br | 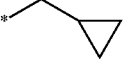 | amorphous |

TABLE 10-continued
| Working example number | D | (Z)n | W | R¹ | Physical properties |
|---|---|---|---|---|---|
| 26 | CH$_2$ | — | Br | 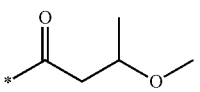 | amorphous |
| 27 | CH$_2$ | — | Br | 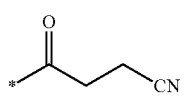 | amorphous |
| 28 | CH$_2$ | — | I | 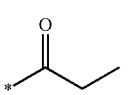 | amorphous |
| 29 | CH$_2$ | — | Me | 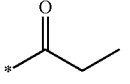 | amorphous |
| 30 | CH$_2$ | — | CN | 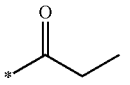 | amorphous |
| 31 | CH$_2$ | — | CF$_3$ | 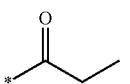 | amorphous |
| 32 | CH$_2$ | — | CF$_3$ | 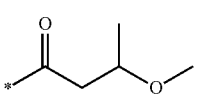 | amorphous |
| 33 | CH$_2$ | — | CF$_3$ | 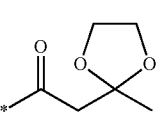 | amorphous |
| 34 | CH$_2$ | — | CF$_3$ | 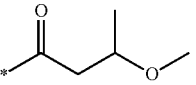 | amorphous |
| 35 | CH$_2$ | — | MeO | 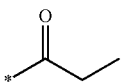 | amorphous |
| 36 | CH$_2$ | 2-F | F | 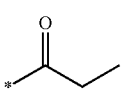 | amorphous |
| 37 | CH$_2$ | 2-F | F | 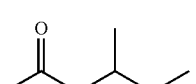 | amorphous |
| 38 | CH$_2$ | 2-F | F | 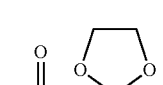 | amorphous |
| 39 | CH$_2$ | 2-F | F | 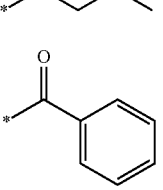 | amorphous |

TABLE 10-continued
| Working example number | D | (Z)n | W | R¹ | Physical properties |
|---|---|---|---|---|---|
| 40 | CH₂ | 2-F | F | 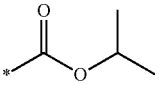 | amorphous |
| 41 | CH₂ | 5-F | F | 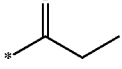 | amorphous |
| 42 | CH₂ | 5-F | F | 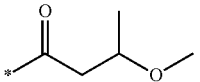 | amorphous |
| 43 | CH₂ | 5-F | F | 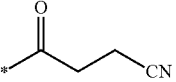 | m.p.: 162-164 |
| 44 | CH₂ | 5-Cl | Cl | 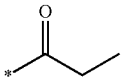 | amorphous |
| 45 | CH₂ | 5-Cl | Cl | 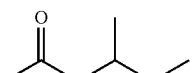 | amorphous |
| 46 | CH₂ | 5-Cl | Cl | 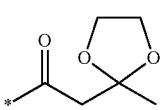 | amorphous |
| 47 | CH₂ | 5-Cl | Cl | 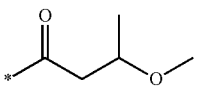 | amorphous |
| 48 | CH₂ | 5-Cl | Cl | 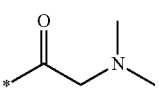 | m.p.: 112-115 |
| 49 | CH(CH₃) | — | H | 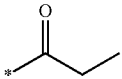 | amorphous |
| 50 | NH | — | H | 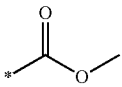 | amorphous |
| 51 | NH | — | H | 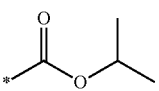 | amorphous |
| 52 | NH | — | Cl |  | amorphous |
| 53 | NH | — | Cl | 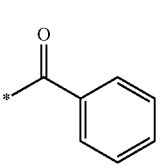 | amorphous |

TABLE 10-continued

| Working example number | D | (Z)n | W | R¹ | Physical properties |
|---|---|---|---|---|---|
| 54 | NH | — | Cl | 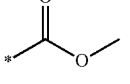 | m.p.: 175-176 |
| 55 | NH | — | Cl | 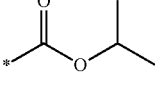 | amorphous |
| 56 | O | — | Cl | 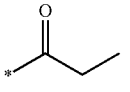 | amorphous |
| 57 | O | — | Cl | 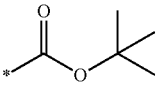 | m.p.: 136-140 |
| 58 | O | — | CN |  | amorphous |

Working Example 59

[Chemical formula 25]

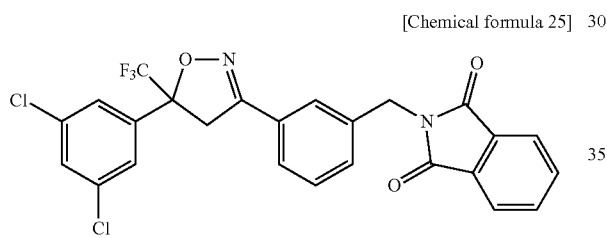

m.p.: 181-183

Working Example 60-61

[Chemical formula 26]

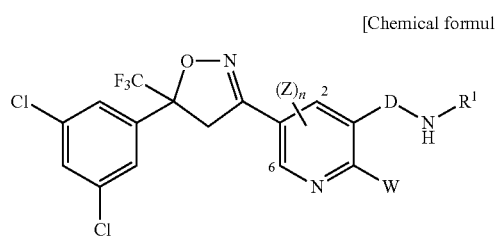

TABLE 11

| Working example number | D | (Z)n | W | R¹ | Physical properties |
|---|---|---|---|---|---|
| 60 | $CH_2$ | 2-Cl | H | 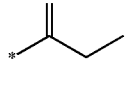 | amorphous |
| 61 | $CH_2$ | 2-Me | H | 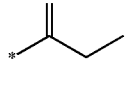 | amorphous |

Of the compounds of the aforementioned working examples, $^1$H-NMR (CDCl$_3$, δppm) is shown below for the compounds which are amorphous.

TABLE 12

| Working example number | $^1$H-NMR (CDCl$_3$, δppm) |
|---|---|
| 1 | 1.17 (t, 3H), 2.25 (q, 2H), 3.68 (d, 1H), 4.07 (d, 1H), 4.49 (d, 2H), 5.84 (m, 1H), 7.08-7.67 (m, 6H) |
| 2 | 2.18 (s, 3H), 3.68 (d, 1H), 4.06 (d, 1H), 4.66 (d, 2H), 7.33-7.58 (m, 7H) |
| 3 | 3.69 (d, 1H), 3.72 (s, 3H), 4.08 (d, 1H), 4.39 (d, 2H), 5.04 (m, 1H), 7.39-7.59 (m, 7H) |
| 4 | 1.25 (d, 6H), 3.69 (d, 1H), 4.08 (d, 1H), 4.38 (d, 2H), 4.95 (m, 1H), 7.39-7.59 (m, 7H) |
| 5 | 1.18 (t, 3H), 2.25 (q, 2H), 3.78 (d, 1H), 4.11 (d, 1H), 4.50 (d, 2H), 5.78 (m, 1H), 7.14-7.49 (m, 6H) |

TABLE 12-continued

| Working example number | ¹H-NMR (CDCl₃, δppm) |
|---|---|
| 6 | 1.18 (t, 3H), 2.26 (q, 2H), 3.81 (d, 1H), 4.21 (d, 1H), 4.60 (d, 2H), 5.93 (m, 1H), 7.28-7.60 (m, 6H) |
| 7 | 1.20 (d, 3H), 2.34-2.47 (m, 2H), 3.34 (s, 3H), 3.67-3.85 (m, 2H), 4.17 (dd, 1H), 4.48-4.63 (m, 2H), 6.82 (m, 1H), 7.28-7.54 (m, 6H) |
| 8 | 3.69 (d, 1H), 4.08 (d, 1H), 4.68 (d, 2H), 6.48 (m, 1H), 7.39-7.81 (m, 7H) |
| 9 | 0.95 (t, 3H), 1.62-1.74 (m, 2H), 2.22 (q, 2H), 3.67 (d, 1H), 4.06 (d, 1H), 4.49 (d, 2H), 5.92 (m, 1H), 7.06-7.67 (m, 6H) |
| 10 | 1.16 (d, 6H), 2.42-2.46 (m, 1H), 3.67 (d, 1H), 4.07 (d, 1H), 4.48 (d, 2H), 5.91 (m, 1H), 7.08-7.66 (m, 6H) |
| 11 | 0.75-0.81 (m, 2H), 0.97-1.01 (m, 2H), 1.33-1.41 (m, 1H), 3.67 (d, 1H), 4.06 (d, 1H), 4.50 (d, 2H), 6.04 (m, 1H), 7.08-7.67 (m, 6H) |
| 12 | 1.21 (s, 9H), 3.7 (d, 1H), 4.06 (d, 1H), 4.47 (d, 2H), 6.08 (m, 1H), 7.08-7.65 (m, 6H) |
| 13 | 0.18-0.23 (m, 2H), 0.60-0.66 (m, 2H), 0.93-1.02 (m, 1H), 2.19 (d, 2H), 3.68 (d, 1H), 4.05 (d, 1H), 4.52 (d, 2H), 6.35 (m, 1H), 7.08-7.66 (m, 6H) |
| 14 | 3.68 (d, 1H), 4.07 (d, 1H), 4.59 (d, 2H), 6.73 (m, 1H), 7.14-7.72 (m, 6H) |
| 15 | 3.07-3.17 (m, 2H), 3.67 (d, 1H), 4.04 (d, 1H), 4.54 (d, 2H), 6.26 (m, 1H), 7.10-7.70 (m, 6H) |
| 16 | 1.20 (d, 3H), 2.34-2.47 (m, 2H), 3.34 (s, 3H), 3.65-3.76 (m, 2H), 4.06 (d, 1H), 4.49 (d, 2H), 6.75 (m, 1H), 7.07-7.64 (m, 6H) |
| 17 | 1.28 (s, 3H), 2.66 (s, 2H), 3.67 (d, 1H), 3.92-4.16 (m, 5H), 4.50 (d, 2H), 6.81 (m, 1H), 7.08-7.68 (m, 6H) |
| 18 | 2.58 (t, 2H), 2.73 (t, 2H), 3.71 (d, 1H), 4.07 (d, 1H), 4.54 (d, 2H), 6.02 (m, 1H), 7.09-7.72 (m, 6H) |
| 19 | 1.16 (t, 3H), 2.26 (q, 2H), 3.68 (d, 1H), 4.06 (d, 1H), 4.51 (d, 2H), 5.97 (m, 1H), 7.40-7.64 (m, 6H) |
| 20 | 0.75-0.81 (m2H), 0.97-1.02 (m, 2H), 1.35-1.43 (m, 1H), 3.68 (d, 1H), 4.06 (d, 1H), 4.53 (d, 2H), 6.88 (m, 1H), 7.40-7.64 (m, 6H) |
| 21 | 1.21 (d, 3H), 2.34-2.48 (m, 2H), 3.34 (s, 3H), 3.65-3.71 (m, 2H), 4.06 (d, 1H), 4.53 (d, 2H), 6.88 (m, 1H), 7.40-7.64 (m, 6H) |
| 22 | 2.60 (t, 2H), 2.73 (t, 2H), 3.71 (d, 1H), 4.07 (d, 1H), 4.58 (d, 2H), 6.04 (m, 1H), 7.41-7.67 (m, 6H) |
| 23 | 1.24 (d, 6H), 3.67 (d, 1H), 4.06 (d, 1H), 4.45 (d, 2H), 4.88-5.12 (m, 2H), 7.32-7.63 (m, 6H) |
| 24 | 1.16 (t, 3H), 2.26 (q, 2H), 3.69 (d, 1H), 4.07 (d, 1H), 6.02 (m, 1H), 7.42-7.92 (m, 6H) |
| 26 | 1.20 (d, 3H), 2.35-2.49 (m, 2H), 3.35 (s, 3H), 3.66-3.76 (m, 2H), 4.06 (d, 1H), 4.51 (d, 2H), 6.94 (m, 1H), 7.41-7.63 (m, 6H) |
| 27 | 2.60 (t, 2H), 2.73 (t, 2H), 3.71 (d, 1H), 4.08 (d, 1H), 4.56 (d, 2H), 6.15 (m, 1H), 7.41-7.63 (m, 6H) |
| 28 | 1.16 (t, 3H), 2.24 (q, 2H), 3.68 (d, 1H), 4.06 (d, 1H), 4.52 (d, 2H), 5.97 (m, 1H), 7.42-7.62 (m, 6H) |
| 29 | 1.17 (t, 3H), 2.26 (q, 2H), 2.36 (s, 3H), 3.67 (d, 1H), 4.06 (d, 1H), 4.45 (d, 2H), 5.64 (m, 1H), 7.21-7.59 (m, 6H) |
| 30 | 1.17 (t, 3H), 2.26 (q, 2H), 3.68 (d, 1H), 4.07 (d, 1H), 4.59 (d, 2H), 7.42-7.76 (m, 6H) |
| 31 | 1.17 (t, 3H), 2.27 (q, 2H), 3.73 (d, 1H), 4.09 (d, 1H), 4.62 (d, 2H), 6.01 (m, 1H), 7.42-7.81 (m, 6H) |
| 32 | 1.20 (d, 3H), 2.35-2.49 (m, 2H), 3.32 (s, 3H), 3.69-3.77 (m, 2H), 4.08 (d, 1H), 4.63 (d, 2H), 6.88 (m, 1H), 7.42-7.82 (m, 6H) |
| 33 | 1.41 (s, 3H), 2.68 (s, 2H), 3.72 (d, 1H), 3.87-3.98 (m, 4H), 4.06 (d, 1H), 4.65 (d, 2H), 6.86 (m, 1H), 7.43-7.80 (m, 6H) |
| 34 | 2.57-2.76 (m, 4H), 3.75 (d, 1H), 4.11 (d, 1H), 4.66 (d, 2H), 6.18 (m, 1H), 7.42-8.32 (m, 6H) |
| 35 | 1.16 (t, 3H), 2.24 (q, 2H), 3.67 (d, 1H), 3.91 (s, 3H), 4.07 (d, 1H), 4.43 (d, 2H), 5.89 (m, 1H), 6.91 (d, 1H), 7.41-7.71 (m, 5H) |
| 36 | 1.14 (t, 3H), 2.19 (q, 2H), 3.78 (d, 1H), 4.16 (d, 1H), 4.55 (d, 2H), 5.76 (m, 1H), 6.93-7.89 (m, 5H) |
| 37 | 1.16 (d, 3H), 2.33-2.36 (m, 2H), 3.66 (d, 1H), 3.76 (d, 1H), 4.15 (d, 1H), 4.54 (d, 2H), 6.70 (m, 1H), 6.93-7.88 (m, 5H) |
| 38 | 1.35 (s, 3H), 2.60 (s, 2H), 3.78 (d, 1H), 3.88-3.99 (m, 4H), 4.15 (d, 1H), 4.55 (d, 2H), 6.80 (m, 1H), 6.91-7.88 (m, 5H) |
| 39 | 3.78 (d, 1H), 4.17 (d, 1H), 4.75 (d, 2H), 6.55 (m, 1H), 6.97-7.90 (m, 10H) |
| 40 | 1.21 (d, 6H), 3.78 (d, 1H), 4.16 (d, 1H), 4.46 (d, 2H), 4.86-4.99 (m, 2H), 6.95-7.89 (m, 5H) |
| 41 | 1.16 (t, 3H), 2.25 (q, 2H), 3.67 (d, 1H), 4.04 (d, 1H), 4.50 (d, 2H), 6.81 (m, 1H), 7.36-7.53 (m, 5H) |
| 42 | 1.15 (d, 3H), 2.33-2.49 (m, 2H), 3.34 (s, 3H), 3.63-3.76 (m, 2H), 4.04 (d, 1H), 4.51 (d, 2H) 6.82 (m, 1H), 7.37-7.53 (m, 5H) |
| 44 | 1.18 (t, 3H), 2.27 (q, 2H), 3.68 (d, 1H), 4.05 (d, 1H), 4.53 (d, 2H), 6.08 (m, 1H), 7.42-7.73 (m, 5H) |
| 45 | 1.21 (d, 3H), 2.35-2.50 (m, 2H), 3.35 (s, 3H), 3.67-3.78 (m, 2H), 4.05 (d, 1H), 4.53 (d, 2H), 6.96 (m, 1H), 7.42-7.72 (m, 5H) |
| 46 | 1.46 (s, 3H), 2.67 (s, 2H), 3.68 (d, 1H), 3.93-4.09 (m, 5H), 4.54 (d, 2H), 6.98 (m, 1H), 7.43-7.76 (m, 5H) |
| 47 | 2.59-2.75 (m, 4H), 3.71 (d, 1H), 4.05 (d, 1H), 4.56 (d, 2H), 6.41 (m, 1H), 7.41-7.77 (m, 5H) |

TABLE 12-continued

| Working example number | ¹H-NMR (CDCl₃, δppm) |
|---|---|
| 49 | 1.15 (t, 3H), 1.49 (d, 3H), 2.24 (q, 2H), 3.69 (d, 1H), 4.08 (d, 1H), 5.16 (m, 1H), 5.67 (m, 1H), 7.36-7.64 (m, 7H) |
| 50 | 3.66 (d, 1H), 3.77 (s, 3H), 4.06 (d, 1H), 5.84 (m, 1H), 6.53 (m, 1H), 6.91-7.51 (m, 7H) |
| 51 | 1.27 (d, 6H), 3.65 (d, 1H), 4.05 (d, 1H), 4.96 (m, 1H), 5.84 (m, 1H), 6.45 (m, 1H), 6.91-7.51 (m, 7H) |
| 52 | 2.11 (s, 3H), 3.65 (d, 1H), 4.07 (d, 1H), 6.91-7.48 (m, 7H) |
| 53 | 3.61 (d, 1H), 3.99 (d, 1H), 6.73-8.08 (m, 13H) |
| 55 | 1.27 (d, 6H), 3.64 (d, 1H), 4.04 (d, 1H), 4.98 (m, 1H), 6.31 (m, 1H), 6.43 (m, 1H), 7.00-7.50 (m, 6H) |
| 56 | 1.17 (t, 3H), 2.36 (q, 2H), 3.67 (d, 1H), 4.05 (d, 1H), 7.20-7.56 (m, 7H) |
| 58 | 2.12 (s, 3H), 3.68 (d, 1H), 4.06 (d, 1H), 7.30-7.78 (m, 6H) |
| 60 | 1.16 (t, 3H), 2.29 (q, 2H), 3.69 (d, 1H), 4.07 (d, 1H), 4.51 (d, 2H), 6.06 (m, 1H), 7.43-8.62 (m, 5H) |
| 61 | 1.18 (t, 3H), 2.30 (q, 2H), 3.69 (d, 1H), 4.07 (d, 1H), 4.47 (d, 2H), 5.93 (m, 1H), 7.43-8.55 (m, 5H) |

FORMULATION EXAMPLES

Next, some working examples of compositions of the present invention are shown, but additives and addition ratios are not limited by these working examples, and can be modified over a wide range. Moreover, the term "parts" used in these formulation examples indicate "mass parts."

FORMULATION EXAMPLE 1

Wettable Powder

| Compound of the present invention | 40 parts |
|---|---|
| Clay | 48 parts |
| Sodium dioctylsulfosuccinate salt | 4 parts |
| Sodium lignin sulfonate salt | 8 parts |

The foregoing is uniformly mixed and finely pulverized to obtain a wettable powder of 40% active ingredient.

FORMULATION EXAMPLE 2

Emulsion

| Compound of the present invention | 10 parts |
|---|---|
| Solvesso 200 | 53 parts |
| Cyclohexanone | 26 parts |
| Calcium dodecyl benzene sulfonate salt | 1 part |
| Polyoxyethylene alkylallyl ether | 10 parts |

The foregoing is mixed and dissolved to obtain an emulsion of 10% active ingredient.

Formulation Example 3

Dust Agent

| Compound of the present invention | 10 parts |
|---|---|
| Clay | 90 parts |

The foregoing is uniformly mixed and finely pulverized to obtain a dust agent of 40% active ingredient.

FORMULATION EXAMPLE 4

Granular Agent

| Compound of the present invention | 5 parts |
|---|---|
| Clay | 73 parts |
| Bentonite | 20 parts |
| Sodium dioctylsulfosuccinate salt | 1 part |
| Potassium phosphate | 1 part |

The foregoing is thoroughly pulverized and mixed, water is added, and kneading is thoroughly conducted, after which granulation and drying are conducted to obtain a granular agent of 5% active ingredient.

FORMULATION EXAMPLE 5

Suspension

| Compound of the present invention | 10 parts |
|---|---|
| Polyoxyethylene alkylallyl ether | 4 parts |
| Sodium polycarboxylate salt | 2 parts |
| Glycerin | 10 parts |
| Xanthan gum | 0.2 part |
| Water | 73.8 parts |

The foregoing is mixed, and wet crushing is conducted until particle size is 3 microns or less to obtain a suspension of a 10% active ingredient.

FORMULATION EXAMPLE 6

Granular Wettable Powder

| Compound of the present invention | 40 parts |
|---|---|
| Clay | 36 parts |
| Potassium chloride | 10 parts |

| | |
|---|---|
| Sodium alkylbenzene sulfonate salt | 1 part |
| Sodium lignin sulfonate salt | 8 parts |
| Formaldehyde condensate of sodium alkylbenzene sulfonate salt | 5 parts |

The foregoing is uniformly mixed and finely pulverized, and a suitable amount of water is added, and kneaded to be argillaceous. After the argillaceous substance is granulated, it is dried to obtain a granular wettable powder of 40% active ingredient.

(Test Cases)

Test cases of the pest-control agents of the present invention obtained in the foregoing manner are shown below.

Test case 1 Efficacy against *Aphis gossypii*

Cucumbers seeded in a pot with a diameter of 9 cm which had germinated for 10 days were inoculated with adult *Aphis gossypii*. The adult insects were removed after one day, and the cucumbers which were parasitized with the produced offspring were subjected to application of a chemical solution that was prepared according to the prescription of the emulsion shown in the aforementioned Formulation Example 2 and that was diluted with water to a compound concentration of 125 ppm. Stored in a temperature-controlled room at a temperature of 25° C. and a humidity of 65%, mortality was investigated after five days, and the insect mortality rate was obtained. The test was repeated twice. As a result, the following compounds exhibited a 100% mortality rate.

Compound number: working example 1, working example 11, working example 16, working example 18, working example 19, working example 22, working example 28, example 30, working examples 36-38, working example 44, and working example 45.

The mortality rate of pirimicarb used for control was 9%.

Test Case 2 Efficacy Against *Tetranychus urticae*

Beans seeded in a pot with a diameter of 9 cm which had germinated for 7-10 days were inoculated on a first leaf with 17 female adults of *Tetranychus urticae* with organophosphate resistance, after which a chemical solution was applied that was prepared according to the prescription of the wettable powder shown in the aforementioned Formulation Example 1 and that was diluted with water to a compound concentration of 125 ppm. Stored in a temperature-controlled room at a temperature of 25° C. and a humidity of 65%, the insect mortality rate was investigated after three days. The test was repeated twice. As a result, the following compounds exhibited a 100% mortality rate.

Compound number: working example 1, working example 11, working example 18, working example 19, working example 22, working examples 28-30, working examples 36-38, working example 44, working example 45, and working example 47.

The mortality rate of chlordimeform used for control was 9%.

Test Case 3 Efficacy Against *Spodoptera litura*

Following the prescription of the emulsion shown in the aforementioned Formulation Example 2, dilution with water was conducted to a compound concentration of 125 ppm. Cabbage leaves were immersed in the chemical solution for 30 seconds, dried by air, and inserted into a petri dish lined with filter paper, and inoculated with 5 second-instar larvae of *Spodoptera litura*. A glass lid was put on, and storage was conducted in a temperature-controlled room at a temperature of 25° C. and a humidity of 65%. Mortality was investigated after five days, and the insect mortality rate was obtained. The test was repeated twice. As a result, the following compounds exhibited a 100% mortality rate.

Compound number: working example 1, working example 5, working example 11, working examples 16-19, working examples 21-23, working examples 28-30, working examples 36-40, working example 44, working example 45, working example 47, working example 48, working example 51, working example 52, working example 54, working example 55, working example 58, and working example 60.

Test Case 4 Test of Efficacy Against *Culex Pipiens*

10 larvae of *Culex pipiens molestus*, which were hatched 1 day before, and 0.225 ml of distilled water containing 0.5 mg of feed for aquarium fish (TetraMin® manufactured by Tetra Japan Co. Ltd) were put into a polystyrene test container with a volume of 0.3 ml.

The compound was adjusted to a 1% solution using DMSO (containing 0.5% Tween-20), and further diluted to 0.01% with distilled water. 0.025 ml of this diluted chemical solution was added to a test container into which *Culex* pipiens had been inserted, and stirring was conducted (final concentration of compound: 0.001%).

This was left standing at 25° C., and the mortality rate was investigated after two days. The test was conducted with two repetitions.

In this test, the following compounds were effective with a mortality rate of 90% or more.

Compound number: working example 19, working examples 21-23, working example 44, working example 45, working example 47

INDUSTRIAL APPLICABILITY

According to the present invention, it is possible to offer industrially useful pest control agents whose active ingredient is at least one type of novel nitrogen-containing heterocyclic compound or its salt, or a compound thereof, which can be industrially synthesized in an expedient manner, and which can constitute the active ingredient of pest control agents that are reliably effective and that can be safely used.

The invention claimed is:

1. A compound expressed by formula (XVI) or salt thereof:

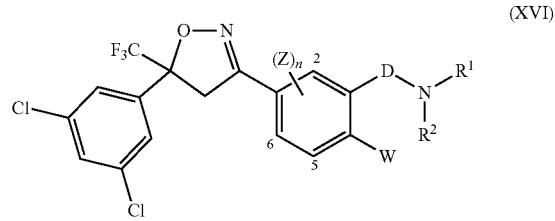

In the formula,
Z indicates a nitro group, hydroxyl group, mercapto group, halogen atom, alkyl group, cyano group, or a group expressed by $N(R^a)_2$, in the formula, each $R^a$ indicates a hydrogen atom or a hydrocarbon group;
n indicates 0;
D indicates a group expressed by the following formula:

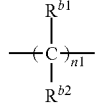

in the formula, $R^{b1}$ and $R^{b2}$ indicate hydrogen atoms; n1 indicates 1;

W indicates a halogen atom, or an alkyl group; and $R^1$ and $R^2$ indicate hydrogen atoms, acyl groups, or alkoxycarbonyl groups.

2. A pest control agent comprising the compound or salt thereof according to claim 1 as an active ingredient.

3. The pest control agent according to claim 2, wherein said pest control agent is an insecticide or acaricide.

* * * * *